United States Patent
Angle et al.

(10) Patent No.: US 9,796,078 B2
(45) Date of Patent: Oct. 24, 2017

(54) COMPANION ROBOT FOR PERSONAL INTERACTION

(71) Applicant: iRobot Corporation, Bedford, MA (US)

(72) Inventors: Colin Angle, Cambridge, MA (US);
Clara Vu, Cambridge, MA (US);
Matthew Cross, Mason, NH (US);
Tony L. Campbell, Pepperell, MA (US)

(73) Assignee: iRobot Corporation, Bedford, MA (US)

( * ) Notice: Subject to any disclaimer, the term of this patent is extended or adjusted under 35 U.S.C. 154(b) by 518 days.

(21) Appl. No.: 14/044,170

(22) Filed: Oct. 2, 2013

(65) Prior Publication Data
US 2014/0039680 A1 Feb. 6, 2014

Related U.S. Application Data

(63) Continuation of application No. 11/541,422, filed on Sep. 29, 2006, now Pat. No. 8,583,282.
(Continued)

(51) Int. Cl.
*B25J 9/00* (2006.01)
*B25J 5/00* (2006.01)
(Continued)

(52) U.S. Cl.
CPC .............. *B25J 9/0003* (2013.01); *B25J 5/007* (2013.01); *B25J 9/1697* (2013.01); *B25J 11/008* (2013.01); *B25J 19/0091* (2013.01); *B25J 19/023* (2013.01); *B25J 19/06* (2013.01); *G05D 1/021* (2013.01); *G05D 1/0246* (2013.01); *G05D 1/0272* (2013.01); *G05D 1/0274* (2013.01);
(Continued)

(58) Field of Classification Search
CPC ........ B25J 5/007; B25J 9/0003; B25J 9/1689; G06F 19/3418; G06F 19/3425
USPC ......................................................... 700/245
See application file for complete search history.

(56) References Cited

U.S. PATENT DOCUMENTS

| 5,276,618 A | 1/1994 | Everett et al. |
| 5,341,540 A | 8/1994 | Soupert et al. |

(Continued)

FOREIGN PATENT DOCUMENTS

| JP | 2001-101144 A | 4/2001 |
| JP | 2002-355779 A | 12/2002 |

(Continued)

OTHER PUBLICATIONS

Australian examination report for related Application No. 2011256720 dated Mar. 27, 2014.
(Continued)

*Primary Examiner* — Thomas G Black
*Assistant Examiner* — Sze-Hon Kong
(74) *Attorney, Agent, or Firm* — Fish & Richardson P.C.

(57) ABSTRACT

A mobile robot that includes a robot body, a drive system having one or more wheels supporting the robot body to maneuver the robot across a floor surface, and a riser having a proximal end and a distal end. The proximal end of the riser disposed on the robot body. The robot also includes a head disposed on the distal end of the riser. The head includes a display and a camera disposed adjacent the display.

20 Claims, 41 Drawing Sheets

Related U.S. Application Data

(60) Provisional application No. 60/722,935, filed on Sep. 30, 2005, provisional application No. 60/745,006, filed on Apr. 17, 2006, provisional application No. 60/746,491, filed on May 4, 2006.

(51) Int. Cl.

| | | |
|---|---|---|
| *B25J 19/00* | (2006.01) | |
| *B25J 19/02* | (2006.01) | |
| *B25J 19/06* | (2006.01) | |
| *G06F 19/00* | (2011.01) | |
| *G06N 3/00* | (2006.01) | |
| *B25J 9/16* | (2006.01) | |
| *B25J 11/00* | (2006.01) | |
| *G05D 1/02* | (2006.01) | |

(52) U.S. Cl.
CPC ...... *G06F 19/3406* (2013.01); *G06F 19/3418* (2013.01); *G06F 19/3462* (2013.01); *G06N 3/008* (2013.01); *G05D 1/027* (2013.01); *G05D 1/0225* (2013.01); *G05D 1/0234* (2013.01); *G05D 1/0242* (2013.01); *G05D 1/0251* (2013.01); *G05D 1/0255* (2013.01); *G05D 2201/0207* (2013.01); *Y10S 901/01* (2013.01); *Y10S 901/46* (2013.01); *Y10S 901/47* (2013.01)

(56) References Cited

U.S. PATENT DOCUMENTS

| | | | | |
|---|---|---|---|---|
| 5,802,494 | A * | 9/1998 | Kuno | ................................ 705/2 |
| 5,808,663 | A * | 9/1998 | Okaya | .......................... 348/14.1 |
| 6,445,978 | B1 | 9/2002 | Takamura et al. | |
| 6,542,788 | B2 | 4/2003 | Hosonuma et al. | |
| 6,658,325 | B2 | 12/2003 | Zweig | |
| 6,888,333 | B2 | 5/2005 | Laby | |
| 6,914,622 | B1 * | 7/2005 | Smith | ................ A47B 21/0073 348/14.05 |
| 6,925,357 | B2 | 8/2005 | Wang et al. | |
| 7,123,285 | B2 * | 10/2006 | Smith et al. | ................ 348/14.05 |
| 7,158,859 | B2 | 1/2007 | Wang et al. | |
| 7,289,883 | B2 * | 10/2007 | Wang et al. | ................... 700/245 |
| 7,388,879 | B2 | 6/2008 | Sabe et al. | |
| 7,388,981 | B2 * | 6/2008 | Jouppi | ........................... 382/154 |
| 7,467,026 | B2 | 12/2008 | Sakagami et al. | |
| 7,515,992 | B2 | 4/2009 | Sawada et al. | |
| 7,593,030 | B2 | 9/2009 | Wang et al. | |
| 7,593,546 | B2 * | 9/2009 | Jouppi | ........................... 382/103 |
| 7,643,051 | B2 * | 1/2010 | Sandberg et al. | ........... 348/14.02 |
| 7,706,917 | B1 | 4/2010 | Chiappetta et al. | |
| 8,077,963 | B2 * | 12/2011 | Wang et al. | ................... 382/153 |
| 8,515,577 | B2 * | 8/2013 | Wang et al. | ................... 700/247 |
| 2002/0165790 | A1 | 11/2002 | Bancroft et al. | |
| 2002/0198626 | A1 | 12/2002 | Imai et al. | |
| 2003/0109960 | A1 | 6/2003 | Nourbakhsh et al. | |
| 2003/0151658 | A1 * | 8/2003 | Smith | .......................... 348/14.01 |
| 2004/0019406 | A1 * | 1/2004 | Wang et al. | ................... 700/231 |
| 2004/0078219 | A1 | 4/2004 | Kaylor et al. | |
| 2004/0093650 | A1 | 5/2004 | Martins et al. | |
| 2004/0102166 | A1 * | 5/2004 | Morita et al. | ............... 455/152.1 |
| 2004/0113777 | A1 | 6/2004 | Matsuhira et al. | |
| 2004/0162637 | A1 | 8/2004 | Wang et al. | |
| 2004/0167668 | A1 | 8/2004 | Wang et al. | |
| 2004/0174129 | A1 * | 9/2004 | Wang et al. | ............. 318/568.12 |
| 2005/0091684 | A1 | 4/2005 | Kawabata et al. | |
| 2005/0215171 | A1 | 9/2005 | Oonaka | |
| 2005/0216124 | A1 | 9/2005 | Suzuki | |
| 2005/0216126 | A1 | 9/2005 | Koselka et al. | |
| 2006/0082642 | A1 * | 4/2006 | Wang | ..................... H04N 7/142 348/14.05 |
| 2006/0217837 | A1 * | 9/2006 | Koga et al. | .................... 700/245 |
| 2007/0055116 | A1 * | 3/2007 | Clark et al. | .................... 600/300 |
| 2007/0061041 | A1 * | 3/2007 | Zweig | ........................... 700/245 |
| 2007/0064092 | A1 * | 3/2007 | Sandbeg et al. | ........... 348/14.02 |
| 2008/0007203 | A1 | 1/2008 | Cohen et al. | |
| 2013/0117867 | A1 * | 5/2013 | Fung | ............................... 726/35 |

FOREIGN PATENT DOCUMENTS

| | | |
|---|---|---|
| JP | 2004-337556 A | 12/2004 |
| JP | 2005-103679 A | 4/2005 |
| WO | WO-2007041295 A2 | 4/2007 |

OTHER PUBLICATIONS

Canadian Office Action for related Application No. 2,800,372 dated Apr. 2, 2014.
International Search Report and Written Opinion for PCT/US2006/038063, dated May 7, 2007.
Maxwell et al., "Alfred: The Robot Waiter Who Remembers You," XP003001345 Swarthmore College, Swarthmore, PA 1981.
Examination Report for EP Application No. 10183416, dated Dec. 30, 2010.
Examination Report for EP Application No. 10183508, dated Dec. 30, 2010.
Examination Report for EP Application No. 10183416, dated Jan. 20, 2011.
Examination Report for EP Application No. 10183508, dated Jan. 20, 2011.
Examination Report for JP Application No. 2008-533659, dated Aug. 16, 2011.
Office Action for U.S. Appl. No. 11/541,422, dated Jul. 22, 2010.
Office Action for U.S. Appl. No. 11/541,422, dated Mar. 18, 2011.
Office Action for U.S. Appl. No. 11/541,422, dated Feb. 16, 2012.
Office Action for U.S. Appl. No. 11/541,422, dated Sep. 13, 2012.

* cited by examiner

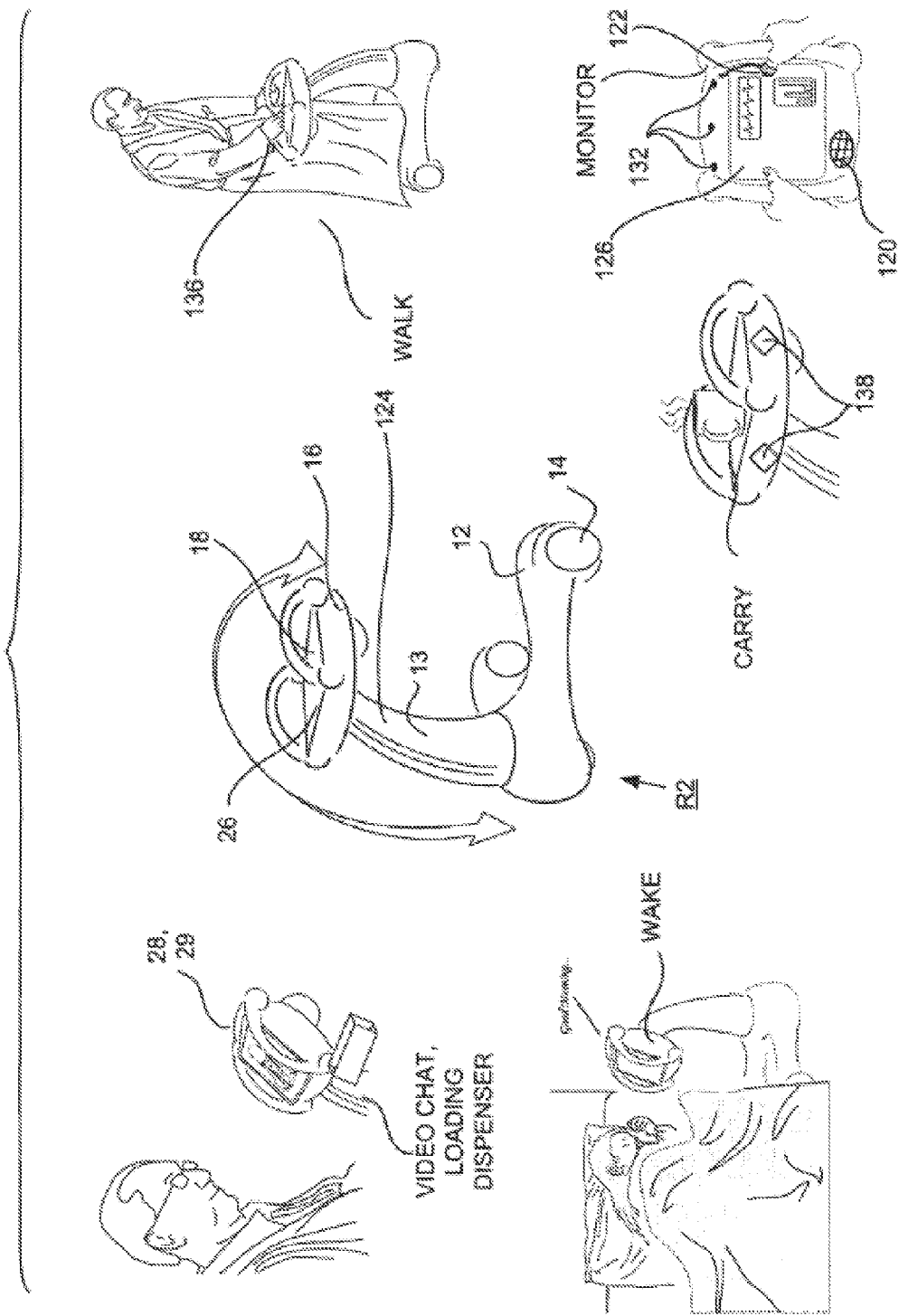

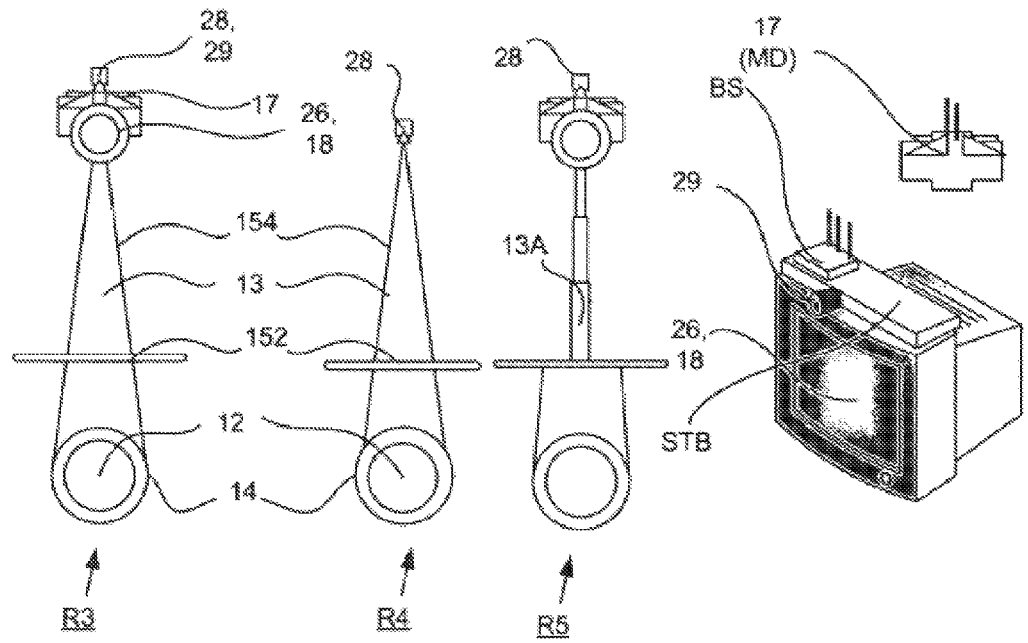
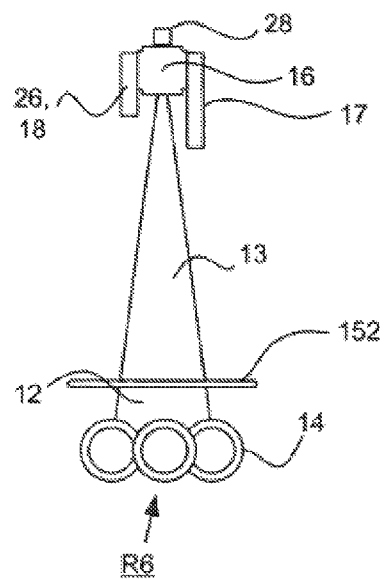
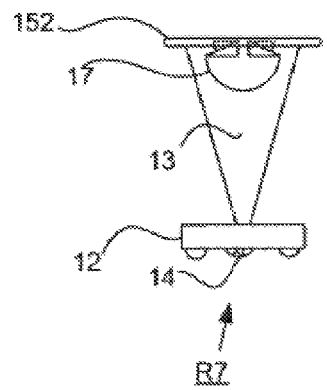

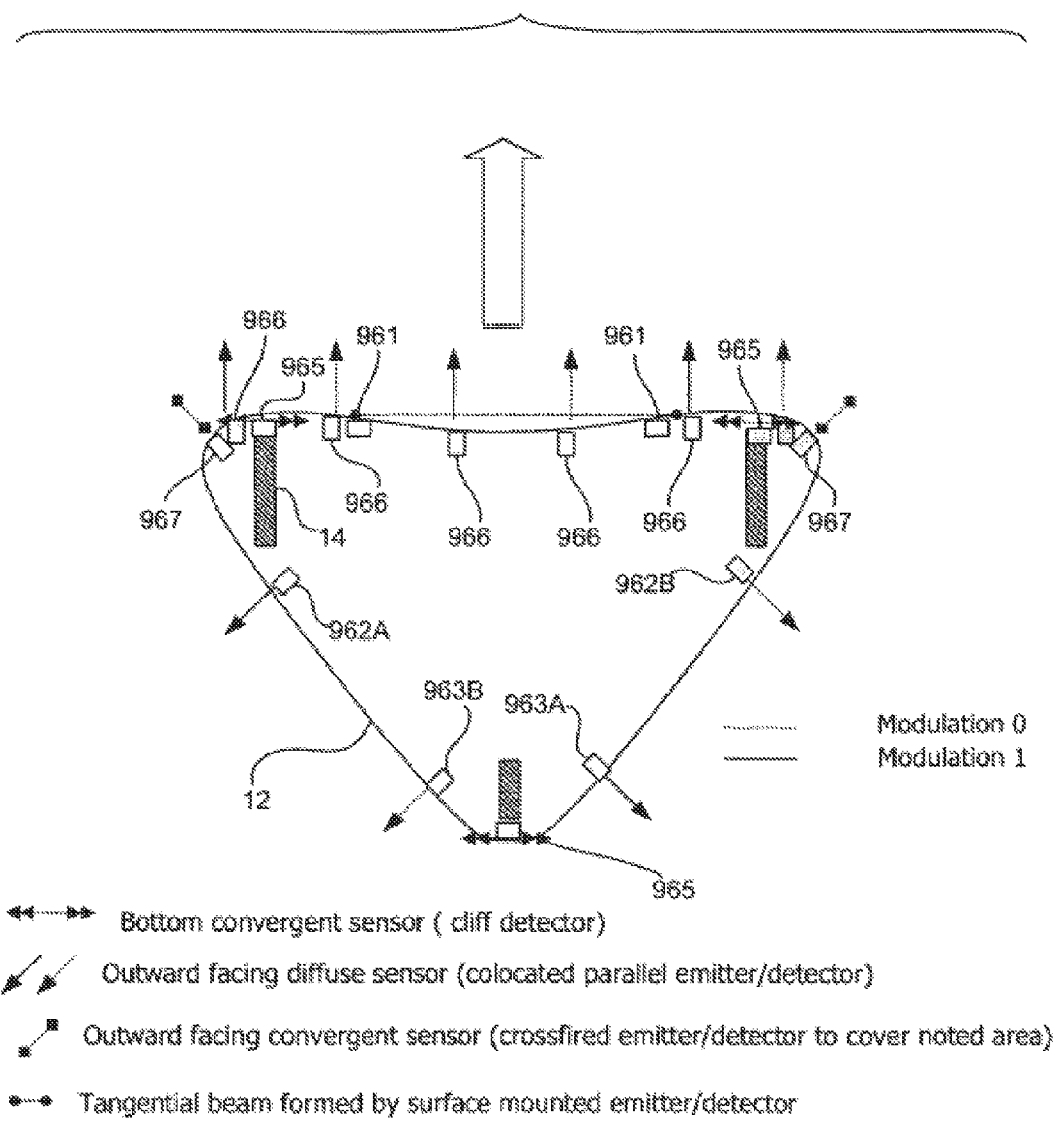

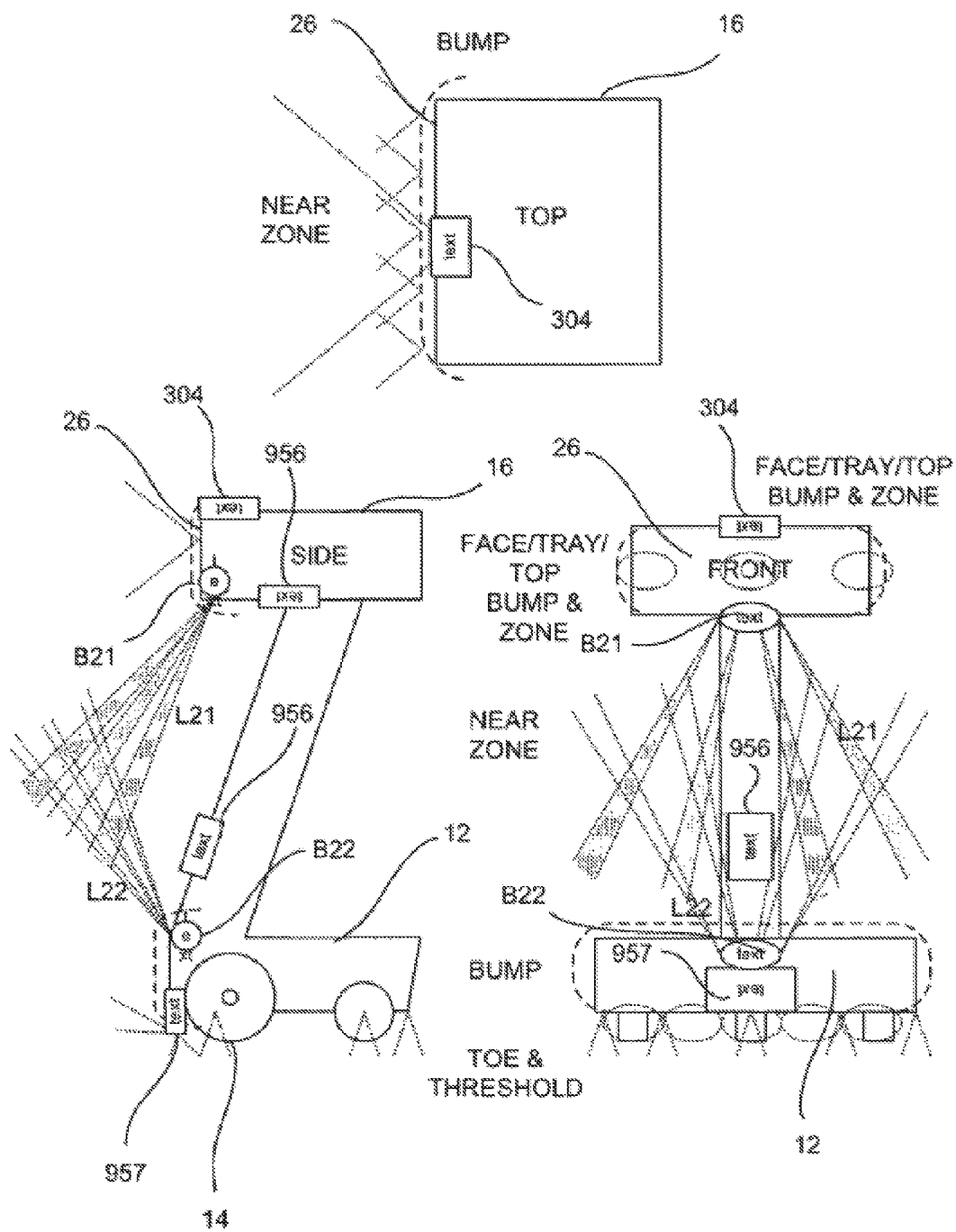

FIG. 5A
FIG. 5B
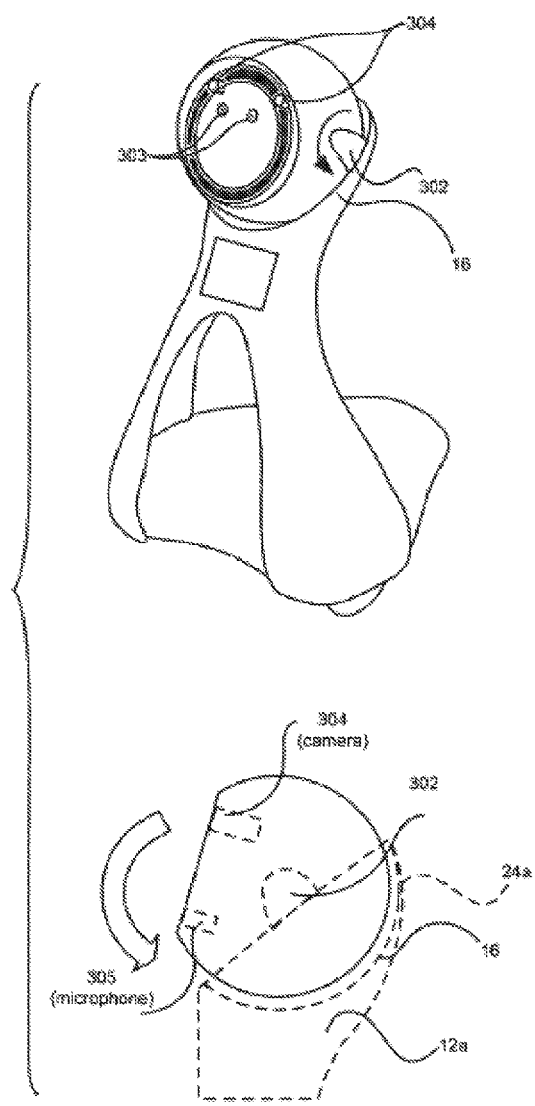
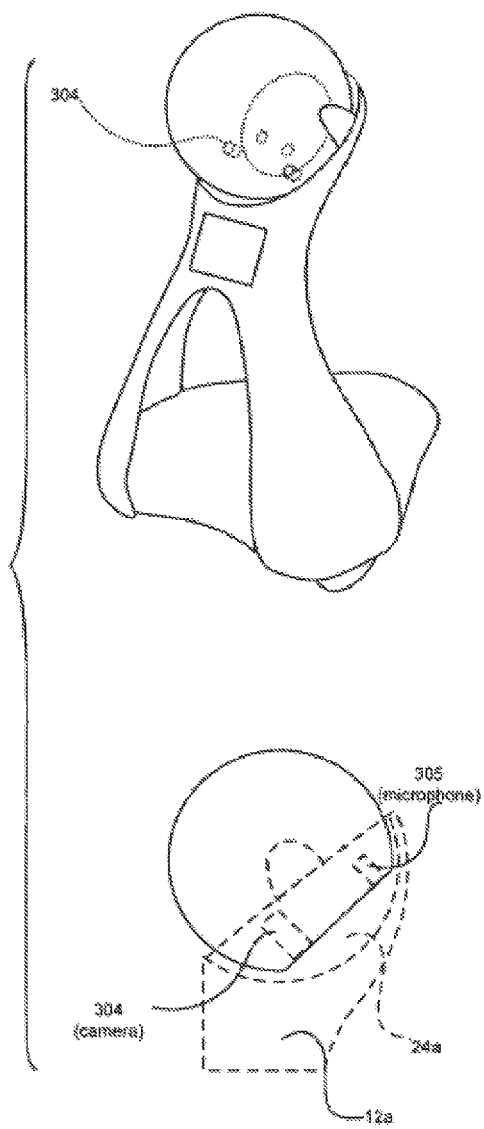

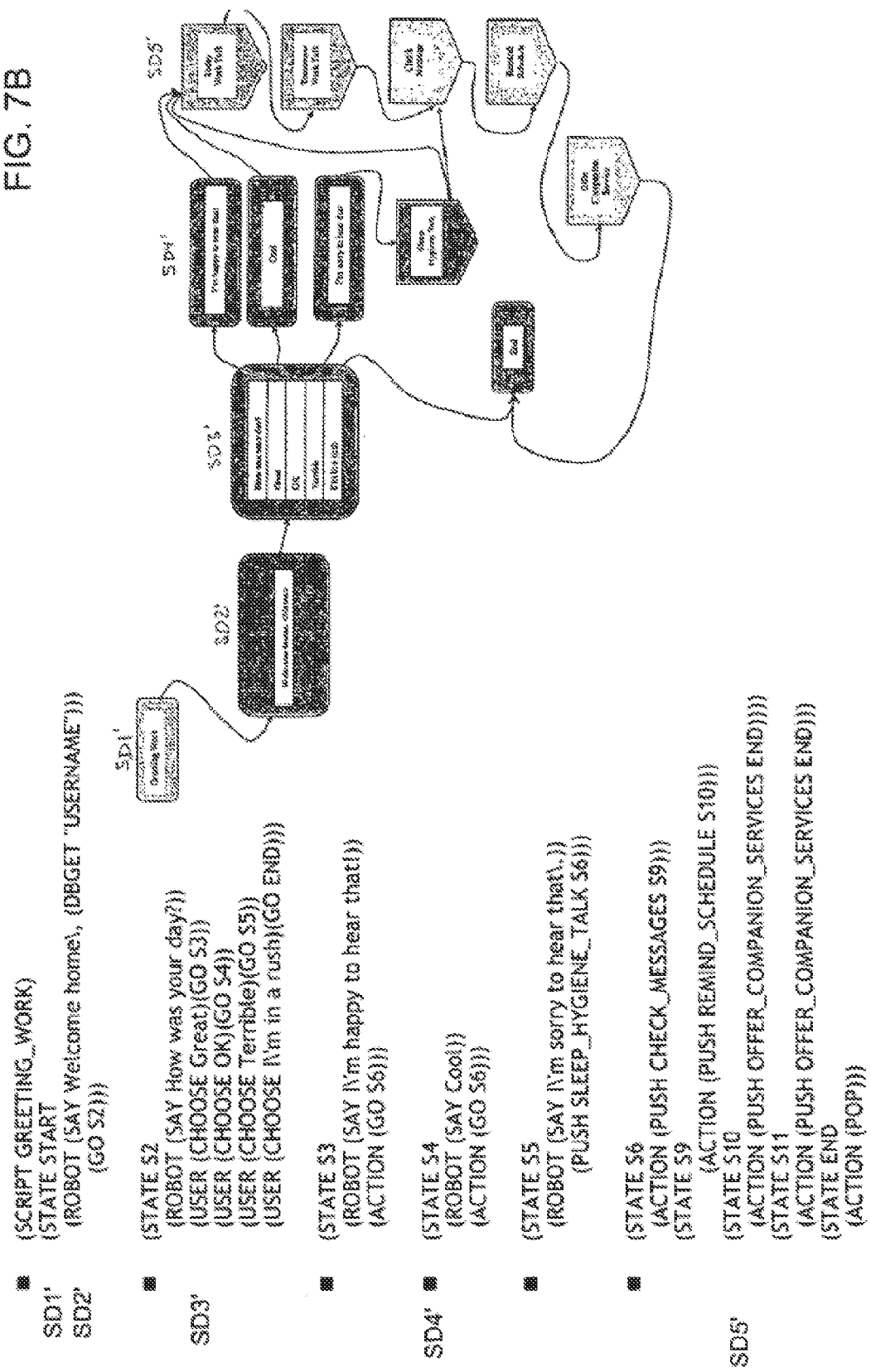

FIG. 7B

- SD1'  (SCRIPT GREETING_WORK)
- SD2'  (STATE START
         (ROBOT (SAY Welcome home\, (DBGET "USERNAME")))
         (GO S2)))

- SD3'  (STATE S2
         (ROBOT (SAY How was your day?))
         (USER (CHOOSE Great)(GO S3))
         (USER (CHOOSE OK)(GO S4))
         (USER (CHOOSE Terrible)(GO S5))
         (USER (CHOOSE I\'m in a rush)(GO END)))

(STATE S3
         (ROBOT (SAY I\'m happy to hear that))
         (ACTION (GO S6)))

- SD4'  (STATE S4
         (ROBOT (SAY Cool))
         (ACTION (GO S6)))

(STATE S5
         (ROBOT (SAY I\'m sorry to hear that\...))
         (PUSH SLEEP_HYGIENE_TALK S6)))

(STATE S6
         (ACTION (PUSH CHECK_MESSAGES S9)))
        (STATE S9
         (ACTION (PUSH REMIND_SCHEDULE S10)))

- SD5'  (STATE S10
         (ACTION (PUSH OFFER_COMPANION_SERVICES END)))
        (STATE S11
         (ACTION (PUSH OFFER_COMPANION_SERVICES END)))
        (STATE END
         (ACTION (POP)))

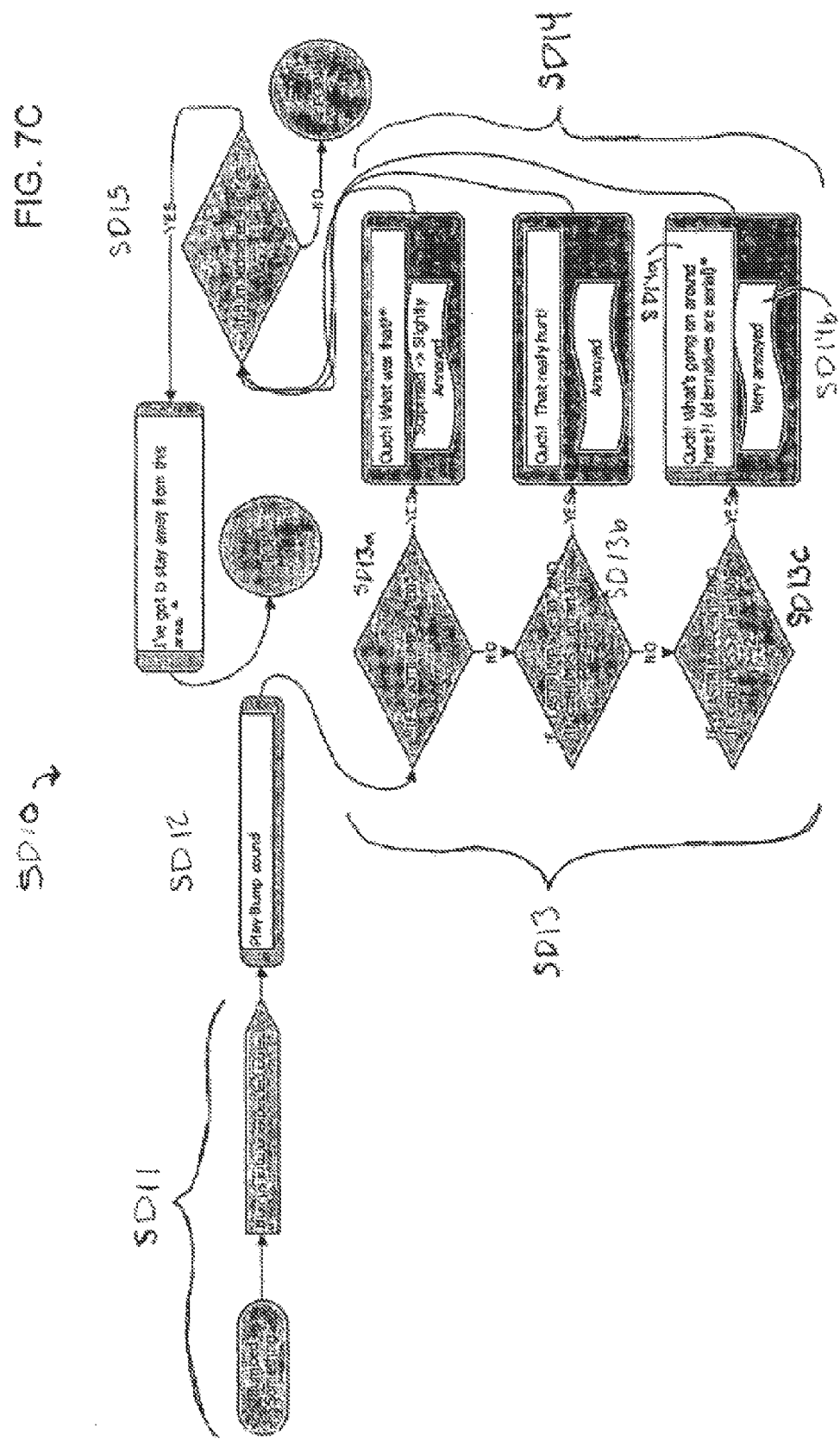

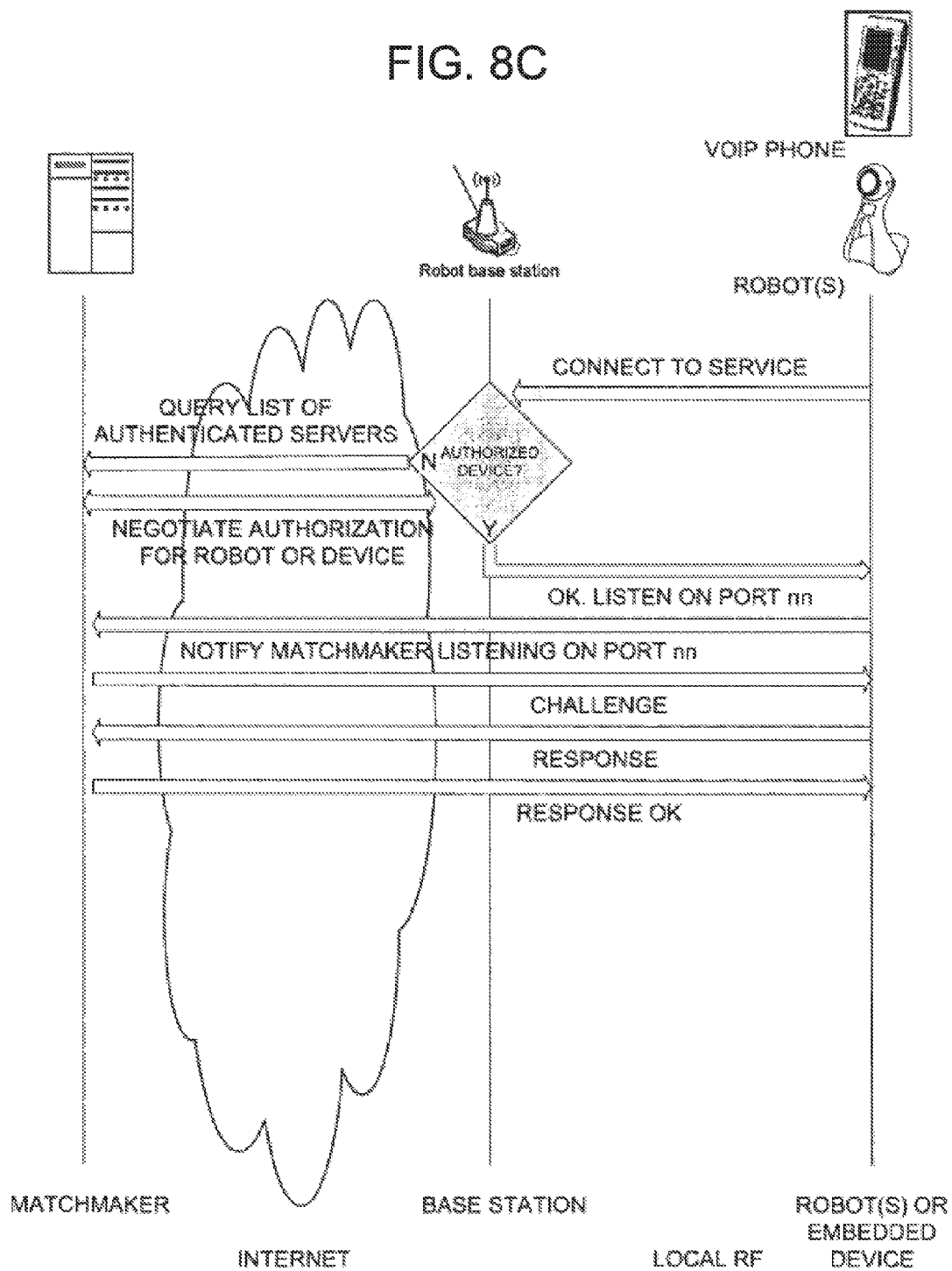

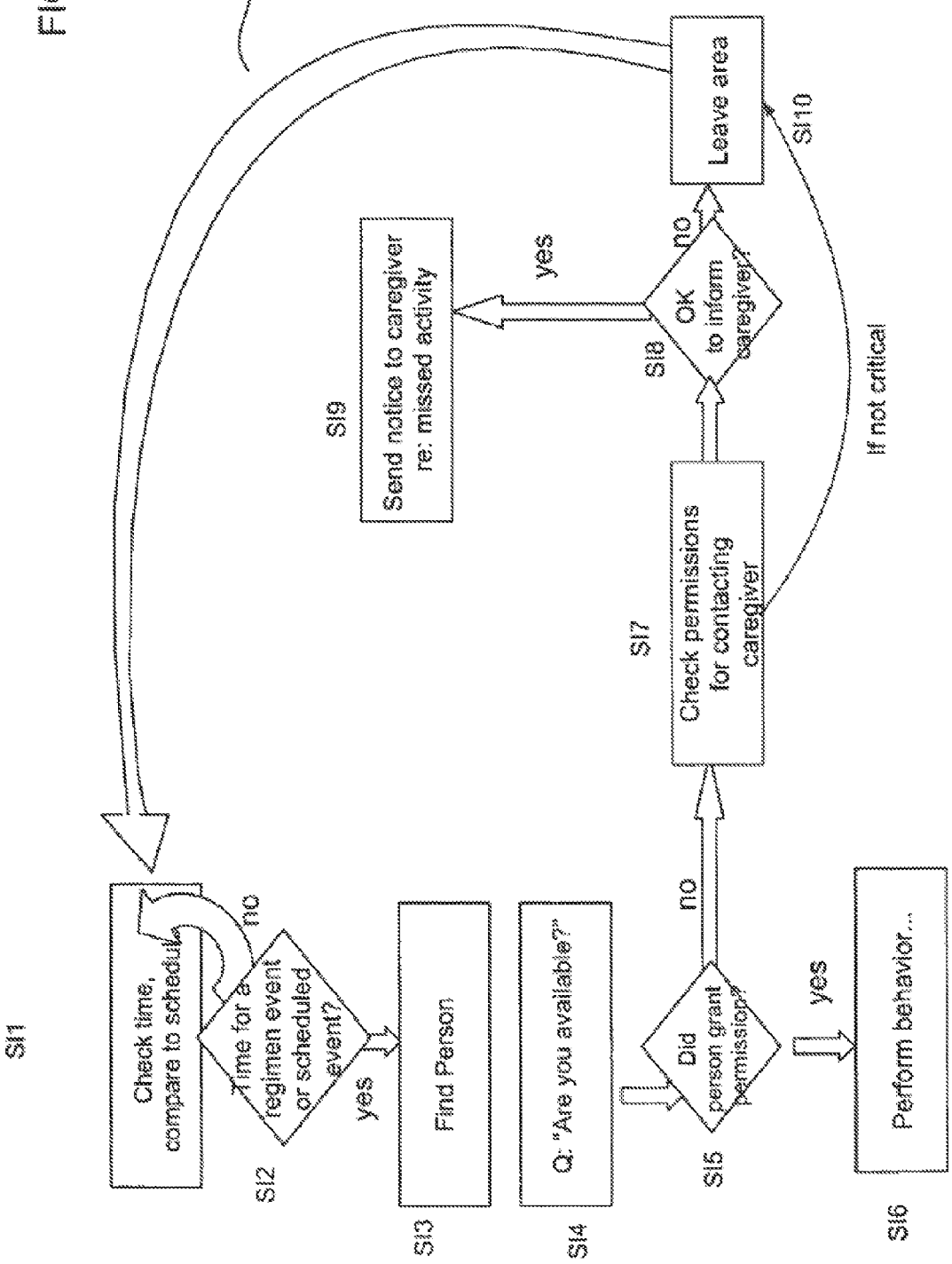

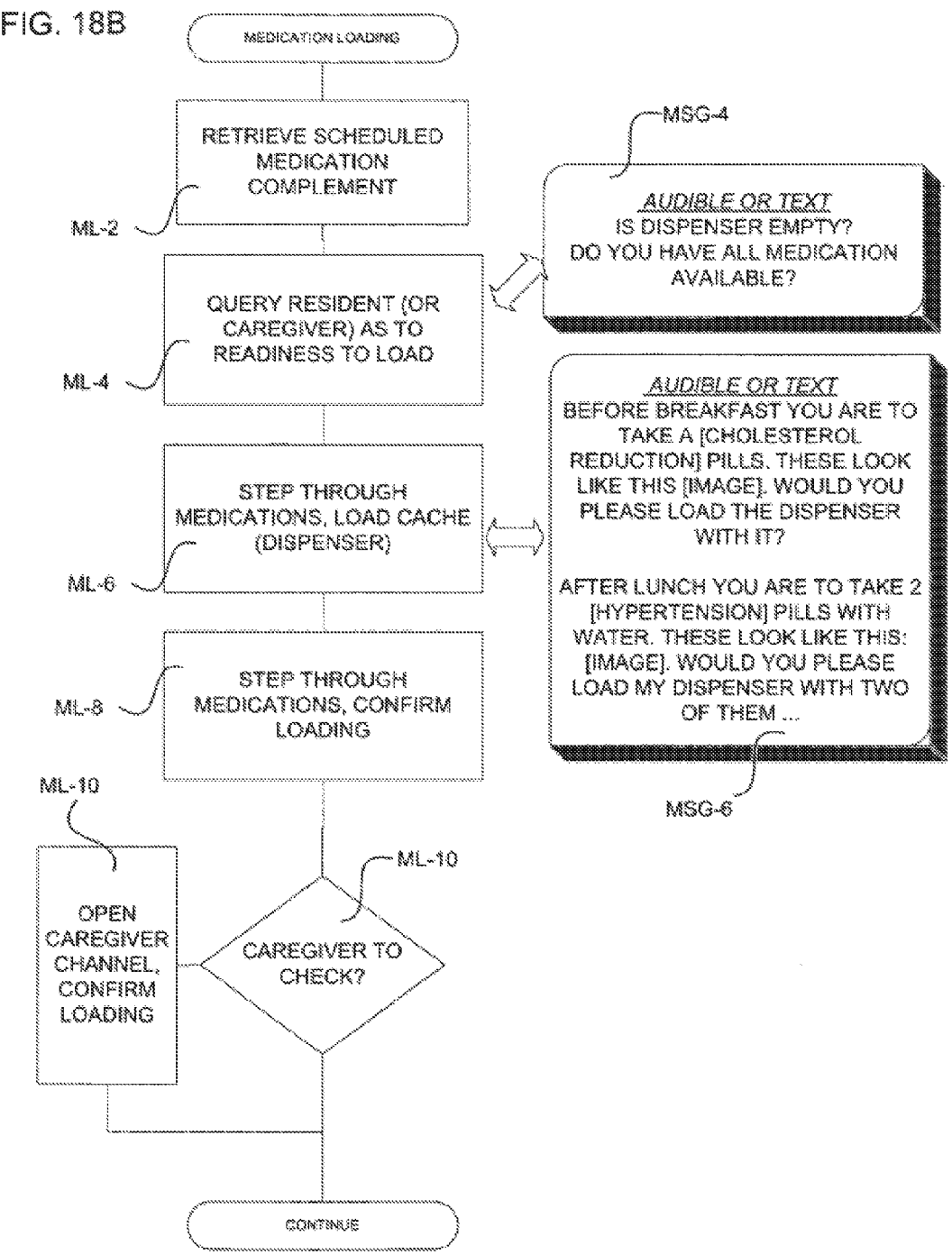

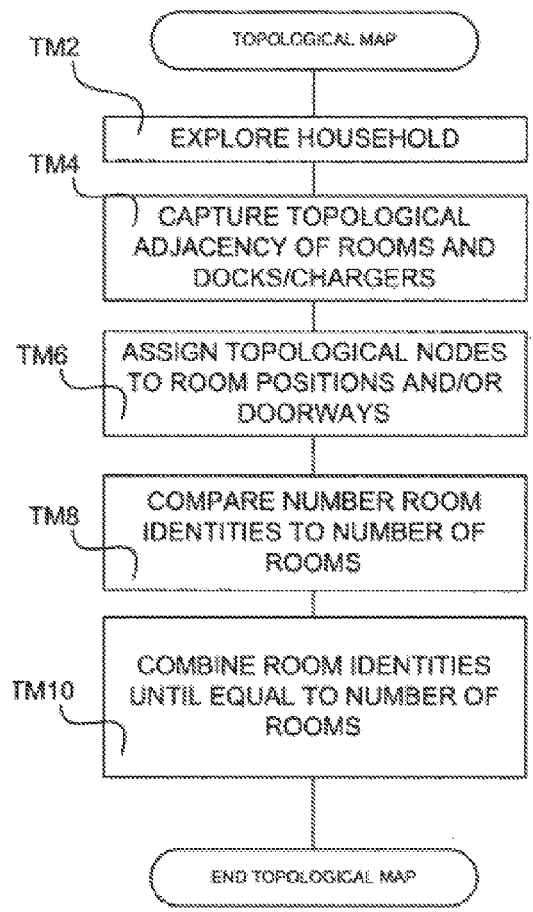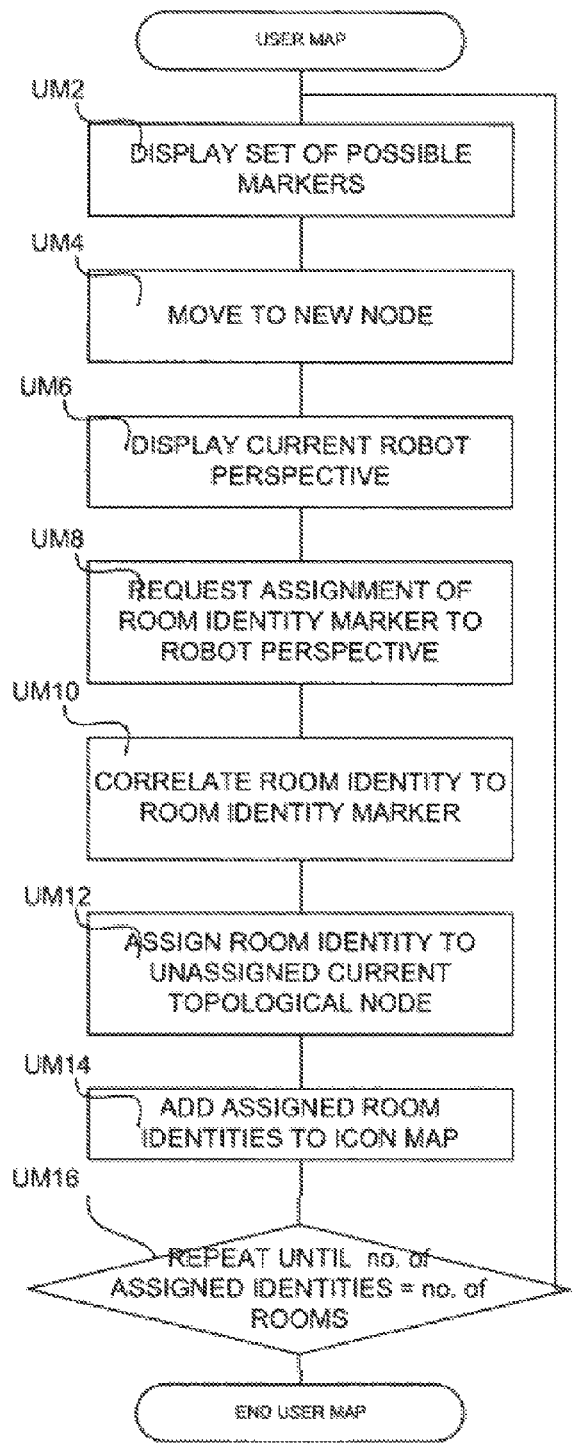

OPTION TO STEER, POSITION OR TRAVEL

COMPANION ROBOT FOR PERSONAL INTERACTION

CROSS REFERENCE TO RELATED APPLICATIONS

This U.S. patent application is a continuation of, and claims priority under 35 U.S.C. §120 from, U.S. patent application Ser. No. 11/541,422, filed on Sep. 29, 2006, which claims priority under 35 U.S.C. §119(e) to U.S. Provisional Patent Application 60/746,491, filed May 4, 2006; U.S. Provisional Patent Application 60/745,006, filed Apr. 17, 2006; and U.S. Provisional Patent Application 60/722,935, filed Sep. 30, 2005. The disclosures of these prior applications are considered part of the disclosure of this application and are hereby incorporated by reference in their entireties.

TECHNICAL FIELD

This disclosure relates to autonomous mobile robots for interacting with people and, more specifically, to autonomous mobile robots for assisting persons with various tasks.

BACKGROUND

Robotic research platforms have been developed for interacting with people in home situations, such as the elderly, children, or others who may benefit from an interactive robot assistant. These robotic platforms often do not consider the actual home environment, or personal preferences and concerns, such as making a companion robot non-intrusive and a welcome guest in the home environment.

Certain platforms have been developed which assist caregivers in carrying medications, providing amusing interaction, and/or providing teleconferencing tools, many remain research platforms: they tend to be so large, heavy, and unwieldy, as to be inappropriate for use in an ordinary home. These robotic platforms are generally tested in institutions, where some surveillance is expected and privacy and personal dignity tend already to be adversely affected, and may not be suitable for use in private homes, where expectations for privacy protection are higher.

Simply making a robot smaller, however, does not correct these shortcomings. Though a robot may be sufficiently small to be carried, the contemplated use is typically in a single room, with limited ability to be useful throughout an entire home. Low-weight platforms tend also to be low to the ground, and generally out of view of residents who may be moving about in the same rooms, creating a danger for those with balance or mobility issues. In short, previous robots suffer from limited usability, and thus do not function as a welcoming and versatile assistant to a human.

SUMMARY

In one aspect, the disclosure relates to a robot for regimen compliance management, including a processor, a memory accessible by the processor, a sensor capable of detecting a presence of a person within a detection range of the robot, a communication interface capable of generating a human-perceptible signal, a drive operatively connected to the processor that moves the robot, a scheduler routine executable on the processor that checks at least one of a medication dosage information for a medication event and a health-related information for a regimen event, and in advance of the event, initiates a person finding routine, a person finding routine executable on the processor that instructs the drive to move the robot about an environment and to stop in a position proximate a person, and a regimen compliance manager for ensuring compliance of a person with a regimen routine.

In one aspect, the disclosure relates to a robot for regimen compliance management, including a processor, a memory accessible by the processor that includes personal medication dosage information, a sensor capable of detecting the presence of a person within a detection range of the robot, a communication interface capable of generating a human-perceptible signal and receiving a compliance or non-compliance indication from the person, a drive operatively connected to the processor that moves the robot, a scheduler routine executable on the processor that checks the personal medication do sage information for medication events, and in advance of a medication event, initiates a person finding routine, a person finding routine executable on the processor that instructs the drive to move the robot about the household checking the sensor suite for the presence of the person and to stop in a position next to the person, a matching routine executable on the processor that sends a human perceptible signal to the person including information regarding the location of medication to be taken and guides the person to the medication. In certain embodiments of the above aspect, the communication interface is receiving a compliance or non-compliance indication from the person and the memory accessible by the processor includes postponement rules, and further including a regimen compliance snooze routine that upon recognition of a non-compliance indication from the person, checks the personal medication dosage information and sets a new medication event compatible with the postponement rules.

In another aspect, the disclosure relates to a robot for regimen compliance management, including a processor, a memory accessible by the processor that includes personal medication dosage information, the memory including postponement rules defining permissible conditions for postponing dosage, a sensor capable of detecting the presence of a person within a detection range of the robot, a communication interface capable of generating a human-perceptible signal and receiving a compliance or non-compliance indication from the person, a drive operatively connected to the processor that moves the robot, a scheduler routine executable on the processor that checks the personal medication dosage information for medication events, and in advance of a medication event, initiates a person finding routine, a person finding routine executable on the processor that instructs the drive to move the robot about the household and to stop in a position next to the person, a matching routine executable on the processor that sends a human perceptible signal to the person including information regarding medication to be taken, and a regimen compliance snooze routine that upon recognition of a non-compliance indication from the person, checks the personal medication dosage information and sets a new medication event if postponing medication is compatible with the postponement rules.

In yet another aspect, the disclosure relates to a robot for regimen compliance management, including a medication cache that receives loaded medication to be carried by the robot, a processor, a memory accessible by the processor that includes personal medication dosage information and postponing rules, a sensor capable of detecting the presence of a person within a detection range of the robot, a communication interface capable of generating a human-perceptible signal, a drive operatively connected to the processor that moves the robot, a scheduler routine executable on the processor that checks the personal medication dosage information for medication events, and in advance of a medication event, initiates a person finding routine, a person finding routine executable on the processor that instructs the drive to move the robot about the household checking the sensor suite for the presence of the person and to stop in a position next to the person, a matching routine executable on the processor that sends a human perceptible signal to the person including information regarding the medication carried in the medication cache. In certain embodiments of the above aspect, the robot includes a medication loading routine executable on the processor that sends a human perceptible signal to the person including information regarding loading the medication cache for later administration and information guiding the person to the medication.

In still another aspect, the disclosure relates to a robot system for regimen compliance management, having a medication cache that receives loaded medication, a processor, a memory accessible by the processor that includes personal medication dosage information and postponing rules, a sensor capable of detecting the presence of a person within a detection range of the robot, a communication interface capable of generating a human-perceptible signal, a drive operatively connected to the processor that moves the robot, a scheduler routine executable on the processor that checks the personal medication dosage information for medication events, and in advance of a medication event, initiates a person finding routine, a person finding routine executable on the processor that instructs the drive to move the robot about the household checking the sensor suite for the presence of the person and to stop in a position next to the person, and a medication loading routine executable on the processor that sends a human perceptible signal to the person including information regarding loading the medication cache for later administration, and information guiding the person to the medication cache.

In another aspect, the disclosure relates to a robot for regimen compliance management, including a network interface that connects the robot to a remote location at which a caregiver may connect to the robot, a processor, a memory accessible by the processor that includes personal medication dosage information, a sensor capable of detecting the presence of a person within a detection range of the robot, a communication interface capable of generating a human-perceptible signal and receiving a compliance or non-compliance indication from the person, a drive operatively connected to the processor that moves the robot, a scheduler routine executable on the processor that checks the personal medication dosage information for medication events, and in advance of a medication event, initiates a person finding routine, a person finding routine executable on the processor that instructs the drive to move the robot about the household checking the sensor suite for the presence of the person and to stop in a position next to the person, a regimen compliance reminder routine executable on the processor that, upon recognition of a non-compliance indication from the person, contacts the caregiver via the network interface. In certain embodiments of the above aspect, the robot includes an inbound communication channel for the caregiver to send a human-perceptible signal through the inbound communication channel and via the communication interface.

In yet another aspect, the disclosure relates to a robot for regimen compliance management, including a network interface that connects the robot to a remote location at which a caregiver may connect to the robot, a processor, a memory accessible by the processor that includes health-related regimen information, a sensor capable of detecting the presence of a person within a detection range of the robot, a communication interface capable of generating a human-perceptible signal, an inbound communication channel for the caregiver to send a human-perceptible signal through the inbound communication channel and via the communication interface, a drive operatively connected to the processor that moves the robot, a scheduler routine executable on the processor that checks the health-related regimen information for regimen events, and in advance of a health-related regimen event, initiates a person finding routine, a person finding routine executable on the processor that instructs the drive to move the robot about the household checking the sensor suite for the presence of the person and to stop in a position next to the person, and a regimen compliance guide access routine executable on the processor that connects a communication session with a caregiver via the network interface.

In another aspect, the disclosure relates to a method of human-robot interaction, including receiving a communication script segment, outputting to a person at least one of a visible component of the communication script segment and an audible component of the communication script segment, and controlling at least one of a robot expression component accompanying the output component and a robot response to an input by a person.

In still another aspect, the disclosure relates to a method of human-robot interaction, including receiving a communication script segment, including an output query sub-script text and a response tree of five or less sub-script response text candidate, associating the output query text with an audible output signal, and outputting the audible output signal as a spoken query to a person, displaying the output query sub-script text together with the five or less sub-script response text candidates on a display of the robot, receiving an audio input signal recording a person's response to the audible output signal, processing the audio input signal to recognize if the audio input signal includes speech corresponding to any one of the five or less displayed sub-script response text candidates, if the audio input signal is not recognized to include speech corresponding to any one of the four or less sub-script response text candidates, issuing an output signal to prompt the user to retry communicating a response to the audible output signal, and if the audio input signal is recognized to include speech corresponding to any one of the five or less sub-script response text candidates, issuing an output signal including a repetition of the one of the five or less sub-script response text candidates that was recognized. Embodiments of the above aspect include, after the confirmation signal is issued monitoring for a confirmation of the correctness or incorrectness of the one of the four or less sub-script response text candidates that was recognized. In still other embodiments issuing an output signal to prompt the user to retry communicating a response to the audio output signal includes, highlighting the displayed sub-script text on a display of the robot, and receiving an input signal selecting any one of the five or less displayed sub-script response text candidates via a manually operated control associated with the display. In additional embodiments two of the five or less sub-scripts response text candidates are a simple affirmative and simple negative response, and further include processing the audio input signal to recognize if the audio input signal includes speech corresponding to a family of affirmative responses equivalent to the simple affirmative response or includes speech corresponding to a family of affirmative responses equivalent to the simple negative response. In other embodiments one of the five or less sub-scripts response text candidates is a response text candidate that is common to a majority of communication script segments. In still other embodiments, no two of the five or less sub-scripts response text candidates are a simple affirmative and simple negative response, and further include processing the audio input signal to recognize if the audio input signal includes speech corresponding to a family of affirmative responses equivalent to the simple affirmative response or includes speech corresponding to a family of affirmative responses equivalent to the simple negative response. In other embodiments of the robot, the response tree is a response tree of three or less sub-script response text candidates, and none of the response text candidates is simple affirmative response or simple negative response. Other embodiments include converting the response tree text subscript into a set of menu choices displayed on the display.

In another aspect, the disclosure relates to a method of human-robot interaction, including receiving a communication script segment, including an output query sub-script text and a response tree of five or less sub-script response text candidate, associating the output query text with an audible output signal, and outputting the audible output signal as a spoken query to a person, displaying the output query sub-script text together with the five or less sub-script response text candidates on a display of the robot, receiving an audio input signal recording a person's response to the audible output signal, processing the audio input signal to recognize if the audio input signal includes speech corresponding to any one of the five or less displayed sub-script response text candidates, if the audio input signal is recognized to include speech corresponding to any one of the five or less sub-script response text candidates, issuing an output signal including a repetition of the one of the five or less sub-script response text candidates that was recognized if the audio input signal is not recognized to include speech corresponding to any one of the four or less sub-script response text candidates, highlighting the displayed sub-script text on a display of the robot, then receiving an input signal selecting any one of the five or less displayed sub-script response text candidates via a manually operated control associated with the display.

In yet another aspect, the disclosure relates to a method of human-robot interaction, including asynchronously executing a plurality of motion behaviors, including motion behaviors responsive to events, receiving a communication script segment, including dialogue branches with robot speech prompt text and human response text, interpreting the communication script segment to generate an audible robot speech prompt, receiving input from a person as a response to the audible robot speech prompt, interrupting a dialogue branch in response to an event detected by one of the plurality of behaviors to execute an asynchronous response, and recovering the dialogue branch after the execution of the asynchronous response.

In still another aspect, the disclosure relates to a method of human-robot interaction, including receiving a communication script segment, including dialogue branches with robot speech prompt text and human response text, associating the output query text with an audible output signal, and outputting the audible output signal as a spoken query to a person, modulating the dialogue branch to show a desired expression during the communication script segment by adding at least expression motion selected from a head movement sequence including nod axis head movement or turn axis head movement, or a robot movement sequence including movement of the entire robot.

In another aspect, the disclosure relates to a method of human-robot interaction, including receiving a communication script segment, including dialogue branches with robot speech prompt text, human response text, and robot expression motion tags, interpreting the communication script segment to generate an audible robot speech prompt and robot expression motions according to the dialogue branches, receiving input from a person as a response to the audible robot speech prompt, interrupting an expression motion in response to an event detected by the robot to execute a corrective behavior to reposition the robot according to the event, and recovering the dialogue branch after the execution of the corrective behavior.

In another aspect, the disclosure relates to a method of robot self-navigation for a robot, the method including monitoring at least one of a sensor and an input, comparing a signal from at least one of the sensor and the input to at least two predetermined conditions, and performing at least one of (a) an action, if the signal corresponds to a first condition; and (b) a movement of the robot, if the signal corresponds to a second condition.

In one aspect, the disclosure relates to a method of robot self-navigation, including monitoring a sensor capable of detecting the presence of a person within a detection range of the robot, improving a presence score when the person is detected within the detection range of the robot, decaying the presence score to progressively worsen, driving in a direction to move the robot to a different location when the presence score decays to a first threshold presence score, parking the robot in a location proximate to the person when the presence score improves to a second threshold presence score.

In another aspect, the disclosure relates to a method of robot self-navigation, including monitoring a sensor capable of detecting the presence of a detectable object within a detection range of the robot, improving a presence score when a detectable object is detected within the detection range of the robot, decaying the presence score to progressively worsen, driving in a direction to move the robot to a different location when the presence score decays to a first threshold presence score. In certain embodiments, the sensor suite is capable of detecting detectable objects including a person and a charging station, and the method further includes parking the robot in a charging station located proximate to the person, engaged to recharge, when the presence score improves to a second threshold presence score. In other embodiments, the driving includes moving the robot to a succession of different locations until the presence score improves to a second threshold presence score.

In yet another aspect, the disclosure relates to a method of robot self-navigation, including monitoring a sensor suite capable of detecting the presence of a detectable object within a detection range of the robot, detectable objects including either or both of a person and a charging station, improving a presence score when a detectable object is detected within the detection range of the robot, decaying the presence score to progressively worsen, driving in a direction to move the robot to a different location when the presence score decays to a first threshold presence score, and parking the robot in a charging station located proximate to the different location and to the person, engaged to recharge, when the presence score improves to a second threshold presence score.

In another aspect, the disclosure relates to a mobile robot for interacting with a person, including a first detector for detecting at least one of a person and an object within a first predetermined space proximate the robot, a second detector for detecting at least one of a person and an object within a second predetermined space proximate the robot, a physical contact device to detect contact between at least one of a person and an object, wherein at least one of the first detector, the second detector, and the contact device triggers a safety condition, and a controller configured to immobilize the robot when the safety condition is detected.

In still another aspect, the disclosure relates to a method of robot self-navigation, including generating an annunciator activation signal in response to a detected condition, activating an annunciator upon an annunciator activation signal, monitoring a sensor for a detected response from a person, checking whether the detected response includes a sought response, if the checking confirms the detected response includes a sought response, activating a found person success routine, and if the checking confirms the detected response includes a sought response, identifying a passage from a present chamber, and driving in a direction to move the robot through the passage from the present chamber to a new chamber.

It is a preferably a function of the robot to act as a confidence, trust, and bonding manager. The robot is crafted to boost user trust and emotional attachment, which is beneficial in itself and provides generic benefits for any and all other applications, increasing their success rate. This function addresses the challenge of introducing new and unfamiliar technology (especially autonomous, self-controlled, mobile technology) into the lives of ordinary persons.

In another aspect, the disclosure relates to a method for robotically locating a person being sought, including monitoring a sensor suite for a non-noise signal indicative of the presence of a person, and if the non-noise signal corresponds to a sought response, then activating a found person success routine, and if the non-noise signal does not correspond to a sought response or if no response is identified, then selecting one of (i) identifying a doorway from a present chamber, and navigating the robot through the doorway from the present chamber to a new chamber, or (ii) controlling a mobile robot to activate an annunciator. In certain embodiments of the above-aspect, the annunciator emits a sound including the name of the person being sought, and the method further includes checking the sought response to confirm that the source of the sought response is a person of the name being sought.

In yet another aspect, the disclosure relates to a method for navigating a robot, including receiving a first navigation command representative of a remote user's selection of a room identity marker, recognizing a present room, driving among rooms of different room identity according to the first navigation command until the robot recognizes being within a room having a room identity corresponding to the selected room identity marker, receiving a second navigation command representative of a remote user's selection of one of a floor location within the room having a room identity corresponding to the room identity marker or a landmark item within the room having a room identity corresponding to the room identity marker, driving within the room corresponding to the room identity according to the second navigation command until the robot recognizes being at one of the floor location or next to the landmark item, receiving a third navigation command stream representative of a remote user's command including direction and bearing, driving within the room and from the floor location according to the received third navigation command stream representative of a remote user's command including direction and bearing.

In still another aspect, the disclosure relates to a method for handling navigation commands for remotely controlling a robot, including receiving a selection of room identities corresponding to available room identities in a household, driving among rooms of different room identity until the robot captures topological adjacency among room identities and correlates each room identity of a household with a received room identity marker, displaying room identity markers corresponding to available room identities for a household, the room identity markers being displayed according to topological adjacency of corresponding room identities and being displayed as a part of a graphical depiction of a house.

In another aspect, the disclosure relates to a method for handling navigation commands for remotely controlling a robot, including receiving a selection of room identities corresponding to available room identities in a household, driving among rooms of different room identity until the robot captures topological adjacency among room identities and correlates each room identity of a household with a received room identity marker, displaying room identity markers corresponding to available room identities for a household, the room identity markers being displayed according to topological adjacency of corresponding room identities and being displayed as apart of a graphical depiction of a house, receiving a selection of a room identity marker via a user interface linked to the displaying room identity markers as a first navigation command representative of a remote user's selection of a room identity marker, recognizing a present room, and driving among rooms of different room identity according to the first navigation command until the robot recognizes being within a room having a room identity corresponding to the selected room identity marker.

In yet another aspect, the disclosure relates to a mobile robot for interacting with a person, including an annunciator configured to audibly indicate the presence of the robot, a visible beacon configured to optically indicate the presence of the robot, a proximity curtain detector configured to detect a person within a curtain covering a majority of the height of the robot and thereafter trigger a safety condition, a physical impact buffer configured to absorb impact of a person colliding with the robot, detect the person, and trigger the safety condition, a floor-level proximity ribbon detector configured to detect objects of less than 2 inches in height and trigger the safety condition, and a controller configured to immobilize the robot when the safety condition is detected.

In stilt another aspect, the disclosure relates to a mobile robot for interacting with a person, including a zone detector configured to detect an object within a zone in front of the robot covering a substantial portion of the height of the robot above 10 inches from the ground and thereafter trigger a safety condition, a near zone impact bumper configured to absorb an impact of an object colliding with the robot, detect the object, and trigger the safety condition, a near zone proximity sensor configured to detect an object in front of the robot between 2-10 inches from the ground and trigger the safety condition, a near zone low object proximity sensor configured to detect objects in front of the robot of less than 2-4 inches in height and trigger the safety condition, and a controller configured to immobilize the robot when the safety condition is detected. In embodiments of the above aspect, each of the proximity curtain detector, the physical impact buffer, and the floor-level proximity ribbon detector are configured to detect a person at different distances from a center of the robot. In certain embodiments, the robot further includes a heat radiation detector or sound detector checked by the controller, that determines that an object encountered in the direction of travel is a person when heat radiation or sound of an object is above a low threshold and optionally below a high threshold. In other embodiments, the robot is configured to stow to less than 10 cm/sec when an object in the direction of travel is determined to be a person by heat radiation or sound detection.

In another aspect, the disclosure relates to a robot for interacting with a resident in an environment, including a sensor adapted to monitor a resident when the robot is in an environment and a resident is within range of the sensor, a controller to monitor surveillance data from the sensor, a transmission control routine configured to enable transmission of surveillance data from the sensor to a location outside an environment, if a resident grants permission for the transmission, and an override routine configured to enable transmission of surveillance data from the sensor to a location outside the environment at least in an emergency condition.

In another aspect, the disclosure relates to a robot for interacting with a resident in the resident's home, including a sensor capable of monitoring the resident when the robot is in the resident's home and the resident is within range of the sensor, a controller connected to monitor surveillance data from the sensor, a transmission control routine configured to enable a transmission of surveillance data from the sensor outside the resident's home if the resident grants permission for the transmission, and an override routine configured to enable a transmission of surveillance data from the sensor outside the resident's home (i) in an emergency condition detected by the robot or (ii) after an authorized remote caregiver sends to the robot an authorization previously permitted by the resident and an emergency condition indication, wherein the transmission of surveillance data by the robot outside the resident's home is otherwise prohibited. In certain embodiments of the above aspect, the robot includes a connector capable of receiving a lock-out member, wherein the transmission control routine enables transmission of surveillance data from the sensor outside the resident's home only when the lock-out member is inserted in the connector. In other embodiments, the sensor includes a camera, and the robot includes a privacy controller configured to orient the objective lens of the camera to face the robot's body when a privacy mode is selected. In alternative embodiments, the robot includes a privacy member configured to physically unplug the sensor when a privacy mode is selected.

In yet another aspect, the disclosure relates to a robot for interacting with a resident in the resident's home, including a sensor capable of monitoring the resident when the robot is in the resident's home and the resident is within range of the sensor, a controller connected to monitor surveillance data from the sensor, a connector capable of receiving a lock-out member, a transmission control routine configured to enable transmission of surveillance data from the sensor outside the resident's home if the resident grants permission for the transmission and only when the lock-out member is inserted in the connector, and an override routine configured to enable transmission of surveillance data from the sensor outside the resident's home only when an emergency condition signal is received by the robot.

In another embodiment, the disclosure relates to a robot capable of human-robot interaction, including a head assembly including a face at least one camera mounted proximate the face, and a positionable support having a first position and a second position, the mount supporting at least one of the face and the at least one camera.

In still another aspect, the disclosure relates to a robot capable of human-robot interaction, including a head assembly including a head having a face on one side, at least one camera mounted within the face to direct an objective lens of the camera in the same direction as the face, a rotatable pivot supporting the head to permit the head to move such that the face and the at least one camera are hidden from view and the camera is thereby prevented from viewing an area around the robot. In embodiments of the above aspect, the face further includes a matrix panel electronically controllable to show different configurations of left and right eyes composed of matrix elements, and the at least one camera includes a left camera proximate to the left eye composed of matrix elements and a right camera proximate to the right camera composed of matrix elements.

In another aspect, the disclosure relates to a robot capable of human-robot interaction, including a head assembly including a head having a face on one side, the face comprising a matrix panel electronically controllable to show different configurations of left and right eyes composed of matrix elements, a left camera proximate to the left eye and a right camera proximate to the right eye, each of left and right cameras being mounted near the face to direct an objective lens of the camera in the same direction as the face, and at least one positionable mount supporting the left camera and right camera to each move to a position disabled from viewing an area around the robot.

In yet another aspect, the disclosure relates to a robot system, including abuse station, and a robot, the base station including a wireless transceiver capable of communicating TCP/IP transmissions over a local wireless protocol, a wired Ethernet connector for communicating TCP/IP transmissions over a local wired Ethernet accessing the Internet, and an access point circuit for transferring TCP/IP transmissions between the local wired Ethernet and local wireless protocol limited to a predetermined IP address locked to the robot, predetermined shell level encryption locked to the robot, and predetermined ports to the Internet open only to the robot, the robot including a wireless transceiver capable of communicating TCP/IP transmissions over a local wireless protocol and a client circuit for transferring TCP/IP transmissions over the local wireless protocol. In embodiments of the above aspect, the wireless access point includes a plurality of antennas and an antenna diversity circuit. In other embodiments, the wireless access point includes a plurality of antennas and an antenna diversity circuit and encodes wireless transmissions using orthogonal frequency division multiplexing.

In accordance with an embodiment of the present disclosure, a method for robotically locating a person being sought may include (a) controlling a mobile robot to activate an annunciator upon an annunciator activation signal, (b) monitoring a sensor suite for any non-noise (noise filtered) response to the annunciator within a limited time period after the activation, (c) comparing any detected non-noise response to a library of sought responses; (d) when the non-noise response does not correspond to a sought response or when no response is identified, identifying a doorway from a present chamber; (e) navigating the robot through the doorway from the present chamber to a new chamber; (f) generating an annunciator activation signal in response to a detected condition, and (g) repeating (a) through (f) until the non-noise response corresponds to a sought response, then (h) activating a found person success routine.

The identifying the doorway may include analyzing robot odometry and heading during wall following and identifying successive odometry/heading combinations indicating a wall end and/or doorway has been traversed. Also, the identifying the doorway may include analyzing robot signal reflection sensing and identifying a heading toward a wall gap. The identifying the doorway may further include analyzing a dynamically built map and identifying a heading toward a wall gap; analyzing an archived map and robot position and identifying a heading toward a wall gap; analyzing a beacon sensor of a door-designating beacon and identifying a heading toward a door designated by the door beacon; and/or analyzing a ceiling configuration or pattern of indicia on a ceiling of a present chamber and identifying a heading toward a door at a position recognized using the indicia or ceiling configuration.

The annunciator may emit a sound including the name of the person being sought, and the comparing any detected non-noise response to the library of sought responses/non-noise response indicates that the source of the non-noise response is a person being sought. The method may further include selecting the second location based on an arbitrary heading and an arbitrary distance for the mobile robot to travel; adjusting the heading of the mobile robot when an obstacle or hazard is encountered; and proceeding until the mobile robot has traveled the arbitrary distance. The new chamber may lie in a different room from the present chamber, and the method may further include navigating the mobile robot from the present chamber location to the new chamber based on one or more of optical room feature recognition, sonar, RFID room tagging, IR directional beacon detection, odometry, inertial guidance, dead reckoning, room mapping, and/or compass navigation.

The method may also include using at least one secondary detection system configured to detect the person being sought, in which the at least one secondary detection system is selected from infrared detection, radiative heat detection, acoustic detection, RFID tag detection, tank circuit detection, motion detection, and/or image analysis; or, the method may further include generating a map of a structure in which the mobile robot is located, and selecting the new chamber based on the generated map, in which the new chamber is in a different room from the present chamber or lies at least a threshold distance away from the present chamber.

The generating the map may include controlling the mobile robot to traverse the robot's environment and to detect walls and obstacles; and the map may be transmitted to the mobile robot by a user. The method may further include locating a closed door, and transmitting an audible signal through the door; in addition, the transmitting the audible signal may include imparting a knocking sound to the closed door.

In accordance with one embodiment, a mobile robot for interacting with a person may include a speaker for generating audible content based on a robot behavior; a scheduler configured to trigger a robot behavior in accordance with the schedule; and a morning robot behavior for interacting with the person soon after the person awakens regarding a second robot behavior scheduled later in the day. The robot may also include a pill dispenser for dispensing medication, in which the second robot behavior includes dispensing medication to the person, and in which the morning robot behavior includes reminding the person about the medication and/or requesting that a person place the medication into the pill dispenser. The robot may further include a transmitter for notifying a caregiver when the medication is not dispensed according to schedule.

Also, the robot may further include a sensor for detecting the person; a locator which uses the sensor when locating the person, in which the robot attempts to locate a person prior to the scheduled robot behavior. Further, each robot behavior may include using the speaker to remind the person of a scheduled robot behavior. The second robot behavior may include guiding the person 2 a predetermined location, in which the morning robot behavior includes verbally reminding the person of an activity associate with the upcoming second robot behavior; and the morning robot behavior may cognitively reinforce the person's recollection regarding an activity associated with the later second robot behavior.

The mobile robot may further include a visual display, in which at least one of the morning or second robot behaviors include both displaying and speaking. The mobile robot may further include a privacy controller for preventing transmission to a caregiver unless the person has given permission to notify the caregiver. Also, the robot may include a receiver for receiving the command from the caretaker, in which the privacy controller is overridden when the command is received.

At least one of the robot behaviors may be input by the person or by the caregiver; and the mobile robot may cease interaction with the person when instructed to stop by the person or by the caregiver.

In accordance with another embodiment, the mobile robot for interacting with a person may include at least one sensor; a privacy controller for preventing operation of the sensor unless the person grants permission for the sensor to operate; and an override unit configured for enabling operation of the sensor regardless of the privacy controller when the override unit receives an override command. Regarding the mobile robot, the sensor may include at least one of a camera, a microphone, a proximity detector, a heat detector, or a tag detector. The mobile robot may further include a wireless transmitter for transmitting and output of the sensor, or a recording unit configured to record the output of the sensor. The mobile robot may also include a teleconferencing unit for transmitting and receiving audio and/or video data, in which the teleconferencing unit includes the sensor, and in which the privacy controller prevents initiation of a teleconferencing session unless the person grants permission. In addition the mobile robot may further include a speech recognition unit for detecting spoken input, in which the permission to talk with the sensor and the input by the speech recognition unit. The mobile robot 1 may control or manipulate an object in the household of the person (for example, turning on a television at a certain time by using an on-board IR transmitter), or point to an object or location at a certain time of day, as components of robot operation.

Also, the override unit may include a receiver for wirelessly receiving the override command from a remote caregiver. The mobile robot may attempt to locate the person when an incoming teleconferencing request is received. Also, the privacy controller may be overridden when the robot detects an emergency condition—for example, if a person appears to be passed out, in danger, sick, or if there's smoke or if a fire alarm has been triggered, etc. The sensor may be conspicuously positioned when operating, and the sensor may become shrouded, covered, or moved so as not to be seen by the person when the sensor is not operating. Furthermore, the sensor may include a camera, in which the camera is placed in an inoperable position when permission to operate is not granted, and in which a lens of the camera faces an opaque surface in the inoperable position.

The mobile robot may further include a behavior privacy matrix stored in a computer memory and correlating a plurality of robot behaviors to a plurality of permission to scores, in which the privacy controller permits a robot behavior when the robot behavior has been permitted, or prevents the robot behavior when the robot behavior has not been permitted.

In accordance with yet another embodiment, a robot for interacting with a person may include an annunciator for audibly indicating the presence of the robot; a beacon for optically indicating the presence of the robot; a sensor for detecting a safety condition; and a controller for immobilizing the robot when the safety condition is detected. The annunciator may continuously or periodically emit a characteristic sound when the robot is moving. The beacon may shine a strobe light when the robot is moving, as well. Also, the sensor may include a camera, an optical sensor, an IR sensor, a key detector, a motion detector, a contact switch, a pressure detector, a proximity sensor, a sonar, a laser based obstacle detector, a noise detector, and/or a microphone, inter alia.

The mobile robot may further include a platform mounted to main chassis of the robot by a stalk, in which the platform and the stalk convey an impression of fragility, and in which the platform extends to the person's waist-level above the main chassis of the robot. The stalk and robot may have an overall shape and/or mass distribution similar to an inverted pendulum. The mobile robot may further include a tipper ring positioned along the stalk which prevents the person from inadvertently colliding with the platform.

The mobile robot may also include a communication unit for sending information regarding the person 2 a remote terminal operable by a caregiver. The communication unit may not send the information if the person has not given permission, and in addition, it may periodically transmit the information according to a predetermined schedule. Also, the communication unit may send the information when the information has changed. Alternatively, for example, the communication unit may retrieve instructions via a computer network.

In another aspect, the disclosure relates to a method of human-robot interaction between a resident and a mobile robot, the method including the steps of providing a robot comprising a facial display and a sound generating device, executing a viseme sequence of a communication script segment via the display, executing a phoneme sequence of the communication script segment via the sound generating device, wherein the viseme sequence and the phoneme sequence are executed substantially synchronously, and managing the interaction based at least upon an action of the resident and a flexible response regimen of the robot. In one embodiment of the above aspect, the managing step includes an affect behavior for depicting a response of the robot to an event. The affect behavior may include the steps of providing the display on a movable head on the robot, and moving the head from a first position to a second position upon an occurrence of an event. In the above method, the first position may permit viewing by the resident, and the second position is associated with at least one of a surprise response, a joy response, a confusion response, a concern response, and a dejection response. The affect behavior further may include the step of displaying a caricature. The caricature is selected from a set of caricatures associated with a surprise response, a joy response, a confusion response, a concern response, and a dejection response.

In another embodiment of the above aspect, the managing step includes an interrupt behavior for responding to an asynchronous response by the resident. The interrupt behavior may include the steps of receiving the asynchronous response, interrupting the execution of the viseme sequence and the execution of the phoneme sequence upon receipt of the asynchronous response, executing an interrupt sequence, and recovering the execution of the viseme sequence and the execution of the phoneme sequence subsequent to the interrupt sequence. The interrupt behavior may include delivering an error message. Delivering the error message may include the steps of executing an error viseme sequence via the display, and executing an error phoneme sequence via the sound generating device, wherein the execution of the error viseme sequence and the execution of the error phoneme sequence are substantially synchronized. The recovering step may include the step of repeating the steps of executing the viseme sequence and executing the phoneme sequence. The asynchronous may not correspond to at least one of a predetermined set of responses. The above method may also include the steps of comparing a response to the predetermined set of responses, and executing a second viseme sequence and a second phoneme sequence, if the response corresponds to at least one response of the predetermined set of responses.

In another embodiment of the above aspect, the managing step may include a regimen compliance behavior for providing instruction to the resident. The regimen compliance behavior includes the steps of storing a regimen and a compliance schedule associated with the regimen, providing a reminder to the resident at a predetermined event during the compliance schedule, comparing a response from the resident to a set of predetermined responses, and performing an action based on the response from the resident. In another embodiment, the performing step includes providing a medicine to the resident. In another embodiment, the performing step includes providing a second reminder to the resident. The performing step may include communicating with a device remote from the robot.

In another embodiment of the above aspect, the managing step may include a remote communication sequence for communicating between the resident and a third party located remote from the resident. In another embodiment, the remote communication sequence includes the steps of providing a camera on the robot, and changing a status of the camera from a first setting to a second setting upon an occurrence of an event. The first setting may permits viewing the resident, and the second setting may include a privacy orientation of the camera. The method may also include the step of providing a privacy signal to the resident. The event may include a permission denial from the resident. The first setting includes an unpowered condition of the camera, and the second setting includes a powered condition of the camera, and wherein the camera is oriented for viewing the resident.

In still another embodiment of the above-aspect, the managing step includes a navigation manager for moving the mobile robot in an environment. The navigation manager includes a human-seeking sequence, the sequence including the steps of activating an annunciator in a first of a plurality of locations, monitoring a sensor suite for a non-noise response, comparing the non-noise response to a set of predetermined responses, activating a success routine if the non-noise response corresponds to at least one response of the set of predetermined responses, navigating the robot to a next location, and activating the annunciator. The navigating step includes the step of identifying a doorway, which includes at least one of the group of (a) analyzing robot odometry and heading during a wall following mode and identifying odometry and heading combinations indicating traversal of at least one of a wall end and a doorway, (b) analyzing signal reflection and identifying a heading toward a wall gap, (c) analyzing a dynamically built map and identifying a heading toward a wall gap, (d) analyzing a map and robot orientation relative to the map and identifying a heading toward a wall gap, (e) analyzing a beacon and identifying a heading toward the beacon, and (f) analyzing a pattern of indicia on a ceiling and identifying a heading toward a door at a position recognized by utilizing the pattern. In the method, the annunciator emits a sound including a name associated with the resident being sought, and wherein the set of predetermined responses identifies a source of the non-noise response. The method may also include the steps of selecting the next location based on an arbitrary heading and an arbitrary distance for the mobile robot to travel, moving in the direction of the arbitrary heading, adjusting a direction of travel of the mobile robot to avoid an obstacle, returning to the arbitrary heading when the obstacle is avoided, and continuing movement in the direction of the arbitrary heading until the mobile robot has traveled the arbitrary distance. Additionally, the method may further include the step of navigating the mobile robot to the next location based on at least one of optical room feature recognition, sonar, RFID room tagging, IR directional beacon detection, odometry, inertial guidance, dead reckoning, room mapping, and compass navigation. The method may also include the step of using at least one detector configured to detect a person, wherein the at least one detector is selected from the group consisting of an infrared detector, a radiation detector, and acoustic detector, an RFID detector, a tank circuit detector, a motion detector, and an image detector. In addition, the method further includes the steps of generating a map of a structure in which the mobile robot is located, and selecting the next location based on the generated map, wherein the next location is located at least a threshold distance away from a present location of the mobile robot. The generating step includes detecting obstacles or receiving the map electronically from a resident. The method may also include the steps of locating a closed door, and transmitting an audible signal through the door. The transmitting step includes imparting a knocking sound to the door.

In yet another embodiment of the above aspect, the managing step includes a safety manager for controlling contact with a resident. The safety manager initiates a safety sequence including the steps of configuring an annunciator to indicate a presence of the robot, configuring a beacon to indicate the presence of the robot, configuring a sensor to detect a safety condition, and configuring a controller to immobilize the robot when the safety condition is detected. The annunciator emits a predetermined sound when the robot is moving. The beacon comprises a strobe light. The sensor includes at least one of a camera, an optical sensor, an IR sensor, a key detector, a motion detector, a contact switch, a pressure detector, a proximity sensor, a sonar detector, a laser-based obstacle detector, a noise detector, and a microphone. The above method further includes the step of configuring physical shape of the robot to limit contact between the resident and a base of the robot. The above method further includes the step of configuring a communication unit for sending information regarding the resident to a remote terminal. Sending information includes receiving permission from the resident, which is sent according to a predetermined schedule, upon an occurrence of a change in information, or is exchanged with a computer.

The details of one or more implementations of the disclosure are set forth in the accompanying drawings and the description below. Other aspects, features, and advantages will be apparent from the description and drawings, and from the claims.

DESCRIPTION OF DRAWINGS

FIG. 2 is a schematic perspective view of a mobile robot and functions thereof in accordance with another embodiment of the present disclosure;

FIGS. 3A-3C are schematic front views and perspective views of mobile robots and medicine dispensers and base stations in accordance with other embodiments of the present disclosure;

FIG. 4A is a schematic bottom view of a mobile robot in accordance with an embodiment of the present disclosure;

FIG. 4B is schematic top, side, and front views of a mobile robot in accordance with another embodiment of the present disclosure;

FIGS. 5A-5B are schematic perspective views of the mobile robot of FIG. 1A;

FIG. 7B depicts a dialog algorithm in accordance with one embodiment of the present disclosure;

FIG. 7C depicts a bump algorithm in accordance with one embodiment of the present disclosure;

FIG. 8C depicts a schematic diagram of authentication and negotiation for NAT/firewall traversing connectivity in accordance with one embodiment of the present disclosure;

FIG. 11B depicts a regimen initiation algorithm in accordance with one embodiment of the present disclosure;

FIG. 18B depicts a medication loading algorithm in accordance with one embodiment of the present disclosure;

FIGS. 21A-21B depict map generation algorithms in accordance with embodiments of the present disclosure;

Like reference symbols in the various drawings indicate like elements.

DETAILED DESCRIPTION

Figure 1A:
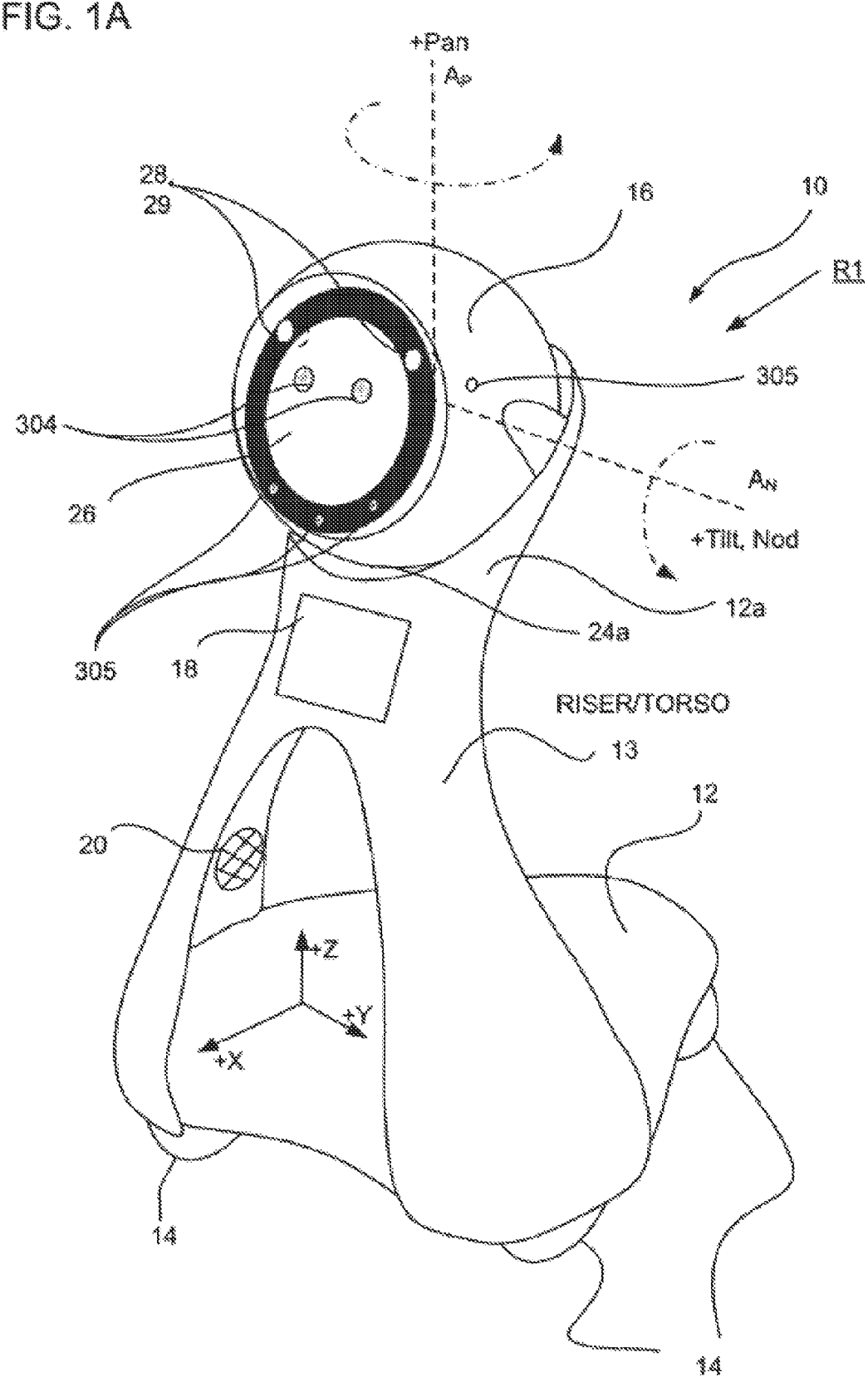
FIG. 1A is a schematic perspective view of an autonomous mobile robot in accordance with one embodiment of the present disclosure.
Figure 1B:
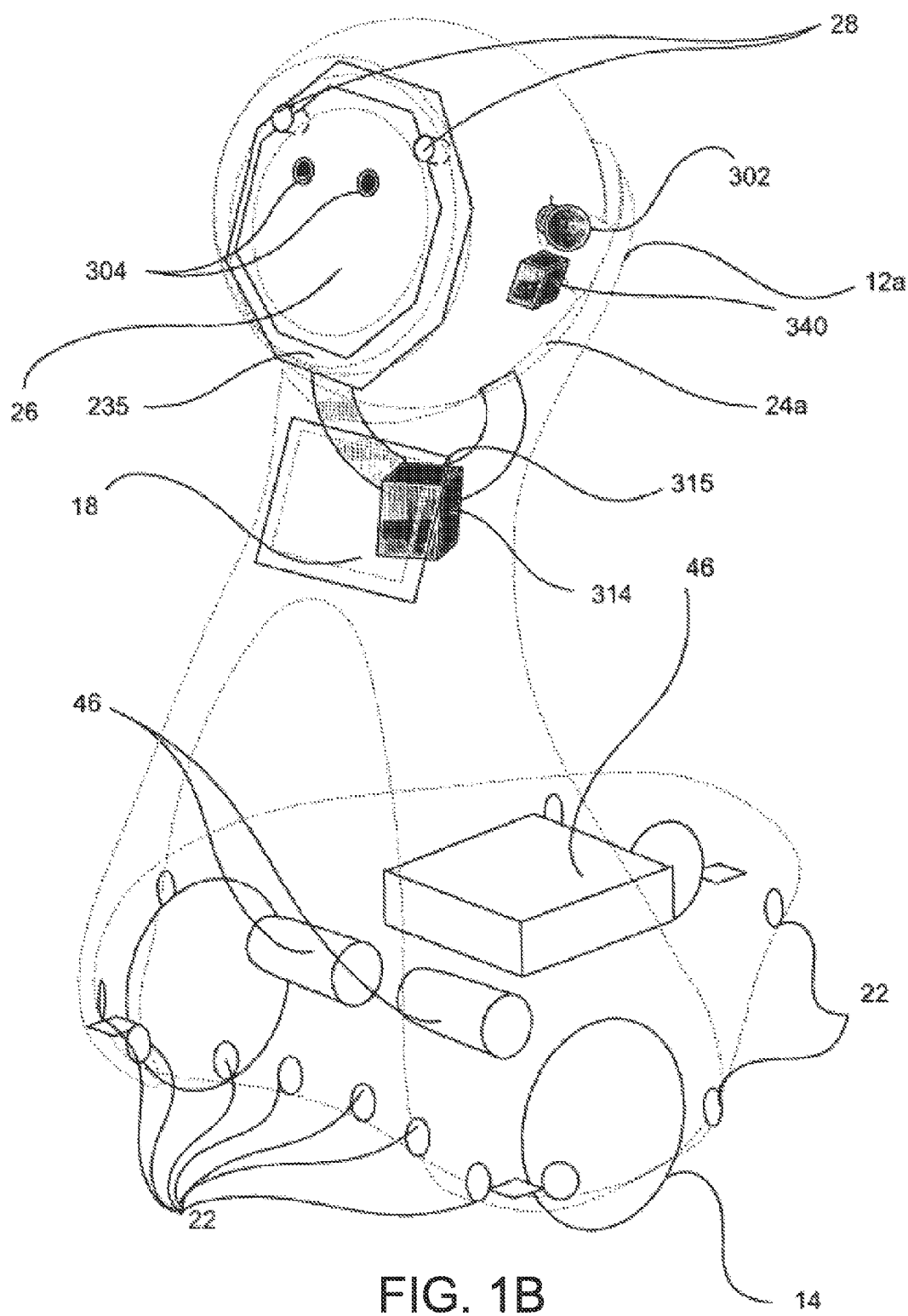
FIG. 1B is an outline schematic perspective view of the mobile robot of FIG. 1A.

One embodiment of an autonomous mobile robot 10 is shown in FIGS. 1A and 1B. The robot 10 has a body 12, one or more wheels 14, and a head 16. Certain components of the robot 10 (e.g., the body 12, wheels 14, and head 16) may each be configured to be readily mounted and demounted from the others via compatible quick-mount and/or electrical contact point arrangements, permitting different versions of each to be used in a compatible manner. A number of peripheral devices may be mounted on the robot 10, either on the body 12, head 16, or elsewhere. The depicted embodiment includes a touch screen 18 for allowing a user to interact with the robot 10, answer questions posed by the robot 10, or give the robot 10 commands. A speaker 20 or other sound-generating device is located on the robot 10. In addition, as shown in FIG. 1B, the robot 10 may utilize a number of sensors 22 mounted on virtually any location on the robot 10, for sensing various environmental conditions. For example, the sensors 22 may include cliff or edge detectors, vibration sensors, temperature sensors, cameras for visual sensing, tag detectors, laser devices for proximity sensing, wall-following, or docking with a power source or base station, detectors for following homing beacons or local environment indicia, etc.

For the purposes of this description, the robot has several categories of functional systems. Each functional system may include components such as sensors; effectors actuators); communications; and computational control. The robot described herein has several application systems, where an application system is a system for achieving an overall function to be performed by the robot. For a companion robot, there is necessary overlap with the human/robot interaction system, as enhanced human/robot interaction is a primary function. The robot includes systems (privacy protection, interaction systems) to increase user trust and emotional attachment, which has generic benefits by itself and increases the success rate of any and all other applications. The robot maintains a schedule or schedules of health, hygiene, and or need-specific regimens, reminders, messages, and encouragement techniques for associated users.

The robot is responsive to voice command, touch on screen or surface; detection of movement and human presence and (other stuff); and the robot may communicate via voice synthesis, gestures, earcons, text, images, movement, and "ambient" color response. The form of the head and torso of the robot may be designed to provide shrugging, nodding, head shaking, looking away (change of subject) and other gestural cues; the mobility system permits approach and recede motions (personal space and conversational attention cues); and a facial matrix panel may permit a full range of facial expressions. A chest panel may be an interface to a content player/engine. Low-level behaviors of the robot may accommodate interruption by a person. One embodiment may employ a scripting engine that can interrupt or be triggered by behaviors, and an alternative embodiment contemplates that some behaviors, such as self-play, rescue requests, gestural cues, can be executed as concurrent/arbitrated behaviors. The robot may include a wheeled mobility system such as two drive wheels and a passive caster, responsive to short-range object avoidance and hazard management behaviors. The wheeled mobility system may also be also responsive to mid-range obstacle avoidance planning (path planning according to a SLAM generated map) and long-range goal oriented planning.

The head 16 may be mounted on a riser 13, stalk or neck. A turning (or pan axis AP runs generally parallel to and within the neck. A nodding axis AN is transverse to the pan axis AP and may substantially bisect the head 16. A display axis may be generally transverse to and intersect either or both of the nod and pan axes, and may project normal from the display 26. The head 16 also contains a display 26 used for facial animation, and which may be adapted for videoconferencing, multimedia applications, menu input, etc. As shown in FIG. 11B, the head 16 of the robot 10 may also contain one or more cameras 28 which serve various functions, from navigating the robot 10 around an environment, observing a resident or other person, acting as a video phone or other communication device, etc. An antenna 30, modem, or other wireless communication device allows for communication between the robot 10 and a remote device, base station, etc. The teleconferencing camera(s) 28 may also be considered navigation cameras 29 and used for navigation, feature extraction and the like, or one or more separate navigation camera(s) 29 may be separately provided (as shown in FIGS. 3A-3B, for example, pointed at the ceiling to observe ceiling features, edges, shapes, or fiducials; or as indirectly shown in FIG. 22F, pointed at the floor or ground plane and including the robot's leading edge or leading portion).

The head 16 may be generally shaped as a sphere or other solid of reasonably constant diameter (which permits the head to be seated or accommodated in a neck or shoulder cavity with small enough spacing to avoid catching fingers between the head and neck joints or torso).

The head 16 may be articulated via a pan joint 315 including a pan motor and position encoder 314 and a tilt joint or hollow pivot 302 including a tilt motor and position encoder 340. Either or both of the pan and tilt joints may be yoke-type joints, which has particular advantages as discussed herein. In the embodiment shown in FIG. 4, for example, the tilt joint 302 is a yoke-type joint, which permits a face matrix panel 26 to be rotated to face into the neck (i.e., disappear from view) and the rear portion of the head 16 to be rotated to take the place of the face matrix panel 26. Alternatively, a differential drive mechanism using one motor and a clutch may be used to drive the head about two axes.

The torso or riser 13 (riser in general, to lift sensors and/or head elements to a height where the perspective of cameras and sensors is useful for obstacle detection and remote teleoperation) may support the head 16 and pan joint 315. The robot 100 includes the majority of the components in the head 16 or mobility platform 12 rather than in the torso 13 as an aesthetic and functional choice. Locating components away from the torso 13 permits the robot to avoid a ponderous trash-can appearance. Functionally, there are several benefits. Heavier components are placed in the mobility platform 12, lowering the center of gravity. The torso 13 can more easily permit variable elevation or extension (pivoted/jointed/folding or telescoping torso parts) if few components are placed there. The mobility platform 12 supports the torso 13, and may be generally triangularly shaped, or may be shaped as a curve of constant width (i.e., Reuleaux polygon with an odd number of sides). Optionally, the robot 100 fits within a generally pyramidal or tetrahedral envelope, with the mobility platform 12 generally extending along a bottom face, the torso 13 generally extending along one or two vertically angled faces, and the head 16 generally positioned at the apex. In this configuration, much of the internal volume of the envelope is open, and may accommodate a carrying tray or a retracted manipulator (not shown). Additionally, the torso 13 can be arranged to extend from one end of the mobility platform 12 toward the horizontal middle so that the weight of the head 16 tends to contribute to locating the center of gravity in the middle of the mobility platform 12. The target height for the center of gravity is approximately 30 cm from the floor (not necessarily at all times if the head can be elevated).

In a particular embodiment, the head 16 of the robot 10 may serve several functions. The head 16 may include the main control board (an example E20 shown in FIG. 69, which includes a number of circuits and subcircuits). The cameras 28 (charge-coupled device (CCD) or complimentary metal oxide semiconductor (CMOS) sensors with compatible optics) are provided for stereo vision (if two are used), and a pyrolytic (heat-sensitive) sensor (S21) may directed along the direction of the display 26 (one or more of which may also be placed in a fixed location on the torso or base, pointing forward, sideways, and to the rear). Cameras 28 may be located proximate (in this case, less than four inches from) animated matrix or segment "eyes" 304 near the display 26, such that a person looking at the robot's head and eyes during a teleconferencing session will be regarding the cameras, and a remote user observing the teleconferencing session will see the resident looking straight into the camera. While it is natural to look at "eyes" during a conversation, especially when the robot 10 acts as an avatar, channeling a remote user, it is unnatural to look at a camera (except, perhaps, for actors), and teleconferencing sessions generally have most participants looking away from the camera. Placing the cameras within a few inches of the robot's animated eyes "304", but not within them, may result in users of the robot seeming to essentially looking directly into the cameras 28 when in a video chat or teleconference. The cameras 28 should not be in the eyes "304" in this embodiment, such that the entire "eye" 304 can be fully animated, or in different positions on different faces displayable on the facial matrix panel.

The rear portion of the head 16 may be smooth and/or translucent, have a rounded or other outer shape, may include indicia or ornamentation, or may incorporate an additional informational display panel. A microphone 32 may be included to collect audio data, receive verbal commands, etc. Preferably, a vectoring microphone array 305 is provided, with multiple microphones capable of locating sound sources and removing ambient noise using time of arrival and other filtering techniques. The display 26 may be affixed to a main printed circuit board (PCB) housed within the head 16. The PCB may include most of the control electronics of the robot 10, or a second PCB may be mounted parallel to the first PCB. The main PCB may include Low Voltage Differential Signaling (LVDS) interface elements (E10 in FIG. 6B), and may be connected to compatible LVDS interface elements E10 in the body 12 via multiplexed LVDS wire pairs. Connectors and cabling compatible with high frequency LVDS signaling may be used to carry the LVDS signals between the main PCB and the body 12 as shown in FIG. 6B. The target cabling and connector impedance may be a 100 ohm differential pair. The use of LVDS may also simplify system wiring and reduce radiated emissions.

The body 12 of the robot 10 may be supported on three wheels 14 that provide stable three-point contact with or without use of a suspension system. The three wheels 14 may be arranged with two differential forward driving wheels and a rear caster, or vice versa; a greater number of wheels could distribute driving and idle wheels differently. A harmonic drive, direct drive, or conventional gear train may be used between drive motors (FIG. 4) and the wheels 14. The wheels 14 may be sized to overcome about 3 cm high thresholds and may have a radius of about that size or higher. The size of the wheelbase W (approximately 32 cm between wheels, in a particular embodiment) may be a function of necessary stability, and a lower center of gravity or larger number of wheels may permit a shorter wheelbase.

The wheels may be alternatively holonomic or omnidirectional wheels. Such systems are disclosed in U.S. Pat. Nos. 3,876,255; 4,223,753; and 5,374,879, the disclosures of which are hereby incorporated by reference herein in their entireties. The robot may alternatively use as few as two wheels with inverted pendulum dynamic balancing (depicted, for example, in FIGS. 3A-3B). In some arrangements, the robot may use obstacle-climbing or cluster wheels as described in U.S. Pat. Nos. 6,535,793; and 3,348,518, the disclosures of which are hereby incorporated by reference herein in their entireties.

Other components may be included on the robot 10 that provide additional features and functionality to facilitate bonding between the robot 10 and one or more residents or users. "Resident" is used to describe a person that lives in a home with the robot; unless used otherwise herein, the terms "resident" and "user" may be used interchangeably. A resident could be an elderly person or child who requires additional attention or supervision, various members of a family, the family pet, guests to the household identified by residents, etc. TO increase the likelihood of bonding between the robot 10 and resident, the robot 10 may include tactile sensors 34 or "digital skin" over any or all of its body 12 or head 16. These tactile sensors 34 allow the robot 10 to recognize when a resident is touching it (and respond appropriately to such touching). The tactile sensors 34 may also allow the robot to recognize when a resident is using a robot not designed to physically assist the resident for support, and appropriately react mobilizing and sending an audio warning); such a striking function may serve as an emergency shut down, should the robot 10 be malfunctioning.

The head 16 may be mounted to a moveable neck, or a neck may be rigid and unmovable, and serve as a base for the head to move thereon. A combination of both a moveable head and a movable neck is also contemplated. The moveable head 16 allows the robot 10 to interact more naturally with a resident. In one embodiment shown in FIGS. 1A-11B and 5A-5B, the head 16 is supported in a cavity 24a by a hollow shoulder support 12a. A rotatable yoke within the shoulder support 12a is able to rotate around the turning axis AT. The yoke also allows the head 16 to rotate about the nodding axis AN, so the display 26 may be hidden from view under certain conditions (see FIGS. 5A and 5B). Also, movement of the head 16 allows movement of the camera 28 and display 26 located thereon, giving the robot 10 both a wide range of camera vision and a wide range of display viewability, in a particular embodiment, the articulated head/neck combination provides four degrees of freedom.

In one embodiment, display 26 is a facial segment or matrix panel and is a monochrome, backlit or non-backlit liquid crystal display (LCD) including between about 100 and about 1000 segments individually shaped as portions of facial features on a neutral gray field. The LCD may be a square, rectangular, octagonal, etc., approximately 10-15 cm across, with a permanent pattern of segments. Neither the refresh rate nor the update rate need be rapid. Any subset of the segments can be on (i.e., dark) at any instant, and segments can change or switch state in about 50 milliseconds to about 1 second. The LCD glass is considered part of the head 16, and the display 26 should move as little as possible relative to the head 16.

The display 26 implements an eyes-brow-nose-mouth object display which is animated in synchronization with speech and interaction to express the changing affect and non-verbal behavior of the robot 10. The display 26 may be only backlit during interaction with a resident, if the backlight consumes a more power than desired. Alternatively, the display 26 may be a reflective panel, or backlit by ambient room light filtered in through the (translucent) head 16, backlit by one or more white light emitting diodes (LEDs) and an appropriate diffuser, or any combination of these. The display 26 also may be an organic light-emitting diode (OLED) panel, which may require no backlight (although one may be used) and could consume less power if light-on-dark facial patterns are used.

For a robot 100 provided with the facilities discussed herein, power consumption from two backlights can be half or more of the power consumed by the robot 100 at any time, and can restrict the operation time of the robot to 2 hours or less (conversely, operating without any backlight could increase this time to 4-5 hours).

The display 26 may be constructed using reflective bistable (non-volatile) technology such as electrophoretic, electronic ball twisting, electronic ink or electronic paper displays, and/or hybrid electronic ink/active matrix displays. Electrophoretic or electronic ink displays are made by a high-contrast, low-power technology that is bistable and retains an image when unpowered (e.g., E-Ink™ high resolution matrix Imaging Film or segment Display Cells from E-Ink Corporation of Cambridge, Mass.; or electronic ink/gyricon sheets from Xerox/3M). This type of technology may have a switching time of about 0.5-1 s, allowing for satisfactory display of caricatured facial expressions. Hybrid electronic ink/active matrix displays combine a thin film transistor (TFT) active-matrix back plane, containing polymer electronics-based pixel driving or conventional TFT technology on steel foil, with a front plane of reflective electronic ink as above (e.g., from SiPix Imaging of Fremont, Calif., or Polymer Vision of Eindhoven, NL). Display types operating on different principles, but that display at least some of the identified characteristics (reflective or transparent, very low power, bistable, etc.) are Fujitsu e-paper displays (cholesteric selective reflection film substrate-based color display from Fujitsu, Japan), or NanoChromics™ displays (nanostructured film electrode/electrochromic viologen molecule display from NTERA of Ireland).

When describing the display 26, the term "segment" panel means, in one instance, a panel made up of discretely shaped elements, rather than an X-Y matrix of pixels. The use of the term "matrix" panel means, in one instance, a panel made up of an X-Y matrix of pixels. The potential benefits of a matrix panel are that it can be used as an alternative (or the sole) informational display, and that the faces or facial expressions to be displayed thereon can be completely changed in software, downloaded, or user-designed. A segment panel, however, can be simpler and more efficient; can give extremely smooth outlines for activated segments; and can be more easily adapted to user or community programming of expression sequences.

Figure 10A:
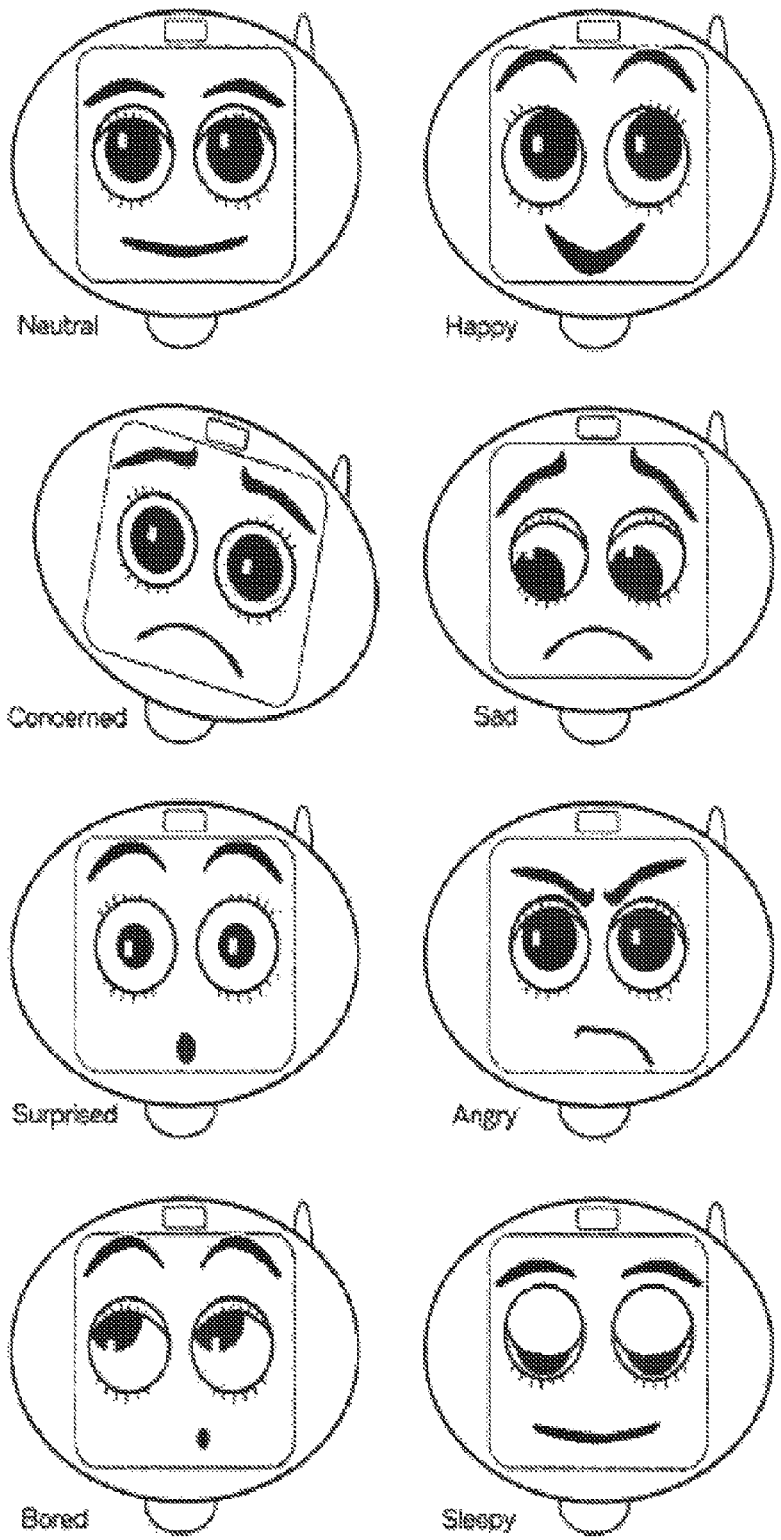
FIG. 10A depicts affect expressions for robot screen display in accordance with one embodiment of the present disclosure.

While the description herein contemplates an octagonal or other multi-sided polygon panel shape that permits covering most of the surface area of a circular panel window 101 of the head 16, an ordinary 4:3 or other rectangular LCD panel may be used vertical or horizontal orientation. More than one panel can be used within the circular panel window 101 (e.g., three panels horizontally or vertically oriented can fill more of a circle than a rectangular panel). As shown in FIG. 10A, mouth, eye, and eyebrow objects can be arbitrarily formed from a multiplicity of pixels using a matrix display, or can be formed in set shapes from a number of segments using a segment display. Of course, a panel 26 may incorporate both segments and matrix portions, and matrix pixels can be considered one kind of segment. The segment or facial matrix panel 26 may be provided with a sufficient number of segments or pixels by conventional manufacturing techniques.

Although the robot 10 of FIGS. 1A and 1B depicts two screens 18, 26, used for input and output, respectively, other embodiments of the robot may utilize only a single screen for both functions, typically labeled with both numbers (e.g., "18, 26" see FIGS. 3A-3B). For example, a single touch screen may be used for both input and output viewing, and may be located on either a head or a body of a robot. Alternatively, a single display could be used for output, while input interaction with the robot could be via a plurality of buttons, knobs, tactile or other sensors, etc. A tracker ball device or other type of contact pad for moving a pointer on the screen may also be utilized. The tracker ball or contact pad may be located on the robot or remote therefrom.

An exemplary single-screen mobile robots are is depicted in FIG. 2. The depicted robot R2 may include a V- or U-shaped base 112, that allows the robot R2 to function as a walking aid or guide. The robot R2 includes at least three wheels 114 for stabilizing a user who grasps and leans on a pair of handles 136 (generally when a head 116 of the robot R2 is in a horizontal position) in order to walk with the assistance of the robot R2, much like a conventional walker. The robot R2 may control the rotation of one or more of the wheels 114 to steer the robot, or prevent the robot R2 and/or user from slipping or moving too quickly, and/or to modulate the walking of a user, who may steer the robot R2 by turning the head 116 via the handles 136. A torsion, angle, position, strain, and/or any other displacement detector may detect the twisting of the head 116 relative to a stalk 124 or a track 134 (described below), and alter the movement of the wheels 114 so as to assist the person in walking.

The stalk 124 includes a track 134, along which the head 116 moves 140 (as depicted in FIG. 2). In addition, the head 116 may be rotatable and/or may swivel. The track 134 may be passive or motorized. The head 116 may be fixed to a particular position along the track 134 by turning a tightening knob, for example, or may be automatically adjusted and/or fixed into position by a motor, locking bolt, cable, chain, rack and pinion, or any other system. The movement of the head 116 along the track 134 also may be effected by an electric motor under control of a control unit, for example, and may move in accordance with various robot behaviors or functionalities.

Track 134 may have a top "dead center" position, such that at the topmost point along the track 134, the head 116 may lie flat (i.e., normal to gravity, G, optionally detected by an accelerometer, gyroscope, digital level, etc., in the head 116). Alternatively or additionally, the head 116 may turn over to face a direction opposite to the directions shown in FIG. 2A. As shown in FIG. 2A, the track 134 goes all the way to the ground, and a camera on the display face side or sides of the tray (head 116) may be moved to the ground position to provide aground plane view (for navigation, or for looking under sofas and the like for lost objects).

The robot R2 may include an display 126 on the head 116, which may function as either a touch screen and/or visual output screen, as described above. A speaker 120 may be located on the head 116 for audio output; a microphone 132 or array 132 may be utilized for audio input. Moreover, the robot R2 may include any appropriate sensors 122 or other accessories, such as a finger-cap heart-rate monitor, to provide medical feedback to a remote caregiver or doctor, described below. The head 116 and/or display 126 may include one or more temperature, mass, weight, or other sensors, which may be used to detect properties of items placed on the tray, or to facilitate appropriate use of the tray as a means to move items from place to place (e.g., to detect too hot items, too heavy items, or to detect items placed too far off-center). The head 116 may be suitable for carrying or holding items (such as, for example, food or beverages), and may include reactive, active, clamping, or passive holder(s) or receptacle(s) for food, beverages, and/or medications.

FIG. 2 also illustrates an example of a mobile robot R2 that is equipped with safety features. The speaker 120 may function as an annunciator for the robot 82, or the robot R2 may include another "noise-maker," (including gears or other machinery that are selected to be more noisy than necessary). The speaker 120 may be used in combination with a particular audible profile, in order to audibly alert a resident or other people to the presence of the robot R2. The presence warning emitted by the speaker/annunciator 120 may be aperiodic beeping, a continuous tone, a bar of music, a soothing sound, or any other appropriate notice which alerts people audibly to the presence of the mobile robot R2. However, the noise should not be loud or intrusive. In one embodiment, it is audible in about the same loudness range as ordinary footsteps on a floor. In addition, one or more visible beacons 138, such as a spinning light bar, may provide supplementary visual warning. The visual signal emitted by the beacon 138 may be flashing lights, strobes, a continuous or changing beam of color, an image displayed on the display 126, or any other appropriate visible signal which alerts people to the presence of the mobile robot R2. The visible signal may also be passive, e.g., reflectors or retroreflective patterns.

FIGS. 3A-3C depict several variations R3-R7 of a robot according to the embodiments of the disclosure. Each of the robots R3-R7 may include RE communication and may use the robot base station (shown here as BS, positioned atop a set top box STB described below).

The robot R3 balances on two coaxial wheels (or a ball) using inverted pendulum balancing (i.e., active or dynamic balancing via servo control of the wheels using gyroscopic sensing), and is self-righting. Near the top of the robot is a display or teleconferencing screen 18 as described herein. On top of the robot, pointing at the ceiling, a combination camera 28, 29 handles teleconferencing functions and navigation functions. The combination camera may be oriented at the ceiling for following ceiling and/or light fixture and/or door and corner edges, features, indicia, or fiducials, and may be tilted by, e.g., 90 degrees to face forward for teleconferencing or additional modes of navigation. More than half of the weight of the robot is arranged near the wheels, such that the center of gravity of the entire robot is as close as possible to the axis of the wheels or ball. Because the tipper ring 12, at knee level or above, is significantly larger than any part of the bottom of the robot, it may be less likely that the wheels or toe-level portions of the robot will be tripped on. Similarly, the tipper ring is circular and as wide as a person (e.g., 16-24 inches, preferable about 18), and at knee height will encounter most table and chair legs.

The robot R3 may include an inertial sensor near the middle of the height of the robot (3-4 ft.) such as an accelerometer, which may detect collisions. At the top of the robot, a self-righting platform is provided. The platform is also preferably dynamically balanced to maintain a horizontal orientation, such that items carried thereon will not tip or spill. Additionally, object detection and avoidance sensors are positioned at the top of the robot R3. The platform supports a medication dispenser 17. As shown, the medication dispenser is a circular carousel of slots, each slot holding a small paper cup suitable for containing pills or a "Dixie" cup suitable for a swallow or so of water. The dispenser or pill station may be fixed, rotatable manually, or by motor. The dispenser may include a movable D-shaped "purse" handle (not shown) and may mount and dismount from the robot, and or lock to the robot. The dispenser may also fit into a loader, which may be positioned at another location in the home (e.g., in the bathroom, networked, and containing a magazine of pills for loading the dispenser). Loading techniques discussed herein may use a pre-filled (off-site, at a pharmacy, etc.) magazine type loader to load the dispenser. As shown, the dispenser MD or 17 may also be positioned at another location in the home.

No one or more components are necessary. A variant R5 is essentially alike, but includes an extending or telescoping riser 13A (using telescoping barrels, jacks, screws, scissors, or an articulated and/or jointed arm), such that the medication dispenser 17 or other components can be moved about the house with a lower center of gravity. A variant R4 omits the display 26, 18 and dispenser 17, but still includes a navigation camera 28 and many remaining facilities. Such a robot R4, in omitting a display screen, may guide the resident to a set-top box STB and television for vide chat purposes. That is, for those robots which do not have a teleconferencing camera 28, or even for those that do, a set-top box STB may form a part of the robot system. The set-top box STB may be integrated with the robot base station or a separate component privileged on the robot base station network. As noted, the base station (and possibly the STB) are located in the home at the broadband ingress (typically cable, xDSL modem or fiber optic terminal, but also WAN wireless networks). As shown, the set-top box includes a teleconferencing camera directed toward a position in front of a TV upon which the set-top box STB is most likely positioned. Because a normal household television screen is much larger than any screen that can be carried by the robots R3-R7, in a teleconferencing mode (that may be treated as a regiment event for the purpose of scheduling and bringing the resident to a regiment compliance object—the STB and TV—as discussed herein), the robot may bring the resident to the STB and TV for a videoconferencing session that takes advantage of a large screen (on the TV), stable acoustics (a microphone array on the STB that is not subject to motor and mechanical noise), stable AC power, a stable camera, and wired broadband access.

Two further variants are shown in FIG. 3B and FIG. 3C. The mobility system of the robot R6 of FIG. 3B uses three pairs of wheels front to back (six wheels in total), in which the center wheel pair is slightly lower than the outer two pairs. This permits low friction on smooth surfaces, good traction on soft surfaces, and ready turning in place on most surfaces. The display 26, 18 takes the form of tablet computer form pad, removable from the robot as necessary, but oriented similarly to the other embodiments discussed herein when the robot R6 is normally navigating. The display pad 26, 18 itself would have a separate wireless connection to the base station BS. The navigation camera 28 is preferably not be on the pad 26, 18, although a teleconferencing camera may be (through which one could find a dismounted pad). The medication dispenser in this case is a dismountable chest or kit, and may be "hung" on the robot and engaged thereto. The "head" 16 in this case is primarily for mounting the display pad 26, 18 and medicine chest 17.

The mobility system of the robot R7 of FIG. 3C uses a differential drive and front or rear caster similar to household robotic vacuums. An inverted cone, largely empty in the middle, leads up to the tipper ring 152, configured as discussed herein. In the middle of the tipper ring, the medication dispenser 17. In this case, the medication dispenser 17 essentially hangs, pivoted and free to swing, (remaining essentially horizontal at most time) within the cone and center of the tipper ring 152. The medication dispenser 17 may also be actively controlled to stay horizontal. The variant of R7 may be the least costly discussed herein, and may navigate semi-randomly (with wall following and other chamber diffusion techniques) or with limited recording of doorways and the like, being able to identify its proximity to the resident, using proximity and presence scores as noted herein, but using no maps. In this case, the R7 variant would start trying to find the resident earlier than the other variants, e.g., from 15 minutes to an hour before a regimen event. This robot R7 may have tag or lighthouse based navigation, and may communicate with a pill station or medication dispenser 17 not on the robot R7 by infrared. The medication dispenser may be replaced with, or have underneath it, a net for holding and carrying various objects. Again, the tipper ring 152 is of larger diameter than the base. The base station BS may be RF-connected, but in this case may also be alternatively connected to a regular phone line, and provide only limited data services (and may then be remotely communicated with indirectly by caller ID channels, tip and ring, and other phone line signaling).

FIG. 1B, as noted, depicts the embodiment of the mobile robot R1, having generally a triangular base 40, a lengthened body 12, and a head 16 at the top of the body 12. In this embodiment, the head 16 includes a yoke assembly 42 allowing for movement. The robot R1 includes wheels 14, sensors 22, at least one camera 28, and one or more screens 18, 26. The motors 22 are located proximate the wheels 14. Additionally, main power/control components 46 are located in the base 40. Location of the power/control components 46 may vary as desired for a particular application. In certain embodiments, the power/control components may be split into a power component and a control component, with the power component located in the robot base or body, and the control located in the head.

FIGS. 4A and 4B illustrates an example in which object detection coverage is provided by a plurality of converging infrared emitter-sensor elements, arranged in zones. Of those sensors, several face down for cliff sensing, several face forward, some face backward, and a number are special configurations described herein. This sensor system may function alone, or, as an alternative, may function in combination with one or more bump switches for redundancy, for example.

In accordance with one example configuration, the robot 100 includes six infrared rangefinders for obstacle and stairwell avoidance, with three bump switches for obstacle avoidance when backing up.

The infrared sensors preferably have a similar electronic implementation such as, for example, a synchronous reflectivity emitter/detector pair comparable to cliff detectors. With regard to the infrared rangefinders, as non-limiting implementation examples, emitter/detector pairs may be deployed in accordance with several different configurations as follows: Convergent-Crossed emitter/detector pairs 965 are emitter/detector pairs providing a specific detection zone at the point of intersection, as used in cliff sensors. Diffuse-Parallel 966, 962A, 962B are colocated emitter/detector pairs preferably providing a 30° field of view (+/−15°), detecting objects at distances between (for example) about 2 cm and 20 cm, depending upon the reflectivity of such objects. The Tangential sensor 961 may utilize a "broken beam" topology created across a concave surface 978 at the front of the robot 100.

In accordance with at least one configuration, as non-limiting examples, the sensors can perform synchronous detection during and after illumination pulse of associated emitter; in which each sensor reading produces two scalar values denoting ambient reflectivity and illuminated reflectivity. With a least 8-bit dynamic range, each sensor can produce at least 100 such samples per second. In a preferred configuration, analog conditioning/filtering/integration is done on each detector's signal before moving into the digital domain. Further, the detector components may be stand-alone photodiodes, or may integrate transimpedance amplifiers to improve the signal-to-noise ratio through a wiring harness. A robot 100 including 16 such sensors is shown in FIG. 4B, for example.

A preferred configuration relates to a robot including six forward-facing diffuse sensors 966, spaced 7 cm apart, which can provide sensor coverage for objects up to about 14 cm away, provided that the objects are reflective enough to be detected at that range. Three downward-facing cliff sensors 965 are placed before each wheel 14 in its direction of travel. Two angled diffuse sensors 962A, 962B and 963A, 963B at the rear-angled sides of the robot mobility base 12 provide obstacle detection in the reverse direction, and can guide the docking process in conjunction with matching emitters on the dock, for example. Two angled convergent sensors 966 at the front provide a defined detection zone just outside the projected envelope of the robot, for use in wall following and wall locating, for example. A tangential beam across the front 978 of the robot base provides precise contact information when an object touches any part of that surface, and may accordingly accelerate collision detection and accurately locate the object's position.

Because the mobile robot 100 functions in a household environment, the issue of household safety may be addressed by any of a variety of features. Among these features, inter alia, are personal contact avoidance, obstacle avoidance (including the ability to detect and/or avoid objects that exist over a wide range of possible heights and positions relative to the robot 100), and damage avoidance-avoiding and/or mitigating damage to either the home, objects in the home (such as furniture, fixtures, and the like), or the robot itself, for example. In connection with these features, the robot preferably includes redundancy in detecting and/or avoiding obstacles.

Regarding personal contact avoidance, the robot 100 preferably avoids initiating physical contact with any person—such as the user—unless there are circumstances that make such contact unavoidable or necessary. However, as non-limiting examples, the robot 100 may initiate contact when a possible medical emergency requires the robot to measure the temperature of the user, or when an authorized remote user issues a command to the robot to make physical contact with a person, inter alia.

In accordance with at least one aspect, the robot 100 includes one or more sensors for detecting the presence or absence of objects over a range of physical space, in which the monitored space is divided into protection zones. As illustrated in FIG. 4C, for example, the area surrounding the robot 100 includes a "toe zone" Z10 ranging from ground level up through about two inches above the ground; a "bump zone" Z20 ranging from about two inches up through about 4 inches above the ground; a "near zone" Z30 ranging from about one inch up through about 12 inches above the ground; and a "face zone" Z40 corresponding to the area directly in front of the face 26 of the robot, and which varies as the face 26 is raised or lowered, or as the face 26 swivels or rotates. Each protection zone is monitored by at least one sensor (such as, for example, a photosensor or a bump switch), and preferably there is overlap of the monitored zones among two or more of the sensors. As a result, the redundancy of obstacle detection is improved and the likelihood of an obstacle failing to be detected is reduced, because even if an obstacle is not detected by one of the sensors monitoring an overlapped area, another sensor monitoring the same overlapped area may nonetheless detect the obstacle.

As illustrated in FIG. 4C, the bump zone Z20 is monitored by a bump sensor 957, such as a contact switch or pressure sensor. The near zone Z30 is preferably monitored around a full perimeter of the robot 100, by (for example) a light curtain that may include beam emitters L21, L22 and photosensors 956 that detect light reflected off of objects that was emitted by the beam emitters L21, L22. Objects between 2-4 inches above the ground may be detected at between 1 to 5 inches laterally outward from the robot 100, for example. Low objects such as toes or door thresholds may also be detected. Also, one or more cliff sensors may be positioned around the mobility platform 12 and detect any sudden or precipitous drops in ground elevation over the full perimeter of the robot 100.

In the area in front of the robot 100, the light curtain may detect incursions by objects at a height between approximately one through 12 inches above the ground. Toward the face 26, the near zone Z30 may also be monitored by an infrared or ultrasonic obstacle sensor. At far range, such as two through twenty feet or more, the robot 100 may include a camera 304, which can detect both near and far Objects when image processing is applied to the data produced by the camera 304.

In order to detect people in front of the robot 100, heat sensors, ultrasonic object sensors, or voice vector detector arrays may be used. For example, the robot 100 may include an array of six microphones (not shown) positioned such that the direction of the source of a sound may be determined; when the robot "hears" sound that corresponds to speech and the voice vector array indicates that the source of the sound is in front of the robot, the robot may respond accordingly, in addition, the robot 100 may employ such "people detectors" at either side and/or behind the robot 100, in order to detect people who may be standing or approaching too close to the robot (such that a danger of collision or of the robot tipping), in order to respond appropriately.

The robot can receive data from two or more sensors, integrate the sensor data to predict the likelihood of an obstacle being present in one of the protection zones, and modify its actions (for example, by reducing speed, changing the direction of travel, and/or towering the head 16, inter alia) when the predicted likelihood of an obstacle being present exceeds a threshold. Moreover, the threshold can be adaptively modified in accordance with experience—for example, when the robot collides with an obstacle after failing to predict the presence of that obstacle, the robot can lower the threshold; or when the robot discovers that a predicted obstacle did not in fact exist, the robot can raise the threshold.

As an advantage, by predicting the presence of an obstacle coming into the path of the robot based on input from more than one sensor and/or more than one protection zone, the robot can avoid or mitigate obstacles encroach onto a primary protection zone.

As illustrated in FIG. 4C, for example, the face 26 of the robot may include a forward-directed camera 304 that monitors and can detect objects over a broad range of distances in front of the camera 304. The robot 100 may also include a first beam source B21 that emits downward-directed beams of light L21 and a second beam source B22 that emits upwardly-directed beams of light L22. The beams of light L21 and L22 preferably intersect over an area, and when either beam contacts an object, light is reflected off the object and is detected by photosensors; the range of space monitored by the beam sources B21, B22 and photosensors 956 generally corresponds to the near zone Z30. The different beams of light L21 and L22 may have mutually different wavelengths, or may be encoded with different signals, for example, such that the reflected light detected by the photosensors 956 can determine which beam source B21 or B22 emitted the reflected light. When the camera 304 detects a possible object lying near the lower area of the face zone Z40, and the photosensors 956 also detect light reflected off of an object, the robot 100 can determine that the likelihood of an obstacle in the near zone Z30 is high, and halt the robot 100 from moving forward in order to avoid colliding with the obstacle, for example.

In addition, the robot 100 may include a microphone that monitors ambient sound or noise levels. When the microphone input indicates sound corresponding to speech, for example, the robot may determine that it is likely a person is in the vicinity, and accordingly reduce its movement speed, in order to reduce the chance of colliding with the person. The robot 100 may also monitor other sensors such as heat detectors (infrared photosensors, for example) or cameras, and make behavior determinations based on one or more of the sensors. For example, if no person is in fact in the vicinity of the robot, but the television is turned on, then the robot's microphone detects speech, but the heat detector does not indicate the presence of any heat sources. In such a case, the robot 100 may instead determine that no person is present, and accordingly decide not to reduce its movement speed.

When the robot 100 is in an environment containing many potential obstacles (for example, in a cluttered basement or in a room full of people), the robot may operate at stow speed in order not to collide with people or things. When operating at slow speed, the robot may rely more on bump sensor input than on optical cameras or photosensors, for example.

The cameras on the robot, depicted for example, as item 28 in FIGS. 1A and 1B, allow the robot to view a resident or other persons in an environment. Even if the resident is comfortable with an interactive robot regarding them on a regular basis, the network connectivity (as described below) of the robot may raise privacy concerns for residents. Residents may feel that they are being "watched" by a third person, or that an imagined "hacker" may be able to view them in their home. Accordingly, the robot may be equipped with functionality that displays or otherwise ensures that the privacy of the resident is not being compromised. This functionality includes, but is not limited to, camera/head position limitations, visible or audible indicia, or default conditions that prevent lapses in privacy.

FIG. 5A depicts a perspective and side schematic view of a movable camera 28 in an operating position within the head 16 of a robot. FIG. 5B depicts the same camera 28 in a non-operating position. Here, the camera 28 includes a body 300, having a pivot 302 and a lens 304, (Alternatively, the entire camera 28 may be located behind a shield 306, which may completely enclose a void 24a within the head 16.) Wires for power and visual image feed are contained within a support structure, and may enter the body through the hollow pivot 302. Alternatively, the wires may be located external to the support structure, but would need to be long enough to allow unimpeded movement of the head 16. In FIG. 5A, the camera 28 is directed outward, providing an unobstructed forward view, in the operative position. The resident therefore may be able to clearly ascertain that the camera 28 is capable of recording (and potentially transmitting) visual data. However, in the non-operating position of FIG. 5B, the camera 28 may be rotated or otherwise positioned so as to face an opaque surface forming the hollow 24a, which may encompass the entire field of vision of the camera 28. A non-operating position depicted in FIG. 5B may alternatively function as the default position for the camera 28, unless the resident grants permission for the operative setting of FIG. 5A.

If utilized, a shield may be transparent to allow clear viewing of the camera 28 within the hollow 24a. Alternatively, it may be entirely opaque and movable into a position to cover the camera 28, so the resident may directly control the ability of the robot to view and potentially transmit visual data. In one embodiment, the camera and/or lens is entirely withdrawn into the robot's body, or the lens is turned to abut the robot's body.

Accordingly, the robot is not only rendered incapable of recording its surroundings, but can be readily confirmed as incapable of such recording, as indicated by the blocking of the lens, the turning of the lens to substantially face the robot's body, or the turning the head to change the field of view. The visual cue of camera or head position may be supplemented by an electronic light that may be dimmed or undimmed when the camera is recording visual data. Thus, the person can clearly see and confirm that they are not under potential surveillance by a third person, A similar mechanism can be used with a microphone 305 or microphone arrays 305 on the robot; the robot may disconnect, shutter or otherwise disable microphones when entering a privacy mode. If the microphone(s) 305 are turned along with the head or otherwise moved to be blocked, an elastomer seal in the inoperative position may further muffle sound. Similarly, external antennae can be disconnected. In each case, the transmitting medium is rendered incapable of monitoring the resident.

Figure 5C:
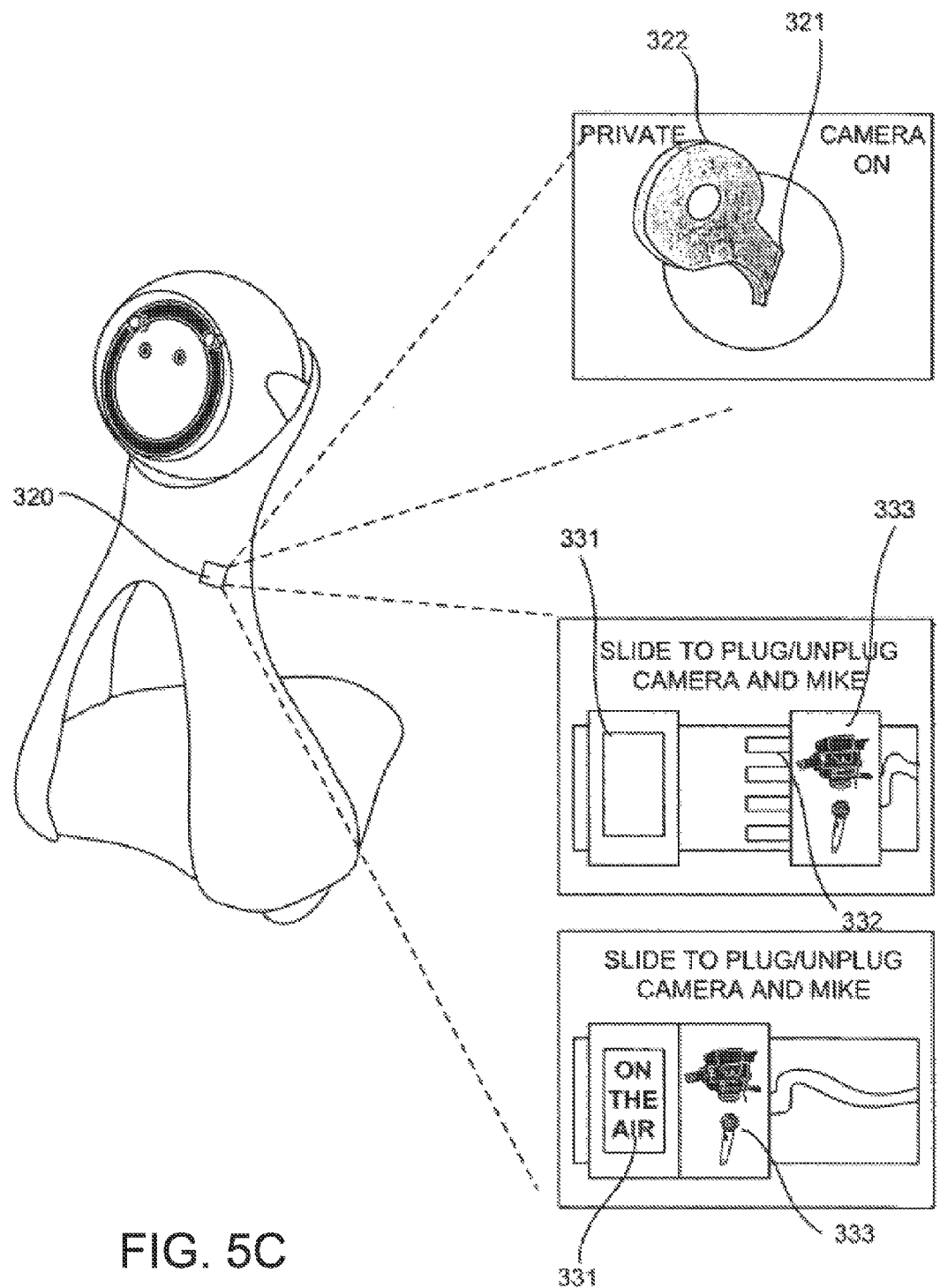
FIG. 5C is a schematic view of a privacy interface for use in a mobile robot in accordance with one embodiment of the present disclosure.

As shown in FIG. 5C, a lockout mechanism may take forms other than turning a camera 28 or microphone(s) to be isolated from the local area. In one model, the resident or user has verifiable, ultimate control over the physical ability of the robot to monitor the local area. A key slot, plug, or other connector 321 capable of receiving a lock-out member (such as a key 322, dongle, etc.) is provided at a lock-out station 320 readily accessible and visible on the robot 10. If the robot is constructed under the model that the resident has control that may not be overridden, the engagement of the lock-out member or key 322 mechanically closes electrical contacts, enabling the camera 28 (and microphone) to operate, and completely disabling the camera and microphone in when in a private position. In an alternative arrangement, a lock-out member as a slider 333 including visible electrical pins 332 is arranged in the lock-out station 320. The resident may readily verify that the camera and microphone cannot work at all, because critical electrical paths are open. When the slider 333 is closed to a receiving plug 331, a notifier indicates a readily understood message (e.g., "on the air") or signal (e.g., flashing LED) giving notice that the robot is connected to the world at large. This kind of arrangement, a privacy member configured to physically unplug the sensor when a privacy mode is selected, may give the resident a degree of confidence that the household is "hacker-proof" with respect to camera or microphone surveillance of the resident.

In an alternative model, the key slot, plug, or other connector 321 does not mechanically close electrical contacts, and can be overridden in emergency situations in this case, software transmission control routines may enable transmission of surveillance data from the camera 28 outside the residents home only when the lock-out member is inserted in the connector 321. In this model, the robot 10 may normally use its controller connected to the camera or microphone to monitor surveillance data from that sensor. The robot may run a transmission control routine configured to enable transmission of surveillance data from the sensor (to the caregiver) outside the residents home if the resident grants permission for the transmission. However, an override routine may be configured to enable a transmission of surveillance data from the sensor outside the residents home (i) in an emergency condition detected by the robot. Alternatively, if an authorized remote caregiver sends an authorization previously permitted by the resident together with an emergency condition, the camera and/or microphone may be enabled. wherein the transmission of surveillance data by the robot outside the residents home is otherwise prohibited. This kind of arrangement may also use a privacy member configured to physically unplug the sensor when a privacy mode is selected, if the override mode uses a mechanism or relay to "replug" the sensor.

Figure 5D:
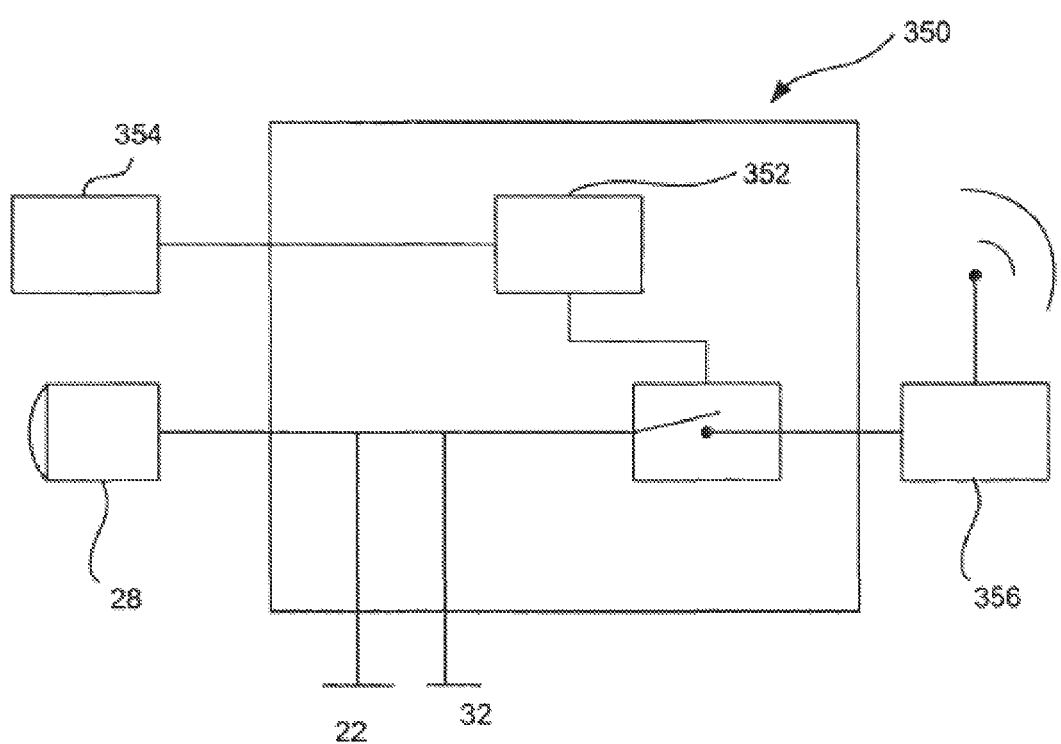
FIG. 5D depicts a schematic view of a privacy device in accordance with one embodiment of the present disclosure.

In accordance with at least one embodiment, any sensor input capable of Observing or monitoring the environment surrounding the mobile robot may be routed by a privacy device 350, as illustrated in FIG. 5D. A privacy controller 352 tracks any permissions granted or denied by the resident, and controls the data stream from sensors, such as the camera 28, microphone 32, or other sensor 22, thereby permitting sensor input to be recorded by the data recorder 356, and/or transmitted by the antenna 30 to a remote data recorder, only if such recording or transmission complies with the permissions granted by the resident. The privacy controller 352 may be implemented as a discrete hardware item or as a division of another piece of hardware; alternatively, the privacy controller 352 may be implemented as a software routine. In one embodiment, the privacy controller takes the form of a key, plug, dongle, or other physical medium that enables sensors only when installed, e.g., as shown in FIG. 5C.

An override unit 354 may override privacy directives issued by, or monitoring capabilities disabled by, the privacy controller 352, and thereby permit the sensor input to be temporarily recorded and/or transmitted, despite the permissions implemented by the privacy controller 352. In certain embodiments, the override unit 354 may only override the privacy controller 352 when either a predetermined event is present, the event being either a threshold on the output of one or more sensors or interpreted data as detected by the controller 352, or when a caregiver's override command is received by the mobile robot. An override command from the caregiver may be in the form of an encrypted code or other secure transmission, encoded or digitally signed using any suitable method, such as, for example, digital certificates, public-key encryption, a predetermined password, or any other suitable mechanism.

The override unit 354 may permit surveillance or monitoring temporarily when, e.g., a distress condition of pulse, breathing, medical, environmental, or safety monitoring sensors, or other emergency situation is detected. When a distress condition is detected, the robot may also make an outbound call requesting the caregiver to check on the resident. Also, the mobile robot may include a receiver for wire receiving the override command (from a remote terminal, which may be operated by a caregiver, for example). In addition, there may be circumstances in which considerations of safety or health suggest that the usual permissions granted or denied by the resident be temporarily overridden. Master override permissions may enable a caregiver to receive permission to temporarily override subsidiary permissions in emergency situations, or to enable medical monitoring devices or data analysis conclusions to override these permissions.

Circumstances that may require overriding of the privacy controller 352 may include a determination by the mobile robot that the resident has become non-responsive (and therefore possibly unconscious), or when a fire alarm or smoke detector has triggered on the robot, or in the environment. In such circumstances, the override unit 354 may override the privacy controller 352 to permit input from the camera 28, microphone 32, or other sensors 22, to be transmitted to a remote terminal belonging to a caregiver, police or fire department, or ambulance service. Therefore, the caregiver may be alerted to such emergency circumstances, and receive relevant video, image, or audio information from the mobile robot in proximity to the resident.

FIGS. 6A-6D depict some of the software architecture, electronic systems, and network connections of embodiments of a robot as disclosed herein. Not all of these is necessary in every robot discussed herein, but the description applies at least in part to each embodiment.

Figure 6A:
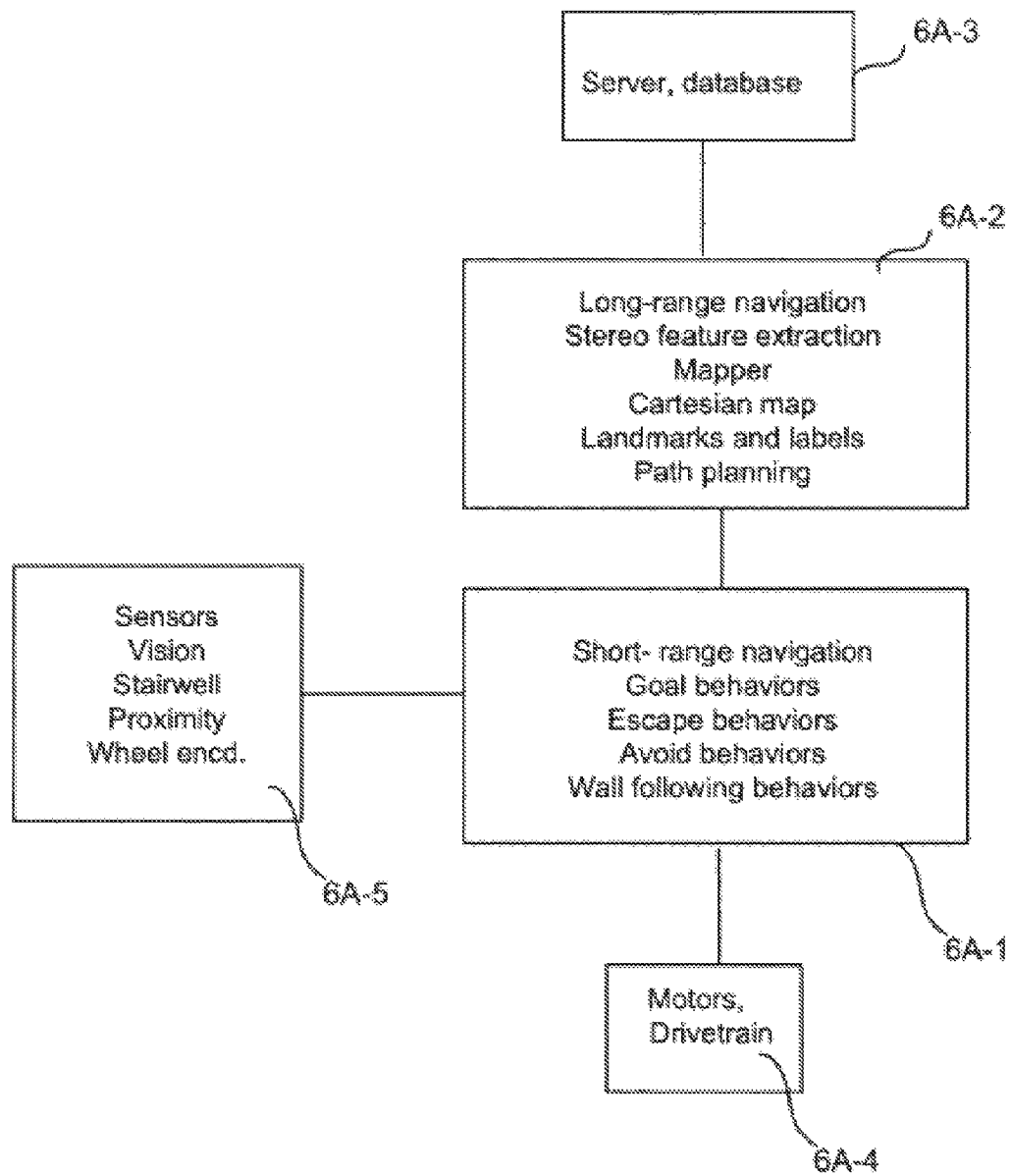
FIG. 6A is a schematic block diagram of internal architecture and relationships between components in a mobile robot in accordance with one embodiment of the present disclosure.
Figure 6B:
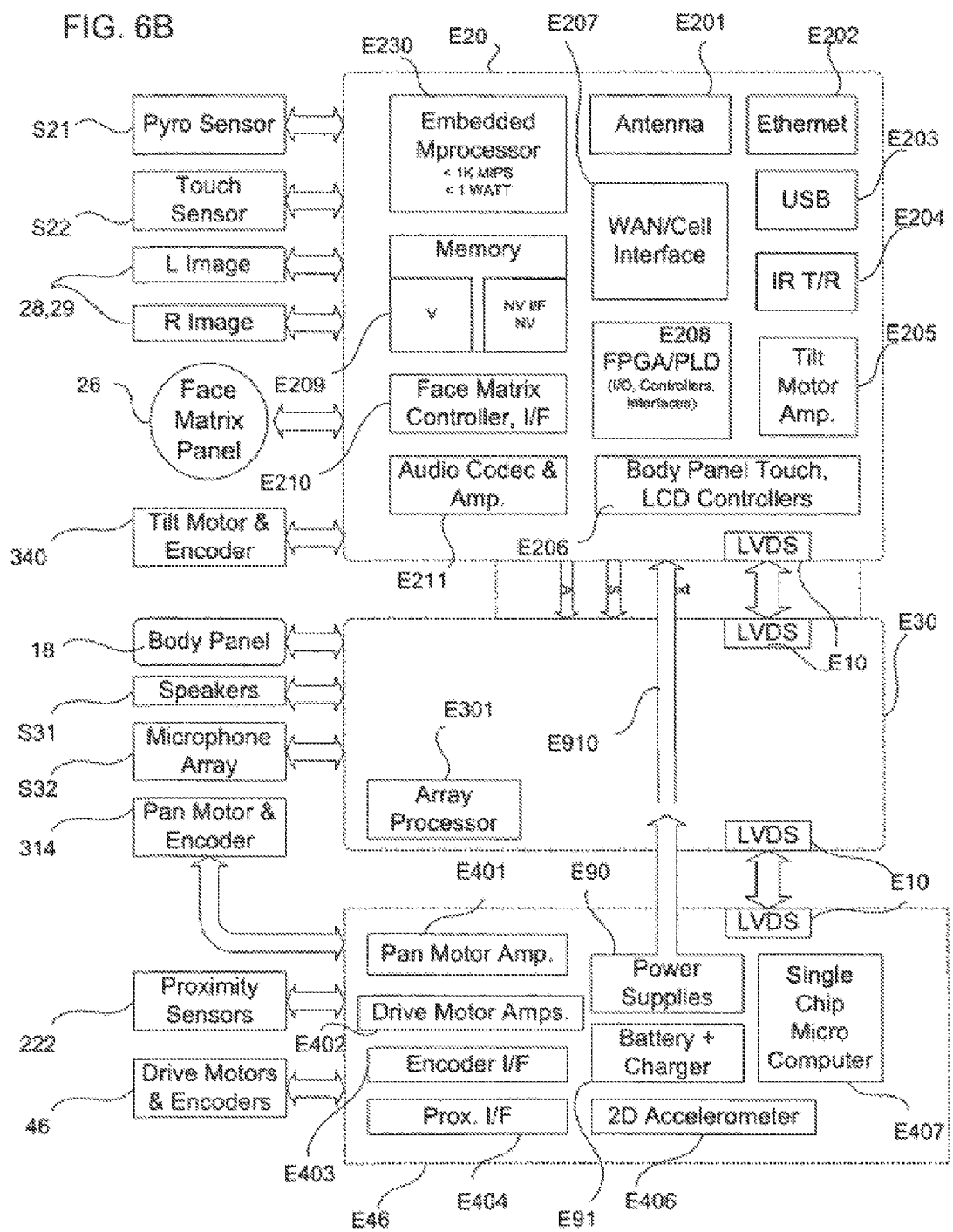
FIG. 6B is a schematic block diagrams of alternative electronic systems for a mobile robot in accordance with the present disclosure.

FIG. 6A shows a basic architectural distribution of tasks and functions. A behavior based robot acts largely on the basis of behavioral systems, in this case as depicted as reactive systems 6A-1. Short-range navigation is navigation within and among obstacles in a room, and would normally be handled by a combination of cruising and turning behaviors. Goal behaviors seek, home in on, or search for relatively simple goals—e.g., a charger, a virtual wall or lighthouse, a beacon, a sound, an area of strong signal reception. Escape behaviors enjoy higher priority in the event of robot stasis, stuck, canyoning, or other trapped conditions. Avoid behaviors may avoid simple hazards cliff's, perhaps people. Wall following behaviors and other behaviors follow obstacles to improve navigation and diffusion. AU of these behaviors are arbitrated and contend for control of actuators 6A-4, based upon a collection or suite of sensors 6A-5 (vision, stairwell or cliff, proximity, wheel encoder or other odometry).

Higher level planning is not always necessary, but can be handled by specific controls that influence or direct the behavior based systems. As shown, the behavior bases systems normally intervene between planning routines 6A-2 and actuators 6A-4. Long-range navigation, as discussed herein, will move the robot from room to room as discussed herein, or alternatively using path planning. A mapper may build maps, which may or may not be "Cartesian" spatial maps (most of the routines, techniques, and disclosures discussed herein do not rely upon Cartesian or spatial maps). Stereo feature extraction may proceed according to known routines (e.g., SIFT or SURF scale invariant feature extraction) in order to identify landmarks or labels. Some of the necessary records may be stored remotely on a server or database 6A-3.

FIG. 6B illustrates one example of component organization in accordance with at least one of the present embodiments, in which communications or power transmission relationships are denoted by arrows interconnecting various component blocks. In one example, components located generally in the head 16, neck or torso 13, or mobility base 12 may be organized into component clusters E20, E30 and E46, respectively. These component clusters may include various electronic or electrical circuits, such as power supplies, motor controllers, and/or integrated circuits. Preferably, components such as integrated circuits, CPUs, controllers, and communication buses are integrated onto PCB boards; as a non-limiting example, a robot 100 may include three PCB boards, in which an upper PCB board E20 is disposed in the head 16, a middle PCB board E30 is disposed in the torso 13, and a lower PCB board E46 is disposed in the mobility base 12.

In the example of FIG. 6B, non-power signals are preferably transmitted among the upper, middle and lower PCBs via a low-voltage differential serial channel (LVDS), which provides advantages of producing only low levels electromagnetic noise (and having low susceptibility to electrical noise interference), inter alia. Alternatively, a parallel or traditional serial bus (such as RC232) may be employed, or a wireless protocol such as WiFi or Bluetooth, in order to transmit signals between the PCBs.

The lower PCB board E46 includes one or more power supplies E90 and a battery and/or charger E91, in which a power supply channel (which may be a plastic-sheathed copper wire, or any other component suitable for power transmission from the mobility base 12 through the torso 13 and into the head 16) transmits power from the power supplies E90 to the middle PCB E30 and to the upper PCB E20. The lower PCB E46 also includes a pan motor amplifier E401 and one or more drive motor amps E402, together with encoder E403 and proximity sensor interfaces E404, and also a two-dimensional accelerometer E406 and a microcomputer E407 (which may include a microcontroller, a programmable logic array, a digital signal processor, and/or a general-purpose CPU, as non-limiting examples). The lower PCB E46 communicates with proximity sensors 222 (routing such communication to the proximity sensor interface E404), drive motors/encoders 46, and to the pan motor/encoder 314.

Regarding the torso area, various features local to this region—such as the body display panel 18 and speakers S31—communicate with the middle PCB EN. Also, an array of microphones may be disposed on the robot 100 for determining the location of the source of a sound. In accordance with at least one embodiment, a microphone for use in a sound-source locating system (herein termed "Acoustic Magic") preferably transmits a continuous serial stream of octets indicating the direction of current sound. The stream is transmitted by a DSP onboard an Acoustic Magic PCB, through its synchronous serial port, emulating an asynchronous serial signal.

The serial signal is received by an HCS12 on the power board, and the octets may be delivered unprocessed in the packet stream to the CPU board.

On the CPU board, a process receives the signal and decimates it to (as a non-example) 10 samples/second, storing the stream in a shared-memory ring buffer. The decimation is preceded by a single-pole IIR low-pass filter, with a pole at 3 Hz, for example. The buffer preferably records at least the last 5 seconds of observations, each of which are time-stamped with a true timestamp for when that audio sample was actually heard (accounting for any buffering through the signal chain).

The estimated voice location is produced by combining this vector with the speech detector of the recognition system. The speech detector preferably may issue regular callbacks indicating its live status. These callbacks correlate detected speech (compensating to true real time) with the 10 hz voice location samples, to produce the estimated direction vector to the most recent detected utterance. These utterance direction vector samples are similarly recorded in a shared memory ring buffer, for use by the user-location and interaction system. Such functionality and processing is preferably provided by an array processor E301 disposed on the middle PCB EN.

In the head area, various sensors such as a pyro sensor S21 or touch sensor S22 may communicate with the upper PCB E20, as well as the right and left image sensors (cameras, etc.) 28, 29, and the face matrix panel 26. The tilt motor/encoder 340 also is connected to the upper PCB E20.

Within the upper PCB E20, components corresponding to devices disposed in the head 16 may be integrated onto the PCB board, such as: a face controller/interface E210, for interfacing with (and/or controlling) the face matrix panel 26; audio codecs/amplifiers E211; and/or Ethernet E202, USB E203, or infrared (IR) E204 interface components for communicating according to their respective channels. Further, the upper PCB E20 may include an embedded microprocessor E230 (preferably consuming less than 1 Watt per hour) and a memory E209 comprising volatile and non-volatile sections, for providing necessary instructions to coordinate and/or control the various subcomponents on the upper PCB E20.

In addition, the upper PCB E20 in the head 16 may be connected to an antenna E201, such as a cellular-band antenna for use with a CDMA modem, in which the antenna E201 includes an embedded antenna component mounted on a PC board. As an advantage, such components are designed for cellular handsets, are small, precisely manufactured and impedance-matched, and easy to integrate. Further, the antenna design may alternatively use simple wire dipoles to additionally reduce cost.

Preferably, a dipole design is implemented directly on the upper PCB E20 in the head 16. One example cellular modem slot supports modules operating in the 800 mHz cellular band, specifically the transmit band from 824-849 MHz and the receive band from 869-894 MHz. The robot's head 16 may be selected to be large enough to accommodate a half-wave dipole for these frequencies, which is nominally 163 mm long. However, if many other mechanical and electrical components are packed into the head, the antennas may alternatively be mounted horizontally. As another alternative, an "inverted V" configuration may be used, which is a horizontal dipole, extended slightly (by approximately 4%, for example) and bent in the middle. The inverted V has the added advantage of a more uniform omnidirectional response pattern.

A preferred configuration places two "inverted V" dipoles, mounted at the top and bottom of the head for spatial diversity. Each dipole has two legs, each preferably 85 mm in length, 2 mm in diameter. The calculated VSWR for this configuration may range from 1.7 at 824 mHz, 1.2 at 860 mHz, to 1.7 at 894 mHz. These antennas may be implemented with (for example) 12-gauge wire segments affixed to Plexiglas supports placed behind the CPU board, in which case 50-ohm coaxial cables can connect the antennas to the CDMA modules.

Figure 6C:
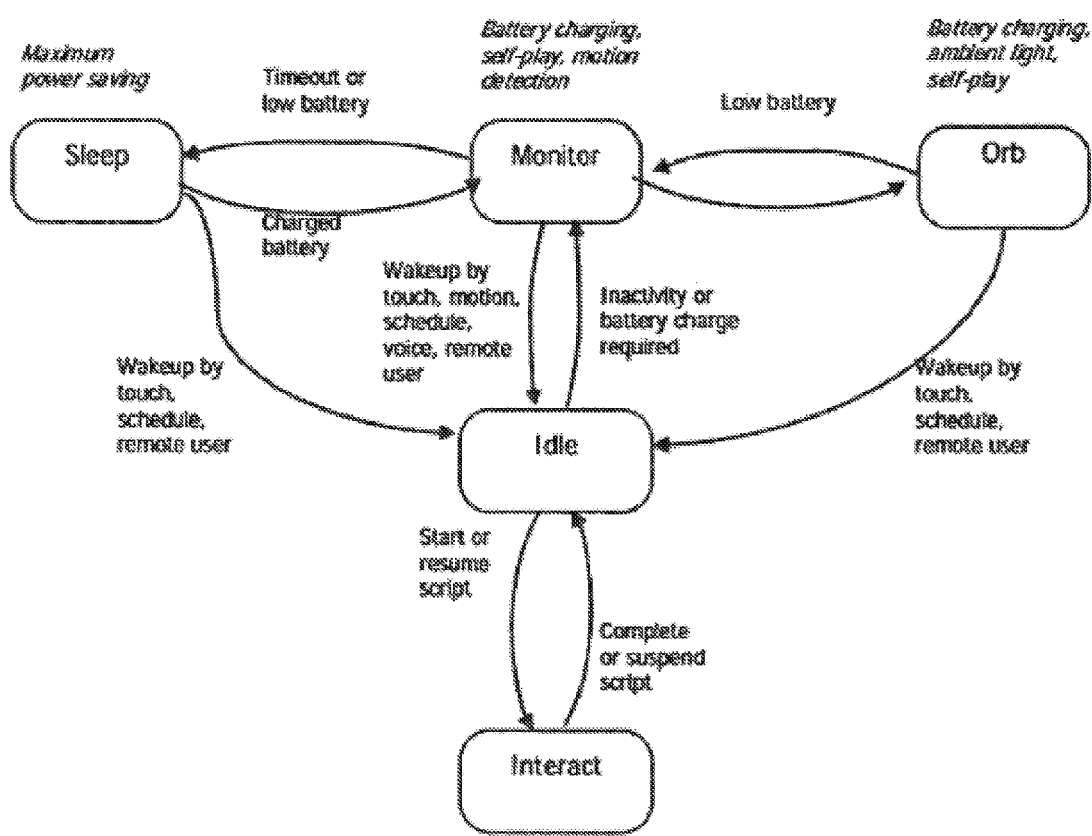
FIG. 6C is an interaction state diagram for a mobile robot in accordance with one embodiment of the present disclosure.

FIG. 6C shows transitions between levels of activity in a robot during a day. Not all of these states are necessary in every robot discussed herein. Nor need there be divisions as shown. Largely, these states are useful for power conservation. In a Sleep state for maximum power saving, in which the robot neither "listens" nor "observes" its surroundings (e.g., camera and microphones are disabled, Sleep state may also be considered a Privacy Mode) the robot may enter an Idle state (from which it may begin an interaction script or other activity) upon some external or internal stimulus event. If the battery is fully charged, the robot may rest in a Monitor state rather than a sleep state, and may enter the Idle state upon any event detection, including sound, heat; or observed or detected motion. The robot may move from Monitor to Sleep state in a low battery charge condition or when no sound or motion is detected for a certain period, e.g., 10 minutes. Changing from Sleep state to Monitor state may be prevented without express permission. Similarly, the robot may enter the Monitor state from the Idle state in circumstances of inactivity or charge required. The Orb mode is a condition where the robot illuminates the area around it.

Figure 6D:
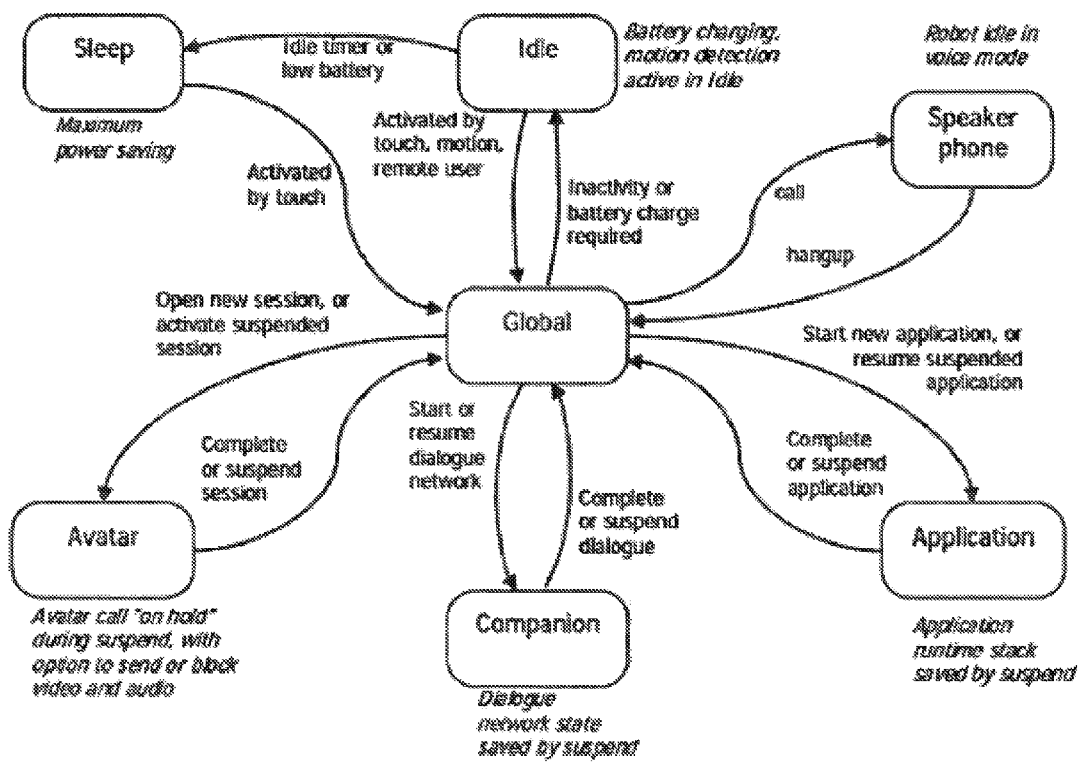
FIG. 6D is an interaction state diagram for a mobile robot in accordance with another embodiment of the present disclosure.

FIG. 6D shows transitions between different functions in a robot during a day. Not all of these functions are necessary in every robot discussed herein. Nor need there be divisions as shown. The Sleep function and Idle function are similar to the states as discussed with reference to FIG. 6C. If the battery is fully charged, the robot may rest in a Global (Ready) function ready to undertake other functions, rather than a Sleep or Idle state, and may enter the Global function upon any event detection, including sound, heat, or observed or detected motion. The robot may move from Global to Avatar function. In the Avatar function, a teleconferencing, teleoperation, or remote presence session may be started or activated from suspension. In a Companion function, a dialogue as discussed herein may be started or activated from suspension. In an Application function, any application that is storable in a suspended state by saving a runtime stack may be started or activated from suspension. In a Speaker Phone or video chat mode, the robot may start or activate a call.

Figure 7A:
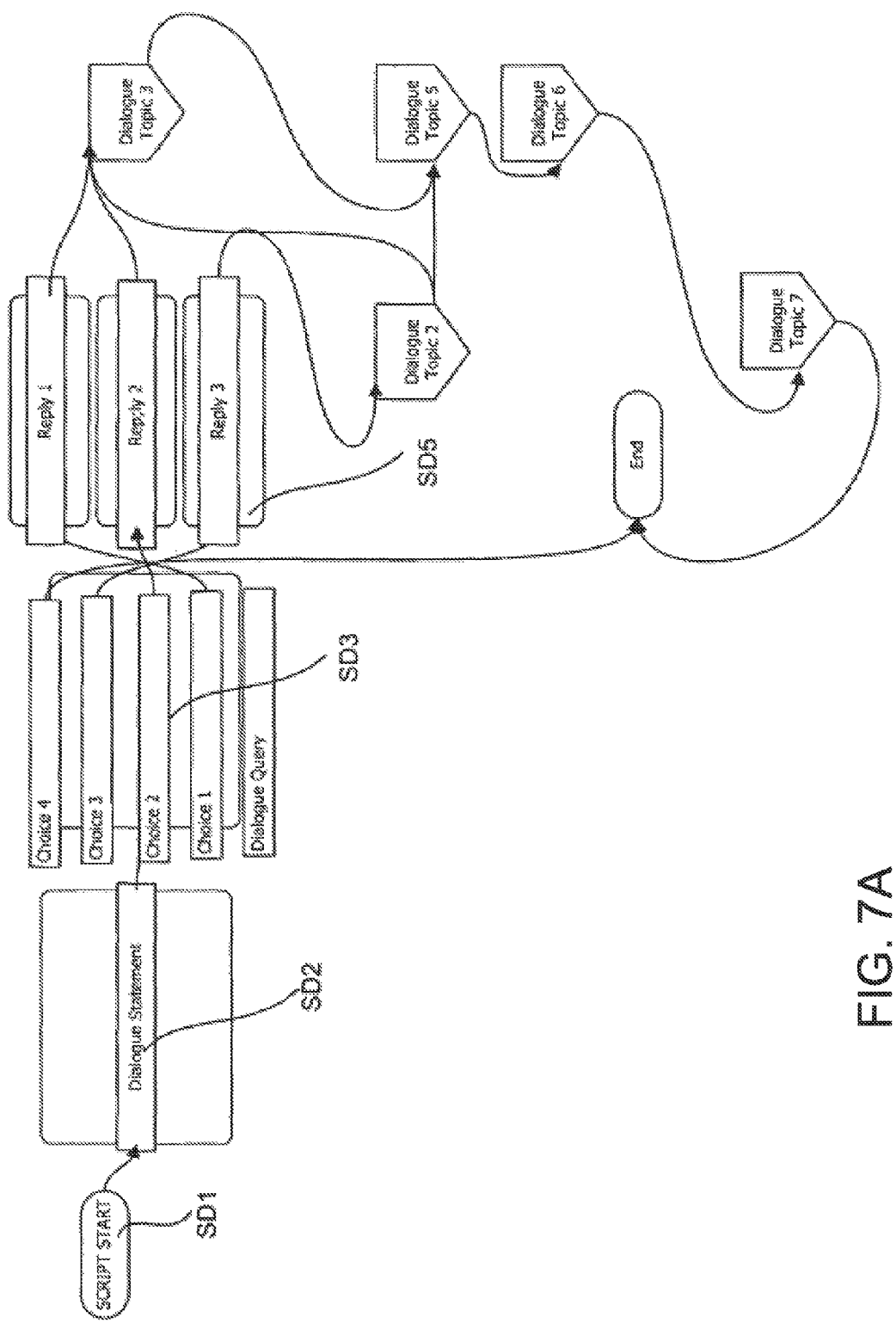
FIG. 7A depicts a generic interaction algorithm in accordance with one embodiment of the present disclosure.

FIG. 7A depicts a generalized dialog routine that may be used by a robot of the present disclosure for natural, flowing communication. Step SD1 initiates a Start Sequence, where the robot may select one of various conversations or dialogs to engage in with the resident. The sequence may be selected based on an occurrence of an event or time. For example, the robot may initiate a greeting sequence when the resident returns home, or may ask the resident if they have any plans for the evening after a meal occurs. Additionally, the robot may generate sequences at random, to increase contact and bonding opportunities with the resident. The robot may approach the resident and inquire if the resident may be interested in playing a game stored on the robot, asked to be picked up, etc. Additionally; the dialog sequence need not occur between the robot and resident, but may include the robot talking to itself. In one example, if the robot bumps an object while moving in an environment, the robot may begin a sequence expressing surprise or frustration.

Step SD2 represents a first interaction, which, depending on application, may be a greeting to the resident, an audible comment to itself, etc. At Step SD3, the robot may ask the robot a question or make an affirmative statement, "How was your day?", "Got plans tonight?", "You asked me to check movie times for you.", etc. The question be designed specifically to elicit one of a specific number of responses from the resident, or the resident may respond to an open-ended question or statement. A Response X (outside the robot's library of anticipated responses) may cause an error, confused, or other reply from the robot, Step SD, causing the robot to end the interaction or pose the question or statement again, Step SD3. Predetermined or expected responses may initiate corresponding replies, Step SD5, from the robot. These replies may include a matching affect responses as well; e.g., an audible "Wow" with an affect indicating surprise, an audible "That's too bad" with an affect indicating concern, "Sounds great" with a happy affect, etc. Alternatively, the robot's response may be a second question. For example, if the robot asked the resident which movie the resident would like to see, the robot could then ask if the resident if the robot should search for theaters showing that movie, and so on.

After the robot's reply at SD5, the robot may begin a number of second interactions, at Step SD6. For example, the robot may begin playing a game with the resident, move on to a second, more specific line of questioning or interaction, or end the interaction in view of particular responses. Certain interactions may lead to other interactions. Under these circumstances, the robot may interact with the resident for long periods of time, changing topic, activity, or task, as the circumstances demand, creating a rich interactive experience for the resident.

According to these routines, the robot may conduct an effective method of human-robot interaction. Most fundamental motion behaviors are asynchronous (or independent of) the dialogues. Behaviors such as escape or safe reactions to events are not affected by the dialogue. The communication script segments (queries, choices, replies) are received by the robot from its internal database or a remote database, and include the dialogue branches with robot speech prompt text (such as dialogue queries, replies, and confirmation/feedback responses) as well as human response text (such as the choices for the person to repeat or select). The robot interprets the communication script segment to generate an audible robot speech prompt, either by referring to recordings; by consulting a speech synthesis phoneme script that goes with the text; or by having on-the-fly text-to-speech synthesis (each of these being capable of including script or timestamp synchronized viseme tags defining facial animations, earcons defining emphasis sounds, or "animotion" scripts defining robot emphasis motions). Animotion scripts tend to define a desired expression during the communication script segment by adding an expression motion, usually one or both of a head movement sequence including nod axis head movement or turn axis head movement, or a robot movement sequence including movement of the entire robot.

The robot receives input in the form of either recorded speech from the person via its microphone array, or the result of a push-button or touch-screen identification of the selected response choice. If at any point during this dialogue, the robot detects an event that requires a response from the behavioral system (e.g., in moving into an expression motion, the robot bumps a table or other obstacle, or has moved partway toward a second person), the robot interrupts the dialogue branch in response to the event detected by one of the plurality of behaviors (i.e., via the sensors used by those behaviors) to execute an asynchronous response (such as stopping the robot). After any appropriate asynchronous response (including a further comment from the robot regarding the change its motion or pose, or what was discovered that caused the change and asynchronous response), the robot recovers the dialogue branch after the execution of the asynchronous response. The robot interrupts expression motion(s) in response to the event detected by the robot. The robot is stopped (or other corrective behavior) to reposition the robot according to the event.

FIG. 7B depicts a dialog routine constructed using the generic routine of FIG. 7A. At Step SD1', the robot begins a greeting sequence, triggered when the resident returns to the home at a time that the robot recognizes as the conclusion of the workday. The robot welcomes the resident home at Step SD2', then asks about the resident's day at Step SD3'. In this case, for example, the robot may combine the question of SD3' with a display on it's input screen of the question and potential responses (in this case, "Great," "OK," "Terrible," or "I'm in a rush"). A number of robot replies are depicted at Step SD5', or the robot may end the dialogue if the resident has no time or interest to interact with the robot. At Step SD6', the robot may begin a number of other interaction sequences, such as asking the resident about the day's or a future day's work, remind them of scheduled events, advise them on the importance of getting a good night's sleep, etc. As indicated, interactions may lead to other interactions, questions, etc. These interactions may continue indefinitely, until the robot reaches an end point, until the resident requests termination of the interaction, etc.

FIG. 7C depicts a bump interaction algorithm SD10 constructed using the generic algorithm of FIG. 7A. At Step SD11, the robot begins a bump sequence, triggered when the robot bumps unexpectedly into an object. The robot makes a bump sound at Step SD12, such as a beep, crash, or other sound to signal contact with an object. The robot then initiates a bump analysis sequence SD13, to determine the frequency of the sensor events (in this case, contact with the object). For example, the robot may contact an object a single time, as in Step SD13$a$, or several times in a pre-defined period, as in Steps SD13$b$ and/or SD13$c$. The decision making as to the expressions, SD14, that the robot uses depend on the sensor events, but need not effect the behavioral response of the mobility response. In other words, the robot may output any expression, sound, affect, etc., but these are independent from the robot's behavioral mobility system (e.g., the robot may back up, if required, while expressing frustration). In addition to outputting an audible (via its speaker) or visible (via its display) expression, SD14$a$, the robot may also utilize other animations or sounds, SD14$b$. By utilizing its mapping function, the robot may also determine if it has hit an object at other times in the past in this particular location, Step SD15, and thus learn to avoid areas where it has experienced mobility problems. The POP step allows the robot to exit the bump interaction sequence. Similar to the dialog algorithm of FIG. 7B, this bump interaction may lead to other interactions, cause pleas or questions directed to a nearby resident, etc. These interactions may continue indefinitely, until the robot reaches an end point, until the resident offers assistance to the robot, etc.

Figure 7D:
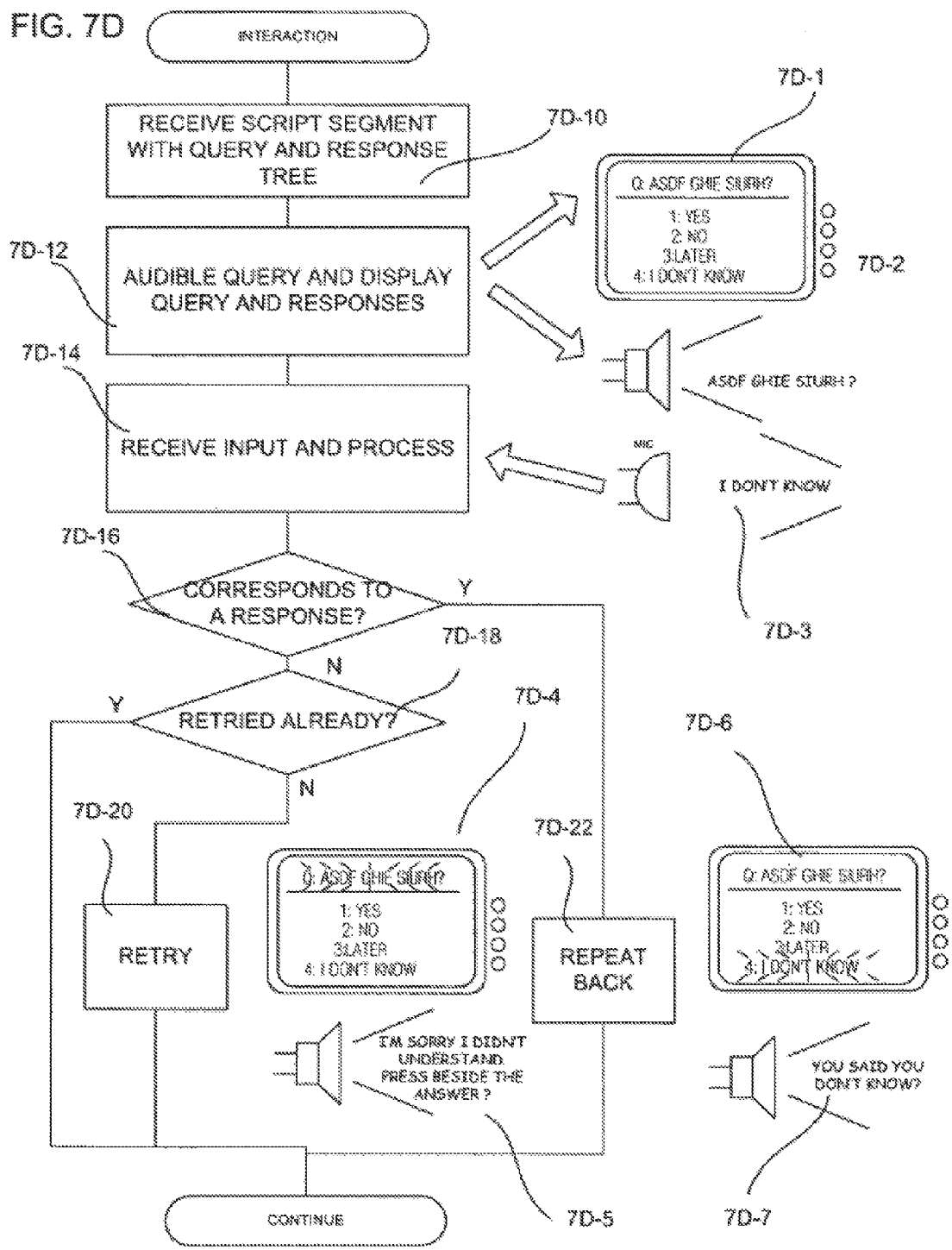
FIG. 7D depicts an interaction algorithm utilizing a combination of voice prompts and responses with display backup in accordance with one embodiment of the present disclosure.

FIG. 7D depicts a routine for the robot to present a question to the resident, with a limited number of responses (five or less, usually three), and in which most of these responses are confined to simple affirmative, negative replies. At step 7D-10, the robot retrieves or receives a script segment from its own database or a remote database, the robot may carry all dialogues or common dialogues on board, but other embodiments may also retrieve dialogues from a remote server, on an ad-hoc basis (as a rarely encountered dialogue tree is explored) or on a predictive basis (retrieving or some all possible branches in a dialogue tree ahead of the speed at which the resident is moving through them), or as part of a scheduled or on-demand update procedure. As explained above, the robot then "speaks" an audible query or question (step 7D-12 and shown at 7D-2, from recording, phonemes, or text) and at the same time displays the corresponding question in text (using a screen as shown at 7D-1, optionally highlighting each word of the query sentence as it is pronounced or the query sentence at one time) as well as the answers the robot expects to hear as subsequent branches in the scripted dialogue tree.

Subsequently (step 7D-16), the robot attempts to receive an audible response and process it. FIG. 7D does not show processes for robot behavior in the event that no response is detected at all (e.g., the resident has walked away, the resident for some reason does not to speak at all), but such processes would be compatible with this routine. In addition, should the person reach across and press a button or touch-screen beside the displayed choice as a way of answering the question, the process of FIG. 7D would move immediately to step 7D-22 noted below (confirmation repeat of the selected choice). The processing in this case is speech recognition, but the set of potential responses is limited to those shown on the screen (one exception is the affirmative, negative response, which may have a larger set of possibilities). The resident may choose to read the response text out loud from the screen; may have memorized the typical responses as a result of frequent use, or may choose to input using touch screen or soft buttons. As shown in the diagram, numbers may also be displayed (and recognized), but the robot would not necessarily explain on every occasion that a number may also be spoken and recognized. The choices and thereby the processing is limited such that the speech recognition may be done on an embedded-class processor of less than 1000 MIPs, shared with all the remaining tasks and computation necessary for robotic operation. If more speech recognition resources are available, they may be devoted to a higher success rate rather than a more versatile recognition set.

As shown in FIG. 7D, the robot provides the resident with a designated number of "retries" (one shown) at steps 7D-18, 7D-20 if speech analyzed and processed is not recognized as one of the expected responses in the dialogue tree at step 7D-16. A retry message may be spoken shown at 7D-5) and the question itself or possible answers may be highlighted or blinked together or sequentially (7D-4) to attempt to refocus the resident's attention. If, on the other hand, the speech analyzed and processed in step 7D-16 is recognized, the robot may confirm this at step 7D-22 with audible repeat-back feedback (shown at step 7D-7) and/or by highlighting or blinking the recognized answer at (shown at 7D-6).

In this manner, the received (from database) communication script segment includes an output query sub-script text and a response tree of five or less sub-script response text candidates (often "yes", "no", and an alternative such as "I don't know"; on other occasions a list, e.g., pill type "red diamond", "green", "white", "none of the above"). The list is kept at five or less so as to (1) avoid overwhelming attention; (2) avoid overwhelming display screen "real estate," (i.e., no scrolling, text large enough for easy review) and (3) limit the resources necessary for speech recognition. The output query text (i.e., the questions asked) are related to or associated with an audible output signal (e.g., phoneme codes, compressed recorded audio), and output as a spoken query to a person. Both the output query sub-script text and the limited number of responses are displayed together on a display of the robot. The robot receives, via a microphone or a vectoring or other microphone array, the person's spoken response as an audio input signal, which is processed to check/recognize if it corresponds to what has been displayed (i.e., all the responses expected to the question). If the signal recorded by the microphone is recognized, the robot issues an output signal (i.e., a voice or text confirmation, highlight, or blinking) to feed back or repeat back the recognized response. If not, an output signal, also a voice or text reprompt, highlight, or blinking prompts the user to retry communicating a response. In some cases, the robot can request confirmation from the resident by monitoring for a confirmation of the correctness or incorrectness of the recognized choice.

In the event that audio reprompting is ineffective, the reprompt can take the form of highlighting (including blinking or the like) the displayed sub-script text on the display of the robot, and at the same time receiving the response choice via a manually operated control (e.g., soft button, touch screen) associated with the display. There is some advantage if two of the response text candidates are a simple affirmative and simple negative response, and if the processing then checks for speech corresponding to many different kinds—a family—of affirmative responses equivalent to the simple affirmative response (yes, yeah, oh-huh, sure, etc. or includes speech corresponding to a family of negative responses equivalent to the simple negative response (no, nope, nah, don't think so, uh-uh, etc.). Other messages can be common among many scripts (I don't know, please go back, etc), and in such cases, the robot may recognize a limited set of possible responses that are not shown on the screen lease go back, come back later, quit, etc., show me my schedule). If there is no yes or no answer, the list of answers may be limited to three or less to significantly limit speech recognition work.

A standalone network adapter provides firewall circumvention and zero-configuration of network access for the robot, without requiring a user-interface for configuration. This may be done independent of the robot and, in certain embodiments, can potentially bridge multiple robots in the home. In one embodiment, WiFi is an non-broadcast extended service set identifier (ESSID), with wired equivalent privacy/WiFi-protected access (WEP/WPA) enabled by default and "locked". The robot and network adapter may be paired at the factory with generated, unique security information. Additional pairing operations performed at a later time may require physical proximity or line of sight between the robot and network adapter (as verified by pairing cable, by short range RF such as BlueTooth, ZigBee, Wireless USB, or by short range IR. The network adapter functions as a firewall and may be into outside any existing infrastructure. It also includes "Simple Traversal of User Datagram Protocol (UDP) Through Network Address Translators (NATs)," as defined, for example, in http://www.faqs.org/rfcs/rfc3489.html, the disclosure of which is hereby incorporated by reference herein in its entirety. This functionality may be embedded into the device, thus allowing the network adapter to act as an Internet gateway, granting Internet-access to recognized robots in a home environment. There are a number of ways to access the firewall circumvention features of network adapter, for example, by the robot having a MAC address within a known range.

Figure 8A:
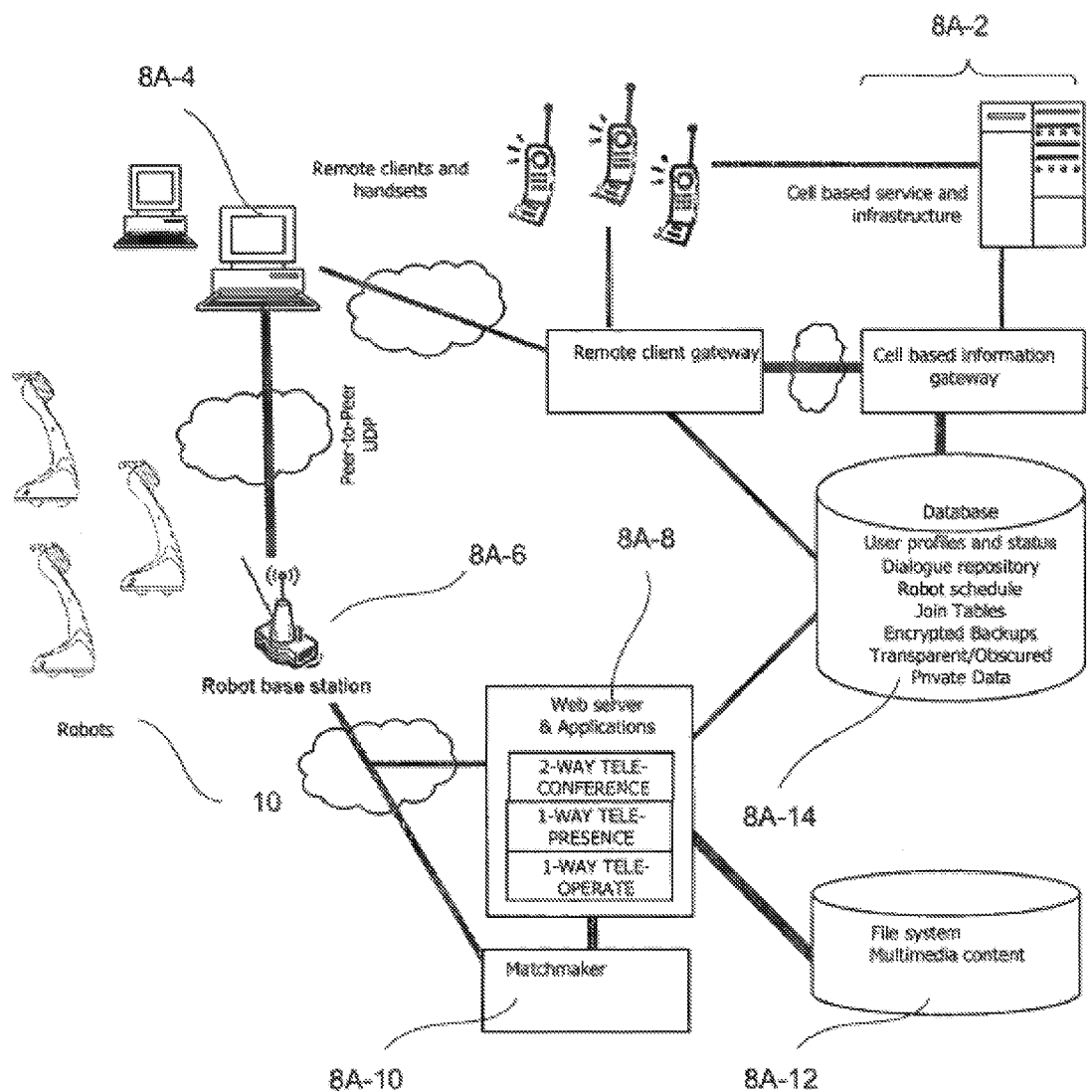
FIG. 8A depicts a networked server for a mobile robot in accordance with one embodiment of the present disclosure.
Figure 8B:
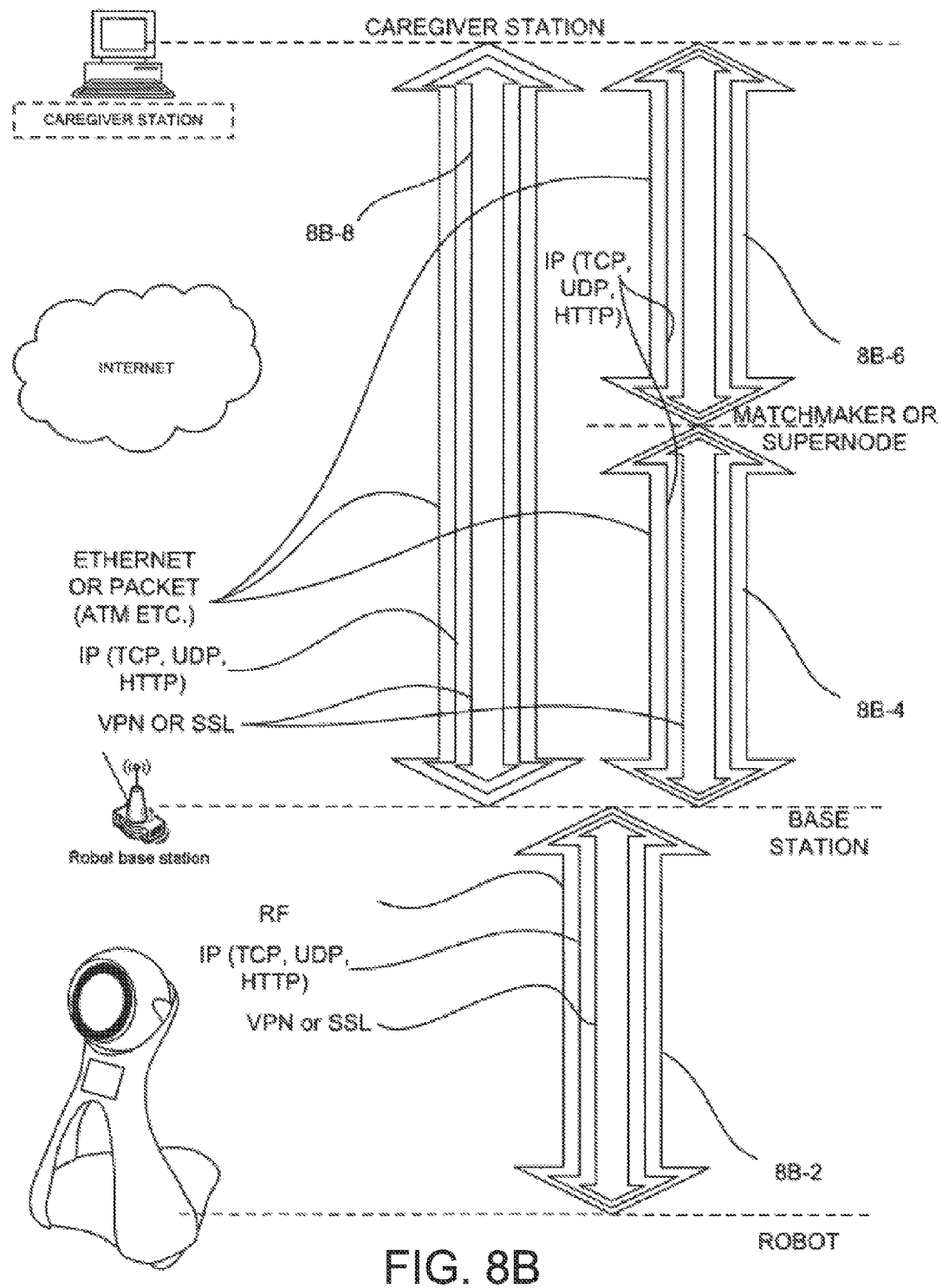
FIG. 8B is a schematic diagram of network protocols, security, and transport layers in accordance with one embodiment of the present disclosure.

General enabling network architecture is shown in FIGS. 8A and 8B. Each robot 10 in a home (multiple robots or other embedded devices with access to the robot base station possible) is linked to the robot base station via different levels of pre-installed security and compatible cryptographic keys. As shown in FIG. 8B, the connection 8B-2 would generally be carried in frames or packets of an RF protocol, would use IP stack protocols within this (TCP, UDP, HTTP), and would have a trust boundary within this (a virtual private network VPN or secure socket layer SSL boundary). Generally, the robots 10 are wirelessly connected, and the robot base station is an RE station using an RE bandwidth and protocol sufficient for the data that will be sent to and from the robot 20. For example, for a robot 10 capable of videoconferencing, a relatively high bandwidth RF modality such as 802.11a/b/g/n would be useful. For a robot 10 which does not transmit video or audio data, Bluetooth, wireless USB, or proprietary networks could be used. The base station can be configured to add encryption to the RF protocol (to limit access to the network), or without (to permit the highest speeds). Whether or not the RF protocol is itself encrypted, the innermost trust boundary encrypts and protects data that can be sniffed from the RF signal; and robots and other authorized devices are on a media access control MAC connection-permitted whitelist, and/or are provided with appropriate public and private cryptographic keys for the VPN or SSL connection. The base station 8A-6 may also provide general RE-protocol or WiFi network connectivity for other devices in the home; and the robot(s) (especially if provided with two transceivers) may act as relays or repeaters to extend the range of the base station 8A-6.

The base station (in this view; 8A-6) is always connected via a modem or network terminal (usually a cable modem, xDSL, or optical network terminal) to a (usually broadband) Internet Service Provider (not shown) and then to the public internet (cloud). The robot base station generally has the functionality of and provides a router (e.g., DHCP server, NAT, firewall, etc.) so does not need to traverse a router. Nonetheless, as described herein, in some cases the robot base station 8A-6 will be behind a firewall or NAT service, and some techniques for matchmaking are addressed herein.

The robot base station 8A-6 regularly or intermittently connects to a matchmaker 8A-10 (a web or database server), which maintains up to date records of the current IP address of the robot base station 89A-6 (assumed to be, in most cases, dynamically assigned). Once a match is made (i.e., a caregiver station 8A-4 and robot base station 8A-6 are informed of each other's IP address), a secure peer-to-peer connection (as shown in FIG. 8B, connection 8B-8) is established The matchmaker 8A-10 may not be necessary in an IPv6 regime with ubiquitous unique IP addresses. As shown in the right side of FIG. 8B, the base station knows the address of the matchmaker or supernode, and connects 89B-4 via protocol layers similar to the robot-base station connection 8B-2, except that the outer layer in this case would be protocols appropriate for whatever medium carries internet traffic from the base station to the matchmaker (e.g., Ethernet, ATM, X.25, or other packet network). The matchmaker 8A-10 or supernode informs the caregiver's station of the IP address of a matched robot or robots 10.

In addition, the matchmaker 8A-10 may be part of a network which relies upon so-called supernodes to provide routing among privileged clients, or the matchmaking function may be handled by a network of nodes and supernodes which do not have any access to the data network 8A-8, 8A-12, 8A-14. For example, supernodes may be nodes with a public or fixed IP address, not behind a firewall. Cryptographic keys for user identity and password are stored on the matchmaker 8A-10 as a login server. Each robot base station or caregiver station may use a protocols similar to STUN (rfc 3489) protocol and TURN protocols to determine what kind of NAT or firewall intervenes. To initiate, the station may open (TCP or UDP) listening ports at a random port number and specific common port numbers (80 for HTTP and 443 for HTTPS). Each station may maintain a cache of supernodes or matchmakers and their IP addresses and known random ports. Upon connecting to the internet, either station may send packets (TCP or UDP) to a supernode or matchmaker IP address at the historic port number, await a response, then try to connect on the HTTP port and then HTTPS port. After being connected to the supernode or matchmaker, this matchmaker or another matchmaker, Web server or security server may authenticate the station. The supernode or matchmaker may also exchange sufficient packets to inform the station of the IP address of a different matchmaker or the address of a particular login authority that can authenticate that station. During a connection, each station may populate its cache with supernodes, nodes, matchmakers and their last known (random) open ports and IP addresses. Any node (robot base station, caregiver station) or supernode may act as a router to forward and route traffic between a matched robot base station or caregiver station if either or both are behind port-restricted network firewalls or NAT. This is typically similar the "Skype" peer to peer telephony network, and would be capable of interoperating with such a network. In the present arrangement, preferably, idle caregiver stations (typically ordinary PCs running authorization software, VPN, and/or client software) act as routers in such cases, as this would tend not to burden the supernodes, and also would avoid using robot base station nodes which would typically have less processing capability (i.e., about the same as a consumer router).

As shown in FIG. 8C, using this or a modified system, authorized devices such as robots or pre-authorized devices such as a VOIP phone or media station (i.e., that have cryptographic or unique identity information known to the robot base station, such as a MAC address, public key, signature, or that can transmit this information locally over a direct wire connection, scannable ID, serial connection, and the like) can be permitted by the robot base station to immediately participate in at least part of the trusted network (s). The base station will permit an authorized device trying to become an identified node to listen on a random port nn, which will notify the matchmaker that the device is available at that port (i.e., including the IP address assigned to the robot base station, the port that is being listened upon, and identity and/or security information associated with the robot or pre-authorized device). In other cases, no identity information is necessary, as each device accessing via a base station will have a different random port. The matchmaker and robot/device will then conduct challenge-response (including security; authorization information) to authenticate the robot/device at the matchmaker. If an unauthorized device tries to use the base station, the device may become authenticated by negotiating its authorization via the base station and a list of authentication servers (e.g., registering by sending a signed and/or pre-authorized privilege code, already known to the authentication servers, via the base station). Thereafter, the device or robot may be authorized at that base station. The same process may take place at a caregiver station, except that a caregiver station would immediately attempt to connect to a supernode or matchmaker. In addition, the random port strategy may be supplemented by using an HTTP port, HTTPS port, and/or intervening node packet forwarding and routing when either the robot base station or caregiver station are behind a firewall, closed ports, and/or NAT.

The base station 8A-6 is also connected to a Web server or server 8A-8 which hosts various applications useful on the robot 10. The Web server 8A-8 has access to a file system 8A-12 with content to be used by the robot 10 (e.g., multimedia content); and also to a generalize database. The database may store user profiles for the residents, the dialogues available for robots 10 to use, schedules and the like. Any data considered confidential or sensitive can be obscured as to identity or content by cryptographic keys. Data may be used or processed by the database in a manner that the database owner (not the resident) may not inspect or attach an identity to private date. Join tables can match records stored on the robot or base station with data stored by the caregiver, so that data collected or sent from either while the other is not on-line to connect peer-to-peer 8B-8 may be associated. Data normally preserved only on the robot or by the caregiver or caregiver's network (confidential medical history and records, etc. may be maintained on the database 8A-14, but preferably in an encrypted backup form that is recoverable only by one of the caregiver, robot, or robot base station or a proxy (e.g., the resident's home PC).

In this manner, a robot system, includes both the base station 8A-6 and robot 10. The base station includes a wireless transceiver capable of communicating TCP/IP transmissions over a local wireless protocol and a wired Ethernet connector for communicating TCP/IP transmissions over a local wired Ethernet accessing the Internet. The access point circuit (e.g., in the robot base station) transfers TCP/IP transmissions between the local wired Ethernet and local wireless protocol, and is limited to a predetermined IP address assigned to and locked to the robot (e.g., cannot be changed by a resident or caregiver without authorization, or at all), predetermined shell level encryption locked to the robot (such as the discussed VPN and/or SSL), and predetermined ports to the Internet open only to the robot, (e.g., one random port assigned to each robot and opened, or under the same language, a common port such as HTTP or HTTPS in combination with an intervening random routing node). The robot itself would include a wireless transceiver capable of communicating TCP/IP transmissions over the local RF or wireless protocol and a client circuit (e.g., CPU and OS with IP protocol stack) for transferring TCP/IP transmissions over the local wireless protocol.

Preferably, the robot base station includes a plurality of antennas (the robot may also), and makes use of 802.11n multiple-in, multiple-out antenna diversity and selection to overcome issues of multipath propagation within the home, not limited to 2.4 GHz unlicensed frequencies, but in bands from e.g., 900 MHz up to around 10 GHz. Further preferably, the robot base station further encodes wireless transmissions using orthogonal frequency division multiplexing. In such a case, the robot base station may be portable and incorporate elements of the caregiver station (such as a screen capable of relaying camera and video information for teleoperation, and a controller for teleoperating the robot), and the embodiments contemplate that the platform for the robot may be treaded and skid steered, with surveillance cameras on board. Video is transmitted from the robot to the base station at the highest possible speed, multipath resistance, and frame rate using multiple-in, multiple-out antenna diversity, orthogonal frequency division multiplexing, IP or IP-compatible packet protocols that do not error correct (like UDP), and optionally predictive wavelet based video compression like H.264AVC or MPEG 4.

In the embodiment depicted in FIG. 8, the robot authenticates via a challenge-and-response exchanging with an upstream server. The network adapter opens a small hole to a known authentication site for unrecognized robots in the home. This authentication site issues a challenge to an unrecognized robot. If robot responds with a cryptographically correct response, an authentication token is sent to the network adapter, which stores the token and allows access from that point to the Internet. In still another embodiment, the robot is granted a random port number to listen to, and this information is also forwarded to the matchmaking service.

A central service may provide a matchmaking similar to dynamic DNS services, but for commercially available robots that utilize the particular network adapters. Under these circumstances, each robot would be shipped to a consumer with a unique pass code to map the owner to the device when the owner first connects to the matchmaker service. In this case, the matchmaker service is web-hosted centralized user interface for robots. Service proxies configuration and user interfaces between robots and users, who are both Internet clients. Additionally, the matchmaker service may operate as a fleet management tool (for software updates) and a portal for the robots in a particular home. From this central site, a user can "connect" to a robot, which redirects the user to the user interface hosted on the robot.

Figure 9A:
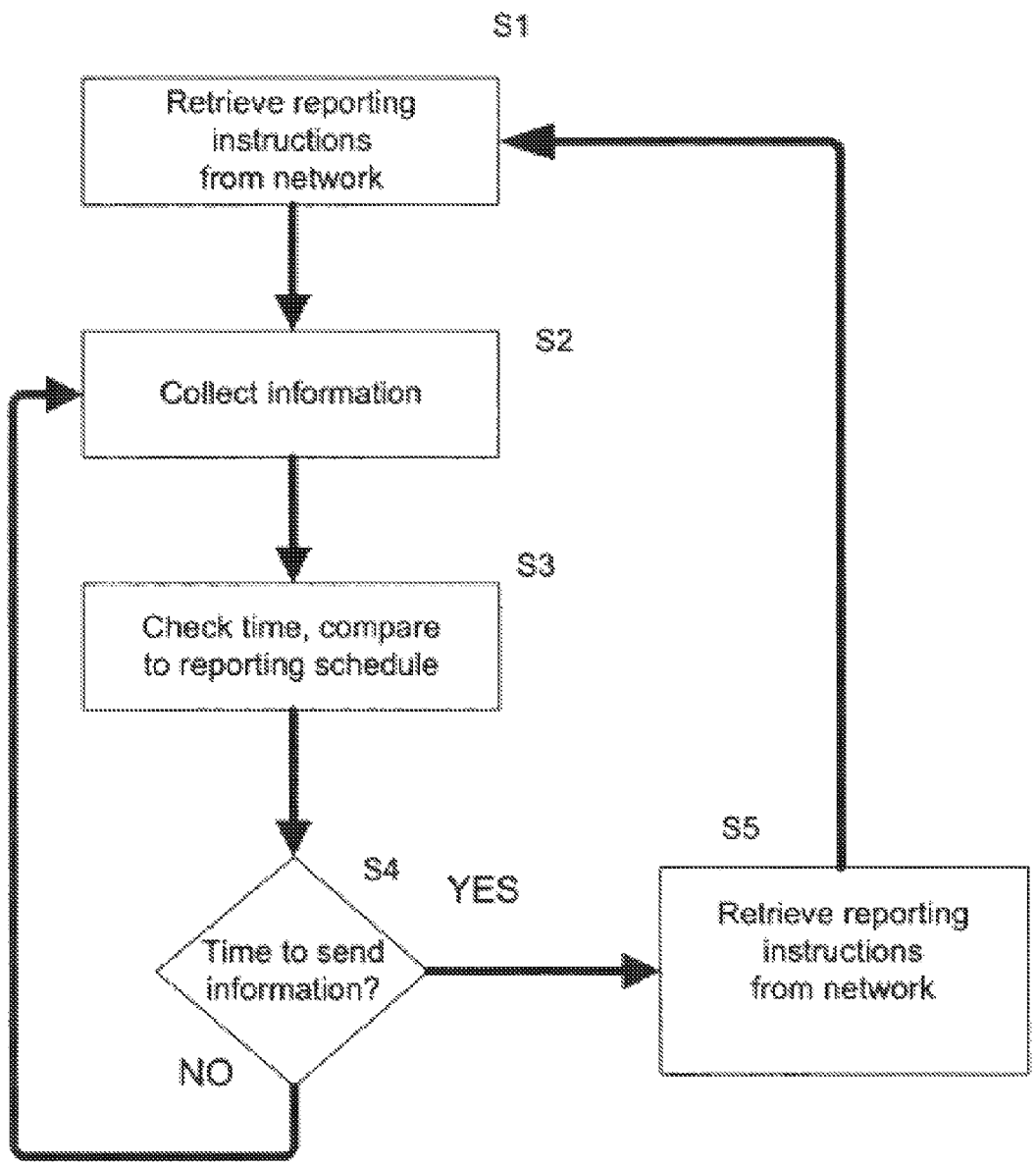
FIG. 9A is a reporting procedure algorithm for a mobile robot in accordance with one embodiment of the present disclosure.

FIG. 9A illustrates a reporting routine which may be implemented by a mobile robot in situations where safety concerns require transmission of information to a remote terminal (a base station, caregiver computer, etc.). At step S1, the robot retrieves reporting instructions from a computer network—for example, by downloading a list of information that a remote caregiver wants to receive from the mobile robot. Such information may include, among other things, what time is the robot last detected the presence of the resident, whether issuance of medication to the resident succeeded, etc. At step S2, the robot may collect such information. The robot then checks the current time and compares it to the schedule at step S3; and, if it determines that the scheduled time has come to transmit information, at S4, the robot may transmit the information to the remote terminal at step S5. Otherwise, the control may return to step S2, for example.

In response to schedules or events throughout the day, the mobile robot generates updates including updated information regarding the resident, including but not limited to: (a) medication compliance information; (b) presence or absence of the resident, recognized by patterns of sound or other detections; (c) status or "nothing unusual" reports; (d) reports of visitors; (e) updates entered by the resident as to their planned schedule ("I'll be out for two hours"); (f) report of unusual patterns of sound (distress noises, calling out noises) or unusually loud sounds; (g) requests for communication from the caregiver or other family members to the resident. These updates include event-responsive updates, data-change updates, status updates, and scheduled updates.

The robot uploads the update information to the computer server, which is integrated with or in communication with a push server, using a push updating system. The push server, similar to a mail delivery agent, sends (or pushes) newly received updates to the update client, similar to a mail user agent. Both the robot and caregiver's terminal may be an update client. The push server monitors the network of robots and caregiver clients, and when it sees a new update for a caregiver, it retrieves the update and pushes it to the caregiver's terminal. Similarly, when the push server sees a new update for a robot, it pushes the message to the robot. The updates may or may not be separately maintained and archived.

Figure 9B:
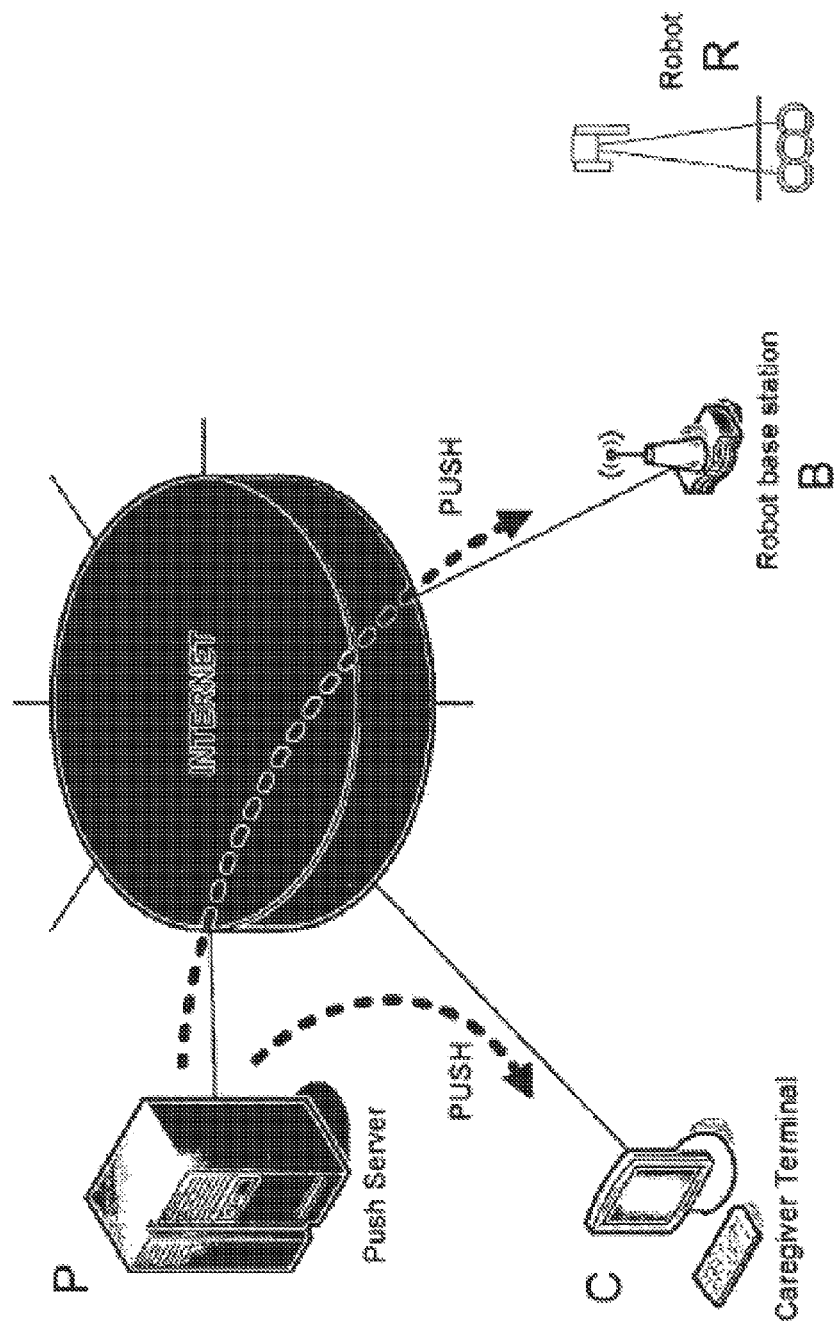
FIG. 9B is a communication system for a mobile robot in accordance with one embodiment of the present disclosure.

As shown in FIG. 9B, a push server P provided on the internet I communicates with the mobile robot R (via the base station B) and the caregiver's terminal C in such a way that reports and updates from the robot (which are reported to the push server in client mode by a client robot) are pushed to the caregiver's terminal C. The caregiver's terminal C may be a telephone, messaging device (blackberry or other personal digital assistant), or computer browser or other client. In this context, information being delivered from a push server P to a client device is based upon a predefined set of request parameters outlined by the client device. This can be delayed or in an instant messaging fashion. The push server P pushes content to the caregiver's terminal C, without the caregiver's terminal C polling or otherwise requesting updates from the push server P. As a result, the information updated by the mobile robot R is relayed to the caregiver's terminal C via the push server P on the Internet I. The push server P may push updates as well as e-mail. Alternatively, pull technology such as RSS may be used for delivery of robot-originating content. In such a case, the caregiver's terminal C may automatically retrieve any updated information from the computer server, for example, at particular intervals during the day.

The robot of the present disclosure provides a rich interactive experience for a user by utilizing visual cues to indicate its responses to certain events. Those cues include, at least, image displays on one or more of the screens and head or other physical movements to convey reactions. FIG. 10A depicts a number of exemplary affect expressions to be displayed on a screen 26 of a mobile robot. Although the affect images depicted in FIG. 10A are shown on the display 26 of head 16 of a robot, affect images could also be displayed on a body-mounted screen. Optionally, the affect images may only utilize a portion of a display screen, leaving the remainder open for other interactions and/or functions.

As displayed, mouth, eye, and eyebrow objects (such as those exemplary expressions depicted in FIG. 10A) can be arbitrarily formed from a multiplicity of pixels using a matrix display, or can be formed in set shapes from a number of segments using a segment display. Of course, a display may incorporate both segments and matrix portions, and matrix pixels may be considered one kind of segment. The segment or facial matrix display may be provided with a sufficient number of segments or pixels by conventional manufacturing techniques.

The following discussion describes either a segment panel or matrix panel, with distinctions noted at appropriate portions. In discussing the matrix panel, terminology used to create animations in Macromedia™ Flash™, a portable animation system, is useful. In this terminology, a "movie" may be a collection of scenes, which is a collection of objects such as text objects and image objects, which in one embodiment may be placed in layers onto a background. The movie and objects are responsive to events, and may apply effects (animations that change the appearance of an object) as well as carry out actions outside the movie. In discussing the operation of a segment panel, an object may be a single segment or group of segments that may be turned on or off in sequence or separately, which can give the impression of motion or a change in appearance. In both cases, "objects" may be animated and accommodate transitional animation states. Notwithstanding the use of this terminology the disclosure is not limited to the discussed animation systems.

The display 26 implements an eyes-nose-mouth display which is animated in sync with speech and interaction to express the changing affect and non-verbal behavior of the robot. The animated expression of the display is controlled subject to a number of variables within the system: non-verbal behavior synchronized with speech, phoneme animation synchronized with speech, base expression from dialogue and affect module, and several specialty expressive sequences. The functional elements of the expression include several base expressions, several eye gaze directions, several eyebrow positions for emphasis gestures, and several mouth shapes (visemes) for phoneme animation. These elements are independent (orthogonal), i.e., phoneme animation, gaze shifting and eyebrow raising work regardless of the base expression, which include Sad (mild), Concerned, Neutral (positive), Happy (with at least 4 gradations from contentment to joy), Surprise (with different presentation for positive and negative surprise), etc. There are "in-between" states ("tweens") in all these elements, for smoothing animated transitions from state to state.

Eye gaze direction may provide, for example, 16 different positions of direct gaze from right to left. Additionally provided may be two positions upward-left and upward-right, and two positions downward-left and downward-right. Reflection-indicators on the eyes may be omitted, set depending on directionality of room illumination, or kept stable. At least three eyebrow positions may be provided neutral, raised medium, raised high, plus tweens. Eyebrows participate in forming base expressions as well.

Phoneme animation utilizes a subset of 13 visemes "viseme" is set of animation frame frames of a mouth in positions corresponding to speech synthesis phonemes, according to the timing and pace of human mouth motions used to form such phonemes; an "earcon" is the audible equivalent of an icon, i.e., a short, meaningful sound that conveys an idea, Object, or action without the use of spoken language), tweened for target speech rate of 5 phonemes per second. Expressions that indicate a tongue may be eliminated to reduce this subset. A set of closed, A, B, F, F, K, O, OO, R, TH comprises a basic set of phonemes. A larger set may include any or all of Silence; P, B, M; W, UW; R; F, V; TH, DH; L; S, Z, D, T, N; SH, CH, JH, ZH; Y, IY, IH, IX, AW, H, K, G, NG; EY, EH, UH; AE, AX, AH, AA, AO, ER, AY; OY and OW.

Specialty expressions may include Wink, Blink, Curious, Inquisitive (e.g., one flat eyebrow with sideways glance), Dilated pupils, Laughing, Crying, Sleepy (used when the robot battery level becomes low), Thinking (used while downloading something, might include brow furrowing). The expressions depicted in FIG. 10A may be utilized in conjunction with the various head orientations, if desired.

Figure 10B:
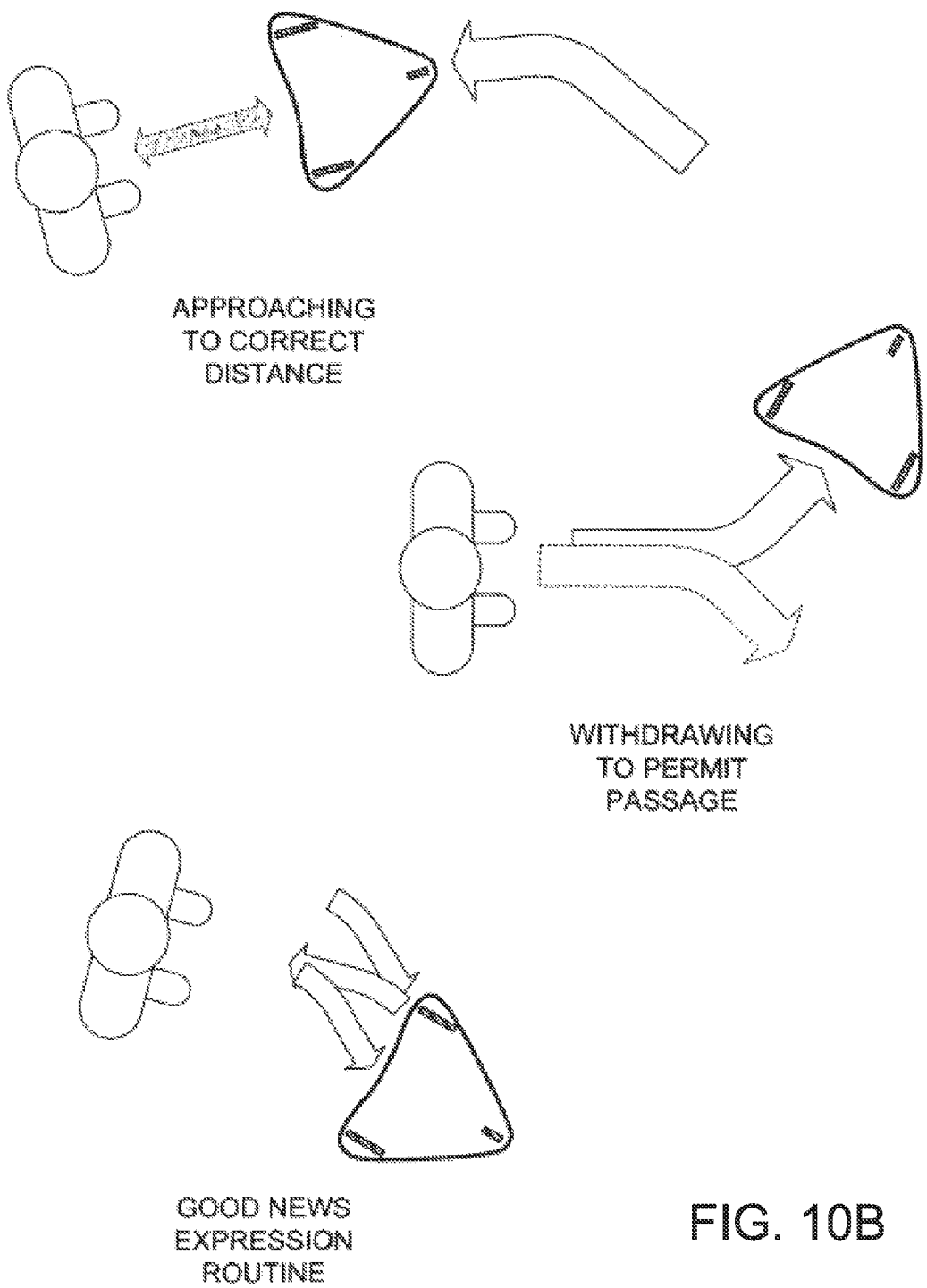
FIG. 10B depicts affect movements for a robot in accordance with one embodiment of the present disclosure.

FIG. 10B depicts expression motion actions and positions for the robot 10. The potential default position of the head 16 (shown in FIG. 1A, but not shown in FIG. 10B) may be regarding the resident.

As generally depicted herein, the form of the head and torso of the robot may be designed to provide shrugging, nodding, head shaking, looking away (change of subject) and other gestural cues; the mobility system permits approach and recede motions (personal space and conversational attention cues). It is important to note that it is not necessary that the robot have a head, or indeed any human or animal attributes. For those known gestural cues that involve motion of a person's head, shoulders, or the like, an analogous motion using portions of the robot that are in similar positions, and/or of profile, and/or are exaggerated using the entire body of the robot, if arranged according to the same or similar conversational timing and cues as human gestural cues. Some of these are shown in FIG. 10B. The approach and recede motions may also include looking away and other gestural cues. In general, as discussed herein, motion to provide a gestural cue is included in the term expression motion, and can be triggered by script, asynchronously, or periodically. As shown in FIG. 109, the robot may approach to the correct distance for a particular culture or person (which may be recorded and adapted over time as, e.g., the robot is able to detect that conversations with the resident continually involve the resident edging away from the robot). This is an example of a gestural cue, another typical gestural cue would be slightly turning the entire robot or robot's head away from the resident momentarily at a change in subject in the conversation. As also shown in FIG. 10B, the robot may perform "politely and graciously," moving out of the way of the resident if it becomes apparent the resident is beginning to move in a certain direction the robot's recording of the position of doors and/or traffic paths and/or household obstacles would facilitate keeping out of the way. This is an example of the robot simulating social interaction via robot expression motion. As also shown in FIG. 109, the robot may perform "animotions", i.e., entire-robot (via the wheels) movement scripts designed to convey expression (these may also include movement of other parts of the robot and/or sound, etc.). Each of these kinds of expression motion is considered part of the expression motion and/or asynchronous robot motions and asynchronous events discussed herein.

Figure 11A:
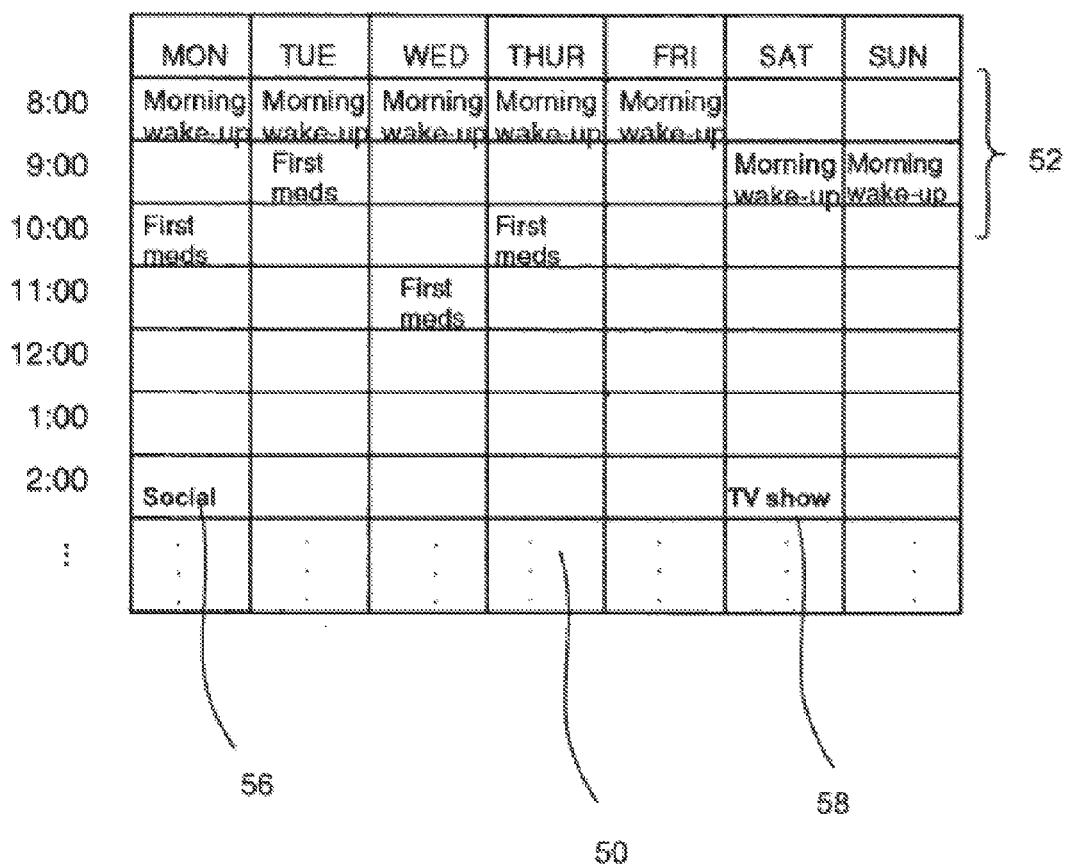
FIG. 11A depicts a schedule graphic in accordance with one embodiment of the present disclosure.

In accordance with an embodiment of the present disclosure, a mobile robot may provide interaction with a resident to promote or insure compliance with various tasks or activities. For example, the mobile robot may provide reminders and other stimuli for numerous scheduled events, as illustrated in FIG. 11A. This would be particularly useful for interacting with an elderly or other resident who may have difficulty remembering to take medications at the appropriate times during the day. In addition to supporting medication regimens, the robot may support dietary regimens, may provide recurring recommendations for managing a chronic medical condition (stretching, drinking water, resting, etc.), and instructions for restorative therapy (therapist-recommended exercises, etc.). A schedule 50 stored in the robot's processor may be set by the resident or a remote operator or caregiver. For example, the resident may enter events as desired, either via a computer or personal digital assistant, or directly by utilizing the robot's interface abilities. Additionally, the resident may request that certain behaviors be performed immediately. Similarly, a robot schedule 50 also may be linked to a doctor's computer or personal digital assistant to record critical appointments, medicinal doses, etc. Additionally, or alternatively, the schedule 50 may receive instructions from a pharmacist's office when a new medicine is prescribed, for example.

As shown in the schedule 50 in FIG. 11A, a medication compliance routine 54 may be scheduled following a morning regimen 52, which may include the robot waking the resident, a pill-loading sequence, a stretching regimen, a vital signs check, etc. The morning behavior may also be used to remind the resident of any of the activities that are scheduled for later that day, or even for particular appointments for future dates. By increasing the resident's cognitive and physical involvement in daily activities (such as planning one's own daily schedule and/or loading medication), the robot increases the resident's involvement in, responsibility for, and control of their own regimens. Such involvement in one's own care may be beneficial.

Additional regimens may be supported by the mobile robot, with similar reminder schemes. For example, the robot may provide the resident with reminders for social visits 56, or entertainment events 58 previously placed in its schedule 50. During the medication compliance routine 54, the robot may remind the resident of the purpose of the interaction, note the amount of medicine that must be taken, and request permission to proceed with the compliance routine. In the present example, the mobile robot may, depending on whether the robot includes a medicine dispenser, magazine, or carrier, (i) direct the resident to go to the room in which medication is kept, (ii) offer medication from an cup or cups borne by the robot, along with water, and/or (iii) open an appropriate portion of a pill dispenser, in order for the resident to retrieve and take the medication. Accordingly, by simply reminding the resident that the time for regimen compliance has come, the probability of regimen compliance is increased. However, various actions can be taken by the robot to further increase this probability. For example, the robot may be provided with an associated medication cache, carrier, magazine, or dispenser, and may also include with a water carrier or dispenser. When the compliance routine 54 is initiated by a time or other event trigger (for example, after a meal, upon direction from a remote caregiver, etc.), the robot may take the medication to the resident or bring the resident to the medication.

FIG. 11B illustrates an exemplary regimen initiation routine, I, the mobile robot may follow for beginning regimen routines. At step SI1, the mobile robot checks the current time (or notes the occurrence of the event), and compares it to schedule 50 (FIG. 6A). If at step SI2 the robot determines that it is time for a medication routine or other regimen routine to begin, the robot proceeds to find the resident at step SI3 (otherwise, the control process may loop back to step SI1). Finding routines are described below. At step SI4, the mobile robot may query the resident, and then determine, at step SI5, whether permission has been granted for an interaction, if so, then the mobile robot performs the interaction behavior at step SI6; otherwise, at step SI7, the robot checks the permissions that have been granted to determine whether the robot may contact the remote caregiver regarding refusal. Alternatively, if the regimen is non-critical (e.g., a social or entertainment event), the robot may move to step SI10 and leave the area. If at step SI8 the mobile robot determines that it is permissible to inform the caregiver of the resident's refusal to interact with the robot, it then proceeds at step SI9 to transmit notice to the caregiver. Otherwise, if permission was not granted, and assuming that no override condition exists, the robot may leave the area at step SI10.

Figure 11C:
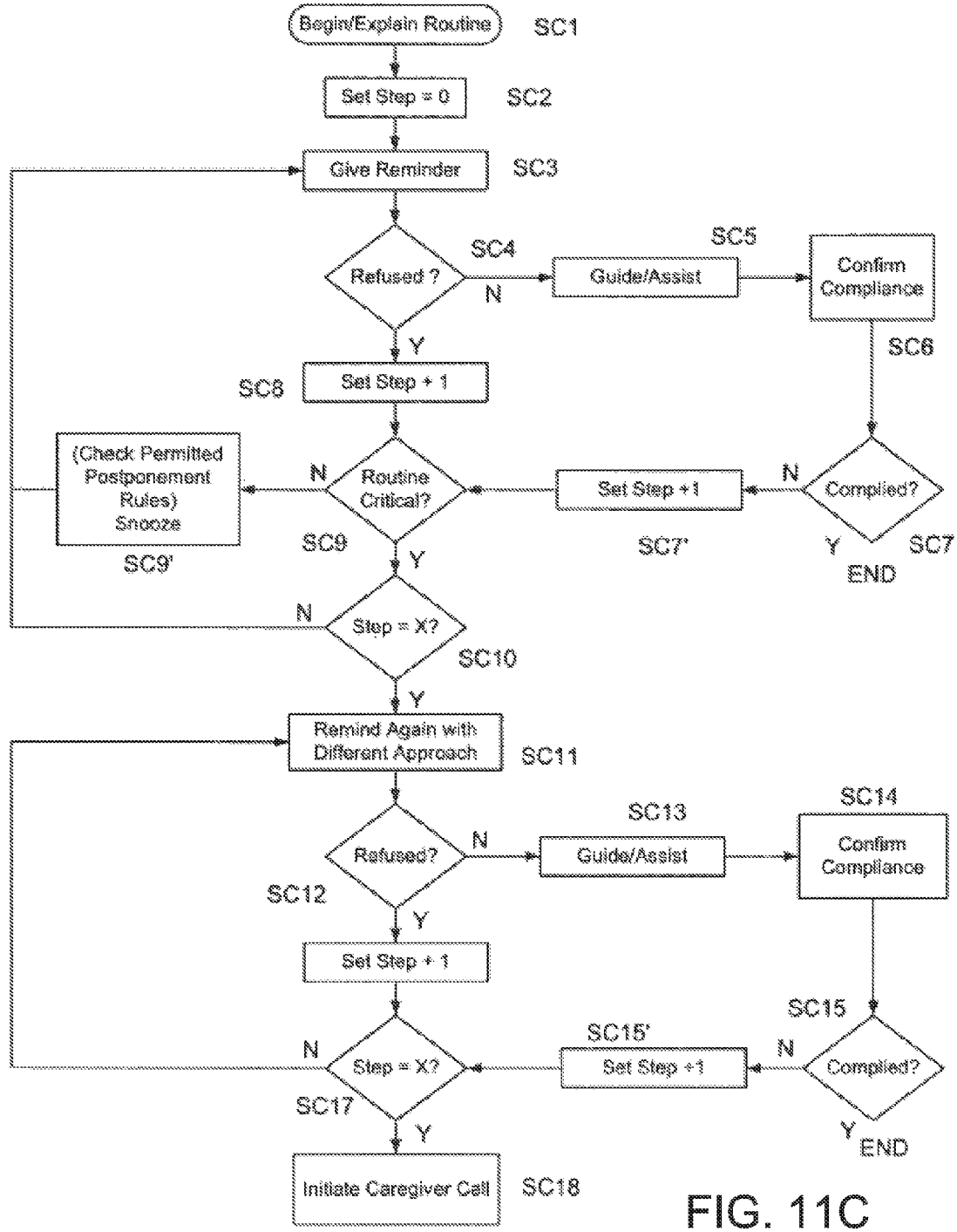
FIG. 11C depicts a regimen compliance algorithm iii accordance with one embodiment of the present disclosure.

An exemplary regimen compliance routine, C, is depicted in FIG. 11C. The robot's display screen(s) or speakers may provide displayable or audible instructions or description of how a medication should be taken or other regimen performed. When the schedule 50 indicates a regimen compliance routine (e.g., a morning routine 52, a medication compliance routine 54, a social visit 56, an entertainment event 58) is scheduled, the robot may then help the resident understand how and why the regimen is to be followed, as depicted in SC1. For example, the robot may explain the personal medication dosage information, which may include the medication that the person is to take, and the schedule they are to take it on, whether that is based upon time, events, or other factors The robot then sets an compliance counter to Step=0, at SC2, to track compliance during the routine, then gives the first reminder to follow the regimen, at SC3. If the reminder is not initially refused, SC4, the robot assists as required, SC5, by providing pills, guiding the person to a location where the pills are stored, displaying and/or verbalizing exercise instructions, preparing a videoconference connection, etc % After a set time or event, the robot confirms compliance, SC6, either with a question or other compliance-confirming action (e.g., checking contents of pill dispenser), and, if compliance is confirmed, SC7, the routine terminates, and the robot returns to monitoring the schedule 50 (FIG. 11A). If compliance has not been confirmed, the robot increases the compliance counter by 1, SC7', then determines if the routine is critical, SC9. This step SC9 is also reached if compliance with the routine is initially refused at SC4, after an increase of the compliance counter by S+1 at step SC8.

To increase probability of compliance, the robot may include a "snooze" function, SC9', that permits the resident to temporarily delay the medication or regimen when the regimen is non-critical. The snooze routine may be limited in recurrences for particular regimens deemed more important, but not critical, by the resident, caregiver, or robot (e.g., medication compliance, therapeutic compliance, etc.). For less critical regimens (e.g., social and entertainment events, morning wake-ups on days with no events scheduled, etc.) the snooze routine may time out entirely. The snooze routine may also be modifiable with a secondary reminder e.g., when permitting a delay for example, 15 minutes, the robot may issue a reminder that the compliance with the regimen will be soon required), and then return to SC3. The snooze function SC9' may also be utilized when circumstances for compliance are unfavorable (e.g., the person is preparing a meal when a teleconference is scheduled, etc.). When a regimen compliance routine is interrupted or delayed by necessity and by the resident's control, it may be reinstated after a requested delay. Such delays may be managed by postponement rules that provide guidelines as to how many times and how long medication may be delayed or refused, and whether and how a caregiver is to be notified upon a delay or refusal.

If the routine is critical, the robot determines if the compliance counter has met a predetermined threshold, SC10, if not, the robot repeats the initial reminder at SC3. In the event the threshold is exceeded (resulting from persistent refusal by the resident), the robot is provided with more assertive reminders, SC11, allowing the robot to utilize other speech ("Bob, it is very important that you take this medicine"), or affect responses (Angry, Sad) to convince the resident to comply with the regimen. If the increased assertiveness reminder is not refused, SC12, the robot moves through the assistance subroutine, including steps SC13, SC14, SC15, and SC15' (similar to the assistance subroutine beginning with step SC5 above as needed. Continued refusal SC12 increases the compliance counter, SC16, until a second threshold is reached, at step SC17. As an additional compliance step, the robot may report continued refusal to the caregiver, with or without the resident's permission, depending on the application, SC18. Again, regimens deemed critical may be reported to the caregiver without resident permission, less critical regimens may require the resident's permission, or may go entirely unreported. Additionally, at the caregiver's or resident's discretion, the report to the caregiver may provide an opportunity to exercise caregiver intervention, e.g., including a videoconferencing call, where the caregiver may encourage the resident to follow the regimen. Alternatively, for caregivers without access to a videoconference system, the display of the robot may act as an avatar for the caregiver, wherein speech received from the caregiver is converted into viseme (and, optionally, phoneme) sequences on the display of the robot, to communicate with the resident and convince compliance.

The robot is also able to take other action in the event it is deliberately or inadvertently ignored, so that probability of compliance may be increased. Reasons for non-compliance can include simple or condition-dependent forgetfulness about what actions to take, or how those actions should be taken. Moreover, unavailability of medication at the designated time, other time or scheduling problems, the resident's inability to comply because of a medical condition, lack of understanding of the necessity of following the complete compliance regimen, and dislike of side effects or other disincentives may impact compliance. The robot may provide an option to call the caregiver to provide assistance when a compliance regimen is not followed or if other problems exist or arise at any point during the sequence. The caregiver may also remotely interrupt or conclude the performance of any interaction.

The camera and microphone on the mobile robot also allows the robot to operate as a video/teleconference station.

Figure 12:
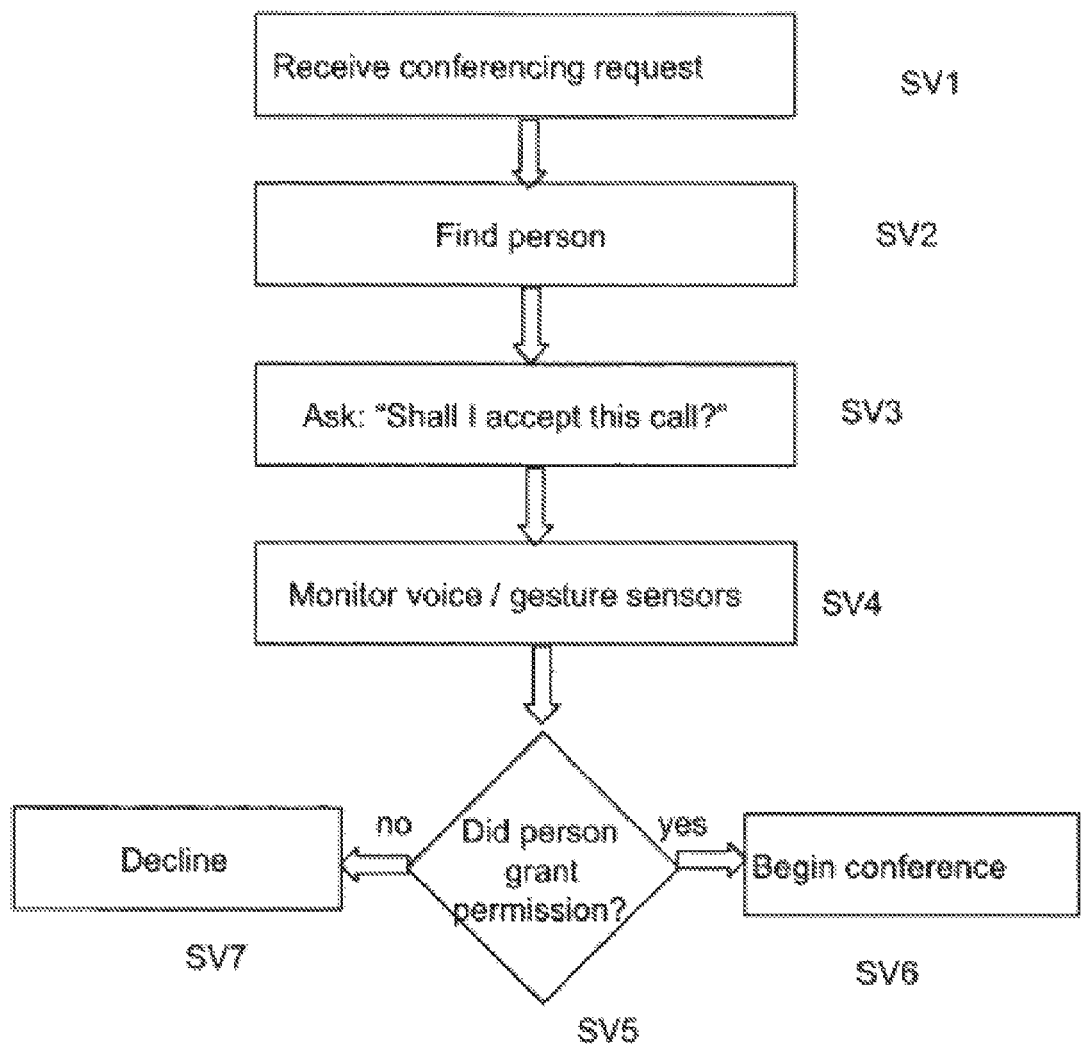
FIG. 12 depicts a video/teleconference request algorithm in accordance with one embodiment of the present disclosure.

As a videoconference station, the display may function as an avatar for the other party (as described above with regard to the caregiver avatar), or the robot may include a video coprocessor capable of processing high-compression video such as MPEG-4, H.264 AVC, or other video and sound files. FIG. 12 depicts a general conference request routine, V, that may be utilized in one embodiment of the present disclosure. For an outgoing conference, i.e., one initiated by the resident, permissions to provide outgoing video may be provided at the call initiation sequence. For incoming calls, however, permissions may be desirable to ensure that a caller may not view the resident unless the resident so desires.

The mobile robot may receive a conferencing request at step SV1 (for example, over a computer network using a wireless networking protocol, such as any standard IEEE 801.11 or 80115, or BlueTooth, UWB or other impulse radio). The robot would then proceed to find or locate the resident at step SV2. Navigation sequences for resident searching and/or locating are described in more detail below. When the mobile robot finds the resident, it may issue an audible and/or visible query at step SV3, for example, "Shall I accept this conferencing request?". At step SV4, the mobile robot may monitor the microphone, camera 28, and/or other sensors for verbal, gestural, or other responses from the resident. Additionally, the resident may touch an "Accept" button on one of the robot's screens, press a button on the surface of the robot, or touch a particular sensor. At step SV5, the robot determines from any one or more of the above events whether compliance was granted to begin the conferencing session. If permission was granted, the mobile robot may begin the conferencing session at step SV6; otherwise, the mobile robot may proceed to decline the session (and possibly, send notice of the decline to the remote conferencing requester) at step SV7.

Figure 13A:
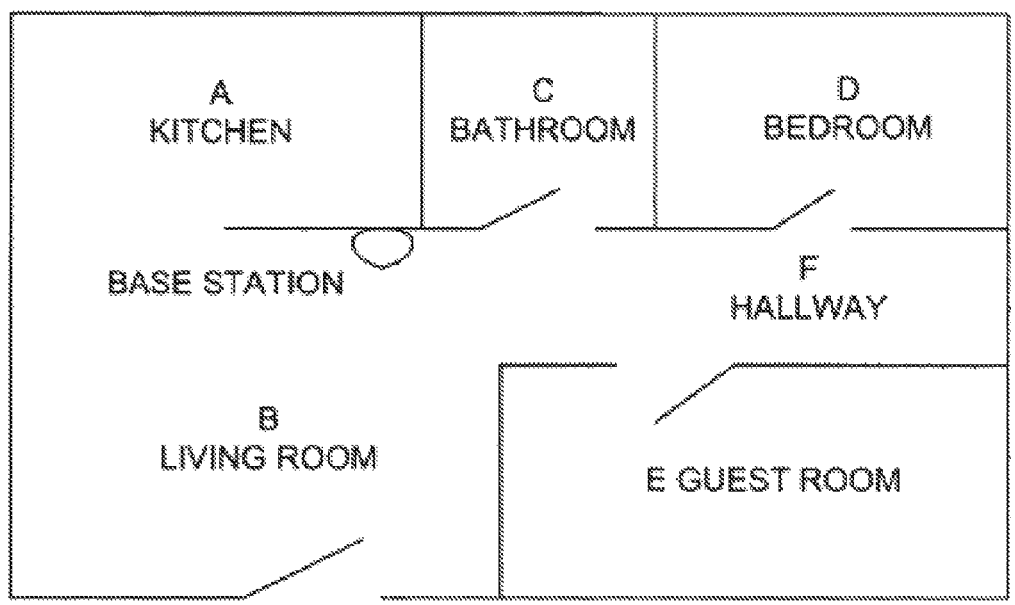
FIG. 13A depicts a plan view of a home environment in which a robot of the present disclosure operates.
Figure 13B:
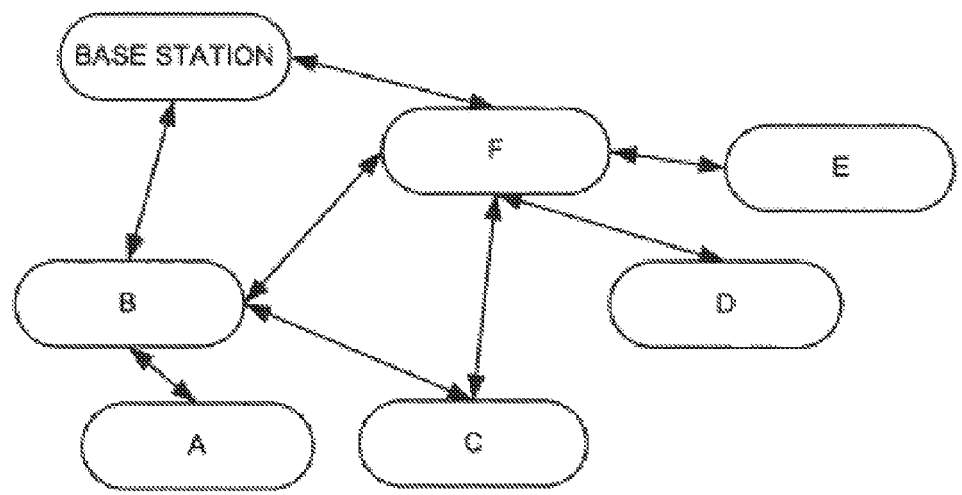
FIG. 13B depicts a robot-constructed topological map of the home environment of FIG. 13A.

To function as a useful companion to a resident, a robot may be able to navigate within an unpredictable home environment. FIG. 13A depicts a typical home layout or floorplan, but the robot would not necessarily require a spatial or blueprint "map" In an embodiment, the robot and caregiver or resident, via a web-browser or the robot's own screen, creates an icon set (map) including only conceptual icons representative of accessible rooms of interest in the home.

In constructing a topological map of the environment, the robot may move about the home and note rooms or other subdivisions of the environment. These subdivisions may be any logical division of a space, e.g., a hallway, quadrants or other portions of a large space, etc. The robot may identify the spaces at boundaries of rooms via "lighthouses," or by visual identification of features (windows, etc.). Such space boundary identifiers are described in U.S. Provisional Patent Application Ser. No. 60/741,442, the disclosure of which is hereby incorporated by reference herein in its entirety. Additionally, the robot may recognize fiducials in the room, such as indicia projected onto the ceiling, self-similar tags, etc. Examples of fiducials that are projected onto a ceiling are described in U.S. patent application Ser. No. 11/176,048, the disclosure of which is hereby incorporated by reference herein in its entirety. The robot may also utilize position information, such as provided by odometry, optical or RF time of flight or angle of arrival triangulation or trilateratizing, or may use spatial estimates, e.g., room-size detection, size of largest diagonal, etc., to identify rooms. As the robot explores the various rooms/spaces within an environment, it may build a topological map to capture room adjacency information and maintain this information during normal operation. This map information is cached in the user/resident interface, or may be stored at an online site. The robot may also identify persons and things (a charging station, doors, windows, keys, pets, etc.), optionally by recognizing a radio frequency (RF) tag carried on, present on, or worn by the person or thing. Additionally, the robot could identify a person by a signature heat, voice, and/or visual recognition pattern, as described herein.

Once the robot completes, or as the robot completes, all or a portion of the topology (and resident/entity information), it may keep this information local or send this information to a web server, as previously discussed, (or serves the content itself). Discussed herein are methods for building an interface, an icon map, and meaningful connections between the map and the home, as well as methods for robot navigation using the combination of icons and room identity information. A web client may render an icon map of the home, which may in some embodiments appear as a collection of rooms arranged by distance on the topological map, not real-world distance. The web client may also draw and label figures or other markers for the resident or other entities within the house. Thus, the location of any identified person or thing within the house may be tracked. Such technology allows the resident or caregiver to monitor the location of objects, persons, or the like within the home, if these objects or persons are detectable to the robot (via tags or sufficient recognition resources). The resident or other user may rename or classify rooms: "this is a bathroom," "this is my bedroom," etc.

The location and identity of each of these rooms and entities may be stored within the robot memory or local or remote database, and presented to the resident upon request, for example, on a robot display or a remote caregiver station or web client. The robot may display a basic list of rooms and identified persons, things, etc., but preferably arranges the icon map as discussed herein. If desired, the resident may touch any room indicated on the screen to direct the robot to go to that room. As discussed herein, a privacy mode may require that the cameras of the robot are inaccessible to a remote caregiver when the robot is autonomously navigating from room to room, and require one-time or trust-level permission attic resident to be activated once the robot arrives in a room of interest. Once in an identified room (if permissions are appropriate), the robot may take a video or still image of the space, and either return to the resident to display this data, or send it remotely to the resident's computer, networked television, or personal digital assistant. The robot may also be used as a find tool, for keys or remote controls or the like. If equipped with suitable object recognition capability (e.g., scale invariant feature transform based object recognition and appropriate learning and database routines), the robot may maintain a list of people or things that it is currently tracking within the environment (e.g., according to where they were observed last). By selecting one of those items, the resident may direct the robot to proceed to the location where the particular person or thing is located.

FIGS. 21A, 21B and 22A-22C show a method for handling navigation commands for remotely controlling a robot. Pursuant to this method, a local user (such as the resident, a caregiver working the robot in the residents home, or a setup technician) may construct a simple icon-map of the users home to be used for room-to-room navigation. Although several steps discussed herein discuss topological adjacency and/or exploring the household, the basic method does not require topological data, or exploration to build or understand topological adjacency. That is, if the robot can identify the room identity of the present room and be directed to move to a room of another identifiable room identity, the robot does not strictly need a topological map, but may explore using the most direct room-to-room navigation it is capable of in order to find the room it is seeking. Although a user may identify topological adjacency of known rooms, it is preferable that either the robot build any adjacency matrix or that none be necessary.

As shown in FIG. 21A, at step TM2, the robot explores the household. This step is non-sequential and can be carried out later in the process. In this context, the robot may simply travel randomly or upon a directed path from room to room, but a preferred mode is for the robot to be guided from room to room, following the resident or caregiver into those areas that the robot is to work in. At the same time, the robot may be told preferable places to sit and wait, what kind of room each room is, etc. However, because the method may also be carried out remotely, this exploration may include tele-operating or web-driving (as disclosed in U.S. Pat. Nos. 6,535,793 and 6,845,297) the robot among all accessible rooms. The robot may then have a count of accessible rooms (which may be corrected by a person, or an excessive number consolidated into fewer rooms, or the like). In the present examples, hallways are not considered rooms from the operator's perspective and are not assigned an icon (primarily because a robot parked in a hallway is an obstacle). However, hallways may also be treated as rooms.

At step TM4, the robot captures topological adjacency of different rooms, and docks and chargers. Docks may charge and/or provide a data connection (e.g., such as a robot base station); chargers are intended to recharge the robot but may also have data access. "Capture" in this sense may include taking the entry of data from a person or floorplan analysis, but generally means closing (topological) paths and loops according to odometry or localization data, by routine or with the assistance of a person. At step TM6, nodes are assigned by the robot. Simplicity means fewer nodes, e.g., one per room. However, bases and chargers may also have a node each, and hallways typically have a node whether or not they appear on an icon map. In addition, as shown in step TM6, doorways and interesting positions (e.g., facing to the TV, behind the chair, out of the way by the window) may also be assigned nodes. At step TM8, the number of rooms (e.g., the number of rooms a resident or caregiver has entered into the robot as existing in the house) are compared to the number of room identities (e.g., the number of rooms discovered by the robot or otherwise recorded by or made known to the robot). If there are too many room identities, the room identities are combined until the number of rooms equals the number of room identities.)

Once the topological map and/or number of rooms are in the robot or system, the user map or icon map can be built. The user map and topological map are distinct. The user map is built using a user interface presentation at a local or remote client (PC, dedicated, cell phone screen or on the display of the robot. A person's identification of room identities and association with markers (or icons) provides the easiest and most reliable way of unifying the robot's and person's world views. The resident or caregiver may or may not be shown the contents of the topological map, and connectivity and adjacency from the topological map may or may not be used to display the user map (or be separately displayed superimposed or together with the user map).

Figure 22A:
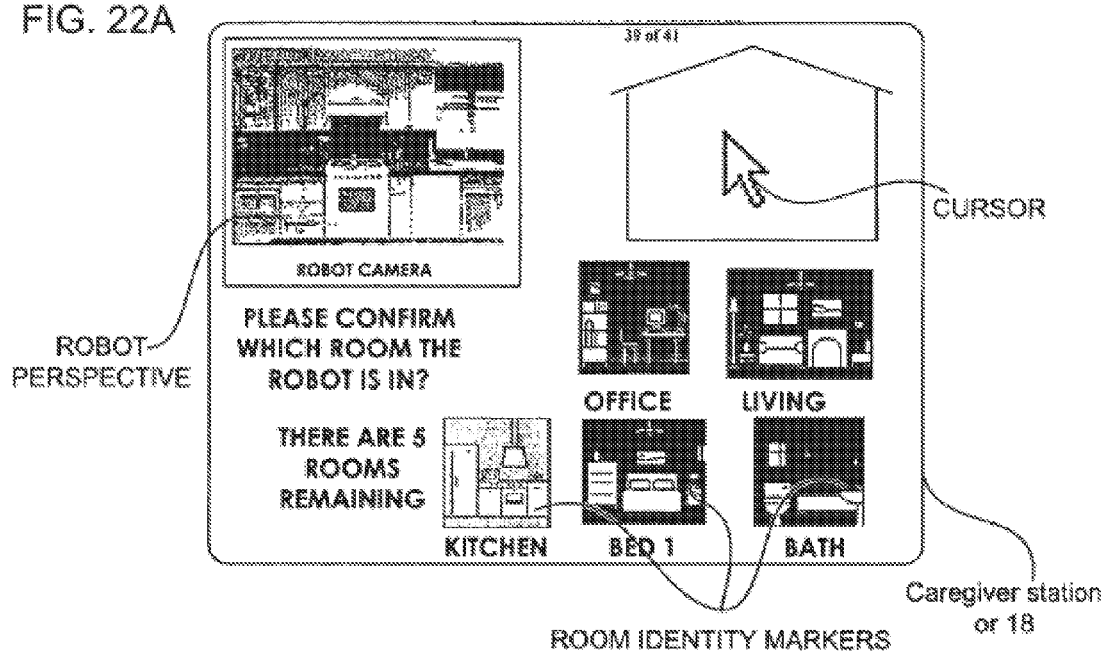
FIGS. 22A-22C depict user interface displays for the mode of navigation depicted in FIG. 19.

As shown in FIG. 21B, in order to build the user map, the robot, base station, or web application shows possible markers to the user via the interface in step UM2. As shown in FIG. 22A (depicting a user interface screen), one system employs iconography, simple pictures of each room type. In the view depicted in FIG. 22A, Office, Living Room, Kitchen, Bedroom (1 denoting that no bedrooms have yet been selected) and Bathroom icons and/or text are shown as room identity markers. Also shown is an empty graphical representation of a home (a house outline with roof). The interface in this case shows the number of rooms remaining to be identified. At step UM4 (which may come before UM2, and may not depend on nodes but on other methods of determining room identity), the robot is moved to a new node, from which the room identity is to be verified. At step UM6, the robot shows the robot's perspective to the person conducting the construction of the user map. As shown in FIG. 22A, the robot's perspective (from one or more cameras 28) may be shown to a remote user via the user interface. When this is performed locally, the user will confirm the present room that the robot is in, but there is no need to show the robot's perspective.

Figure 22B:
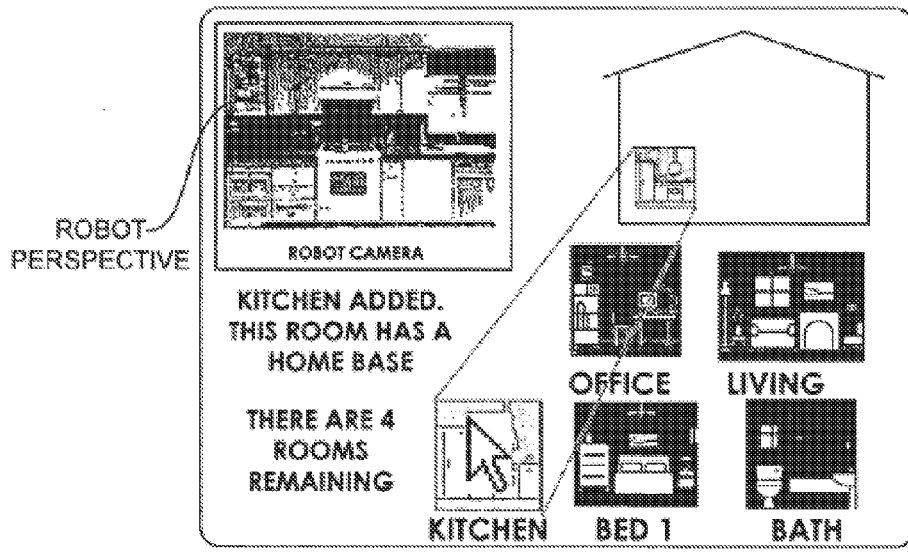

At step UM8, the robot (or web server, etc.) requests assignment of one of the room identity markers to the robot perspective or the current room ("Please confirm which room the robot is in?" from FIG. 22A). The resident or other constructing the map then selects a room identity marker. One way of receiving this information is by accepting a selection (cursor-mouse click, touchscreen) of one of the icons as shown in FIG. 22B—one room is then subtracted from the count of remaining rooms, and text confirmation of the selected room is shown. Additionally, at this time or other time, the routine may confirm which room includes a home base (charger, dock, RF access point). At step UM12, the room identity (in FIG. 22B, "kitchen" identity is correlated with the kitchen icon room identity marker). In step UM 14, the assigned room identity ("kitchen") is assigned to the icon map with the proper room identity marker.

Figure 22C:
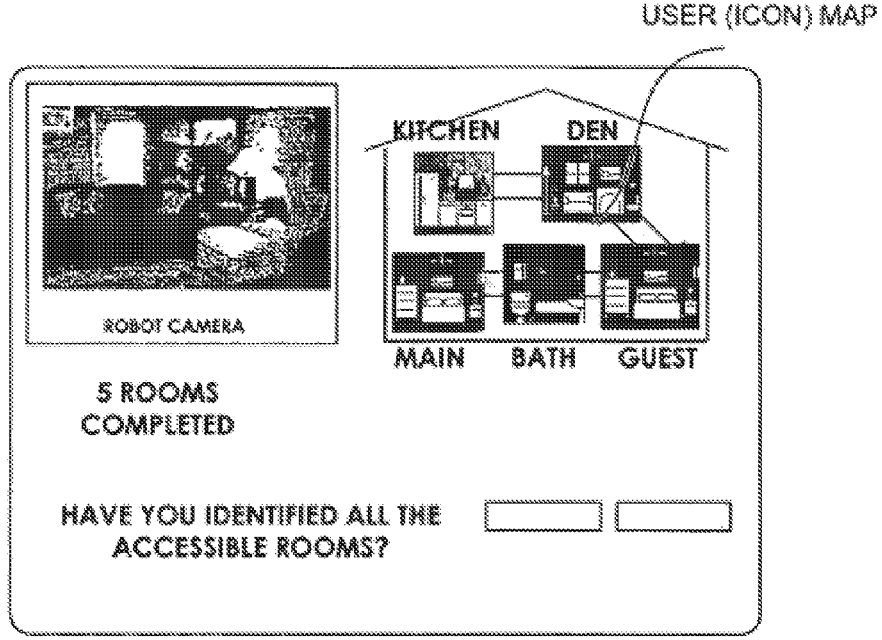
Figure 22D:
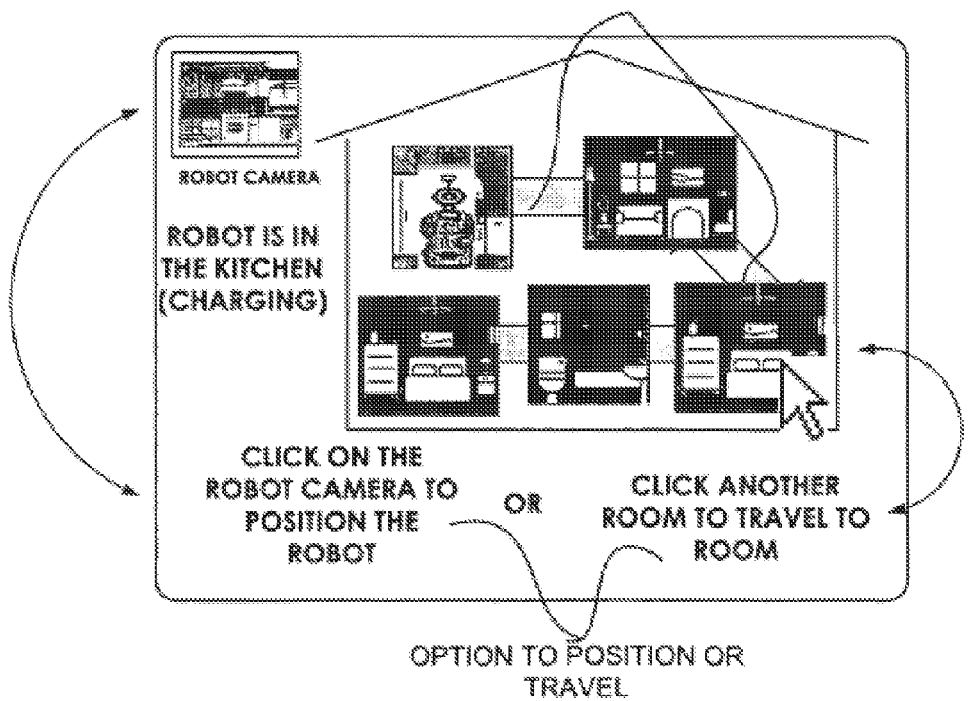
FIGS. 22D-22F depict user interface displays for the mode of navigation depicted in FIG. 20.

Step UM14 is cumulative in nature, i.e., in order to add each assigned room identity to the icon map and complete the map, steps UM2-UM12 would be conducted for each iteration of step UM 14, until step UM 16 permits the process to conclude, FIG. 22C shows the icon map built up, with all rooms to be identified (five) having been identified. Five room identity markers correspond to the five assigned room identities, and five unknown rooms have been accounted for. The completed map may be stored as an association of the graphics (markers) with the room identities (type and function of room) and further, optionally, with the rooms (including one or more topological nodes). A confirmation checks if the user has identified all of the rooms accessible. While FIGS. 22C and 22D show room adjacency as lines between room identity markers, there is no need for the user to see these (at the same time, the markers or icons are optionally arranged according to adjacency and/or with adjacency lines so as to provide the person operating the robot with an intuitive feel for travel time from room to room). As noted above, the robot may receive a selection of a room identity markers via the user interface linked to the displayed room identity markers as a first navigation command representative of a remote user's selection of a room identity marker, may recognize a present room, and may previously, at the same time, or subsequently drive among rooms of different room identity according to the first navigation command until the robot recognizes being within a room having a room identity corresponding to the selected room identity marker.

Directions via the icon map can provide multi-mode semi-autonomous navigation, with decreasing granularity. First, the user selects a room using the room identity marker, and the robot uses the room identity and/or topological information to search for a room with the room identity until it is located (if a topological map is used, planning a route rather than searching), FIG. 19 describes the first mode, using the icon map. At step IN-2, the robot receives room identity and/or navigation commands from a user (in many cases a remove caregiver, but also from the resident if the resident is confined to part of the home, as well as other exceptions). As shown in FIG. 22D, the operator may click or select an icon corresponding to a room. The exemplary interface of FIG. 22D also identifies the present location and status of the robot 10 (kitchen, charging) with text as well as a superposition on the icon map. The interface in FIG. 22D offers different options, among them to click on (or otherwise select) the local scene observed by the robot—i.e., to position the robot (via selection of ground plane position or landmark) and to click on (or otherwise select) a particular room to travel to. Confirmation steps are not shown, but may be used.

Figure 19:
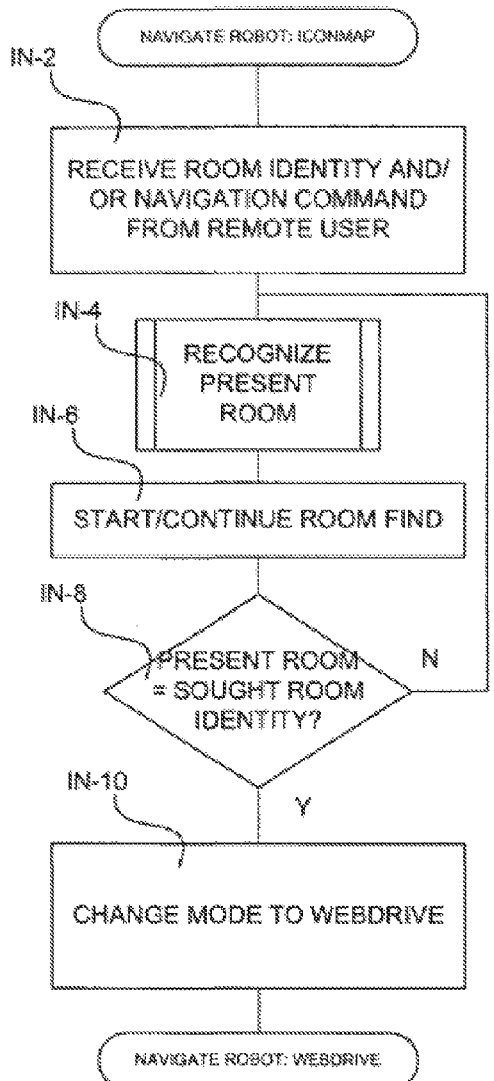
FIG. 19 depicts an algorithm of a first mode of multi-mode navigation for a robot in accordance with an embodiment of the present disclosure.

In step IN-4, the robot may recognizes the present room. A variety of techniques are available as discussed herein, including localization via RF, fiducials, odometry, dead reckoning, object, pattern, surface, or feature recognition, and the like. If the room sought is not the one the robot is in (which can be a choice prevented by the interface), then the robot will begin to search for the room at step IN-6. The robot may follow a topological map, or may wall-follow, or may use SLAM or other navigation to begin this search. The search may also be essentially random. Once in a new room, the robot may stop at a predefined node, pose or arbitrarily, in a position that permits or facilitates room recognition. However, it is necessary that the robot identify the sought room when found that a room the robot eventually finds corresponds to the sought room identity. Methods of recognizing a room are also discussed herein, and if the robot cannot confirm that it is in the correct room at step IN-8, the robot moves on to another room. FIG. 19 is simplified in that it does not specify a failure mode should the robot never locate the room sought, in most cases this would require intervention. At step IN-10, the robot will change mode to "webdrive", permitting the remote or local user to select a position on the ground in the camera view, or a landmark, for the robot to approach autonomously.

Figure 20:
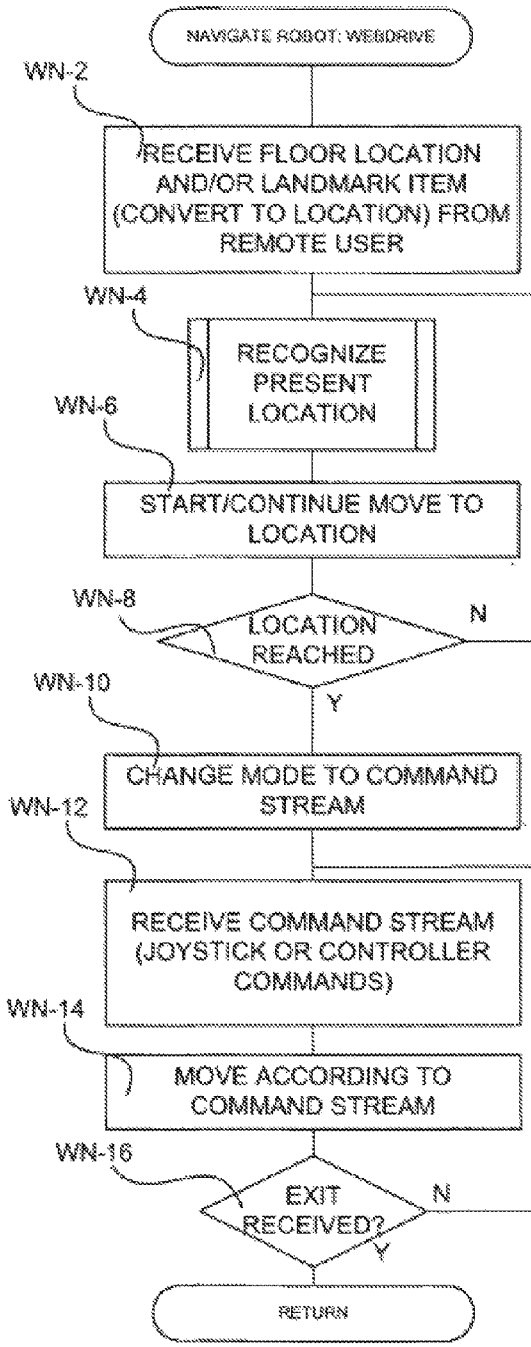
FIG. 20 depicts an algorithm of a second and a third mode of multi-mode navigation for a robot in accordance with an embodiment of the present disclosure.
Figure 22E:
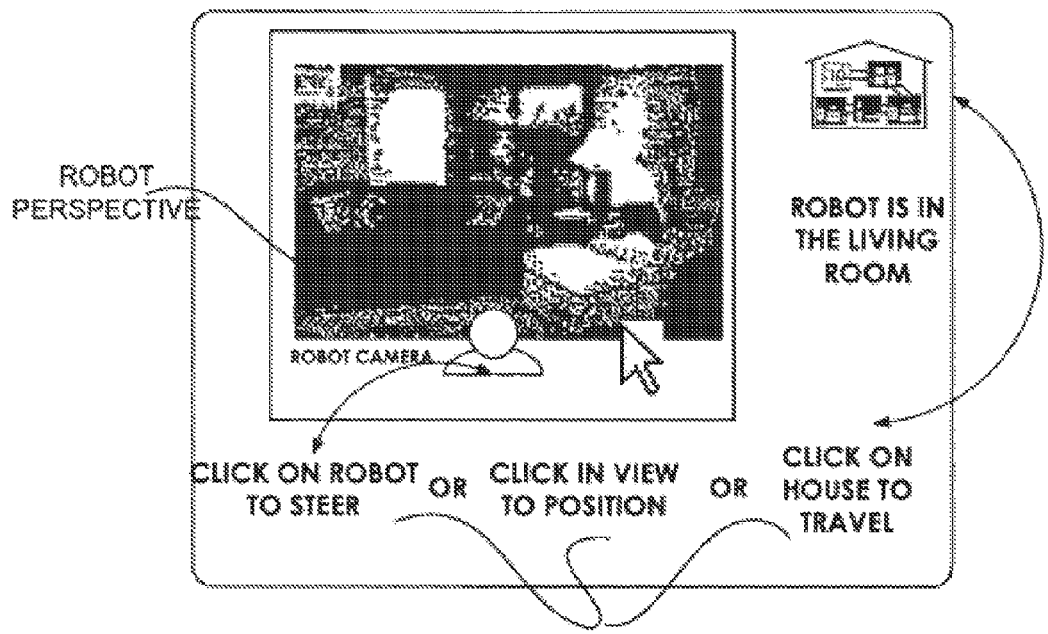

Webdrive mode has two sub-modes. As shown in FIG. 22E, a user interface may permit the operator to click a feature observed via the robots teleconferencing camera 28 or navigation camera 29 within the room. The user may indicate a desire to "steer" the robot (in FIG. 22E by clicking on or selecting an icon representing the rear of the robot's profile), i.e., use joystick command streaming to directly drive the robot, or to "position" the robot (in FIG. 22E by clicking on or selecting a point or landmark within the scene), i.e., use an interpreted x-y ground plane position in the scene as a target for the robot to move to relatively autonomously, or to "travel," (in FIG. 22E by clicking on or selecting a miniaturized representation of the icon map) i.e., to return to icon map mode and select anew room. To web drive, as shown in FIG. 20, the robot receives a floor location and/or landmark item (which may be converted to a floor location or node) from the remote use at step WN-2. At step WN-4, the robot recognizes a present location. The resolution of the present location may be rough, i.e., there may be no more than a few discrete recognizable positions in the room. Alternatively, there is no need for the robot to recognize a present position instead, it merely estimates an amount of forward movement using parallax or triangulation from the selection made within the scene by the user, and attempts to move to that position, relying upon behavioral object detection and avoidance to stop short of any hazards which may prevent completing the movement. In either case, the robot begins moving toward the location at step WN-6, and stops moving when it interprets its position to be the location desired, i.e., location reached at step WN-8.

From a new position, although FIG. 20 shows a continuous process and direct move from web drive by ground plane pointing into a command stream mode, the operator (remote or local caregiver or resident or other user) may be presented with an opportunity to step up to the icon map mode or down to the command stream mode, as depicted in FIG. 22E. Once the command stream mode is selected, an exemplary user interface could take the form shown in FIG. 22F. The command stream mode takes joystick-like (trackball, multi-degree puck controller, mouse) movement commands from the operator and directly moves the robot at a direction and heading according to the command stream. Modifications to direct movement can include behavioral oversight via intervening object detection and avoidance, slowing down for persons or objects, spline-curve or other movement prediction, estimation and smoothing, and other provisions to handle latency between command, execution, and feedback. If ping times are very high, this mode may be disabled in favor of ground plane point web-drive mode.

Figure 22F:
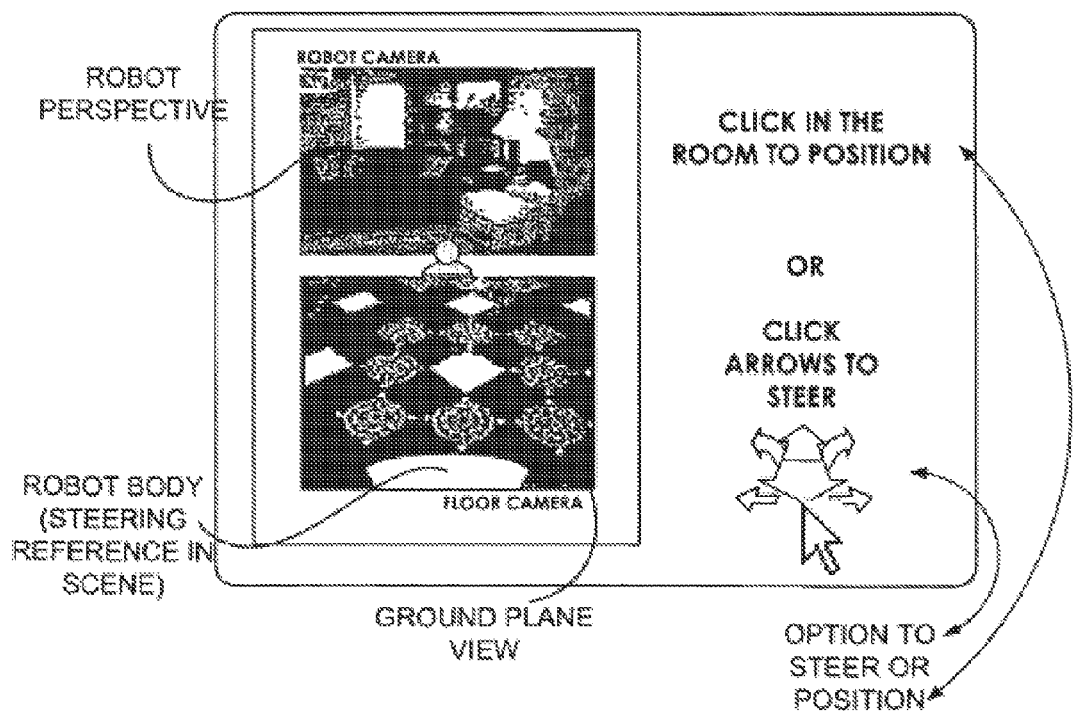

As shown in FIG. 22F, the command stream mode may use on-screen active arrow controls to simulate a joystick, and may offer a choice of steering using these arrows or positioning (by returning to the view shown in FIG. 22E. As shown in FIG. 22E, in order to steer effectively, it is often useful to have a portion of the robot's body or leading edge appear in the scene as point of reference for scale, orientation, and steering. Estimation of gaps, angles, and distances by a human operator is improved. In FIG. 22E, two different camera views are shown: a ground plane camera which is used for steering clear of Objects on the ground, and a robot perspective camera for showing the "eye-level" view from the robot's primary or teleconferencing camera(s) 28. The robot body, steering reference, ground plane view may be from a separate camera or the same camera. Upon the change to command stream mode at step WN-10, the robot receives a command stream of joystick or controller commands as discussed above in repeatedly cycling through steps WN-12 and WN-14, and the robot is substantially directly (albeit with latency) moved according to the command stream WN-14. An exit signal permits the user to return to other functions of the robot at WN-16.

This navigation ability may also be remotely available to a resident who is away from home, or who may be confined to a particular area of the home. In such a case, the resident may remotely access the robot interface, via an internet connection (or via a personal digital device), and select a room or thing on which the resident desires status information. For example, the resident may want to robot to confirm that the front door is locked, and selects the living room on the map displayed on his or her web browser. The robot first identifies its present location (for example, the bedroom D). The robot then moves from the bedroom D, through the hallway F, until it reaches the living room B, where the front door is located. The robot may then take a visual image of the front door, and send that visual data to the remote resident, at which time the resident may instruct the robot to return to its starting point, or to move to a different location. Alternatively, the resident may first select the room where it wants the robot to navigate to, then direct the robot to an item or more specific location within that room, then direct the robot to move on to a different location. The robot may also send streaming video to the resident as it moves throughout the home. Additionally, this mapping and tracking functionally may be available to a remote caregiver, with the appropriate permissions, as described herein.

Figure 14A:
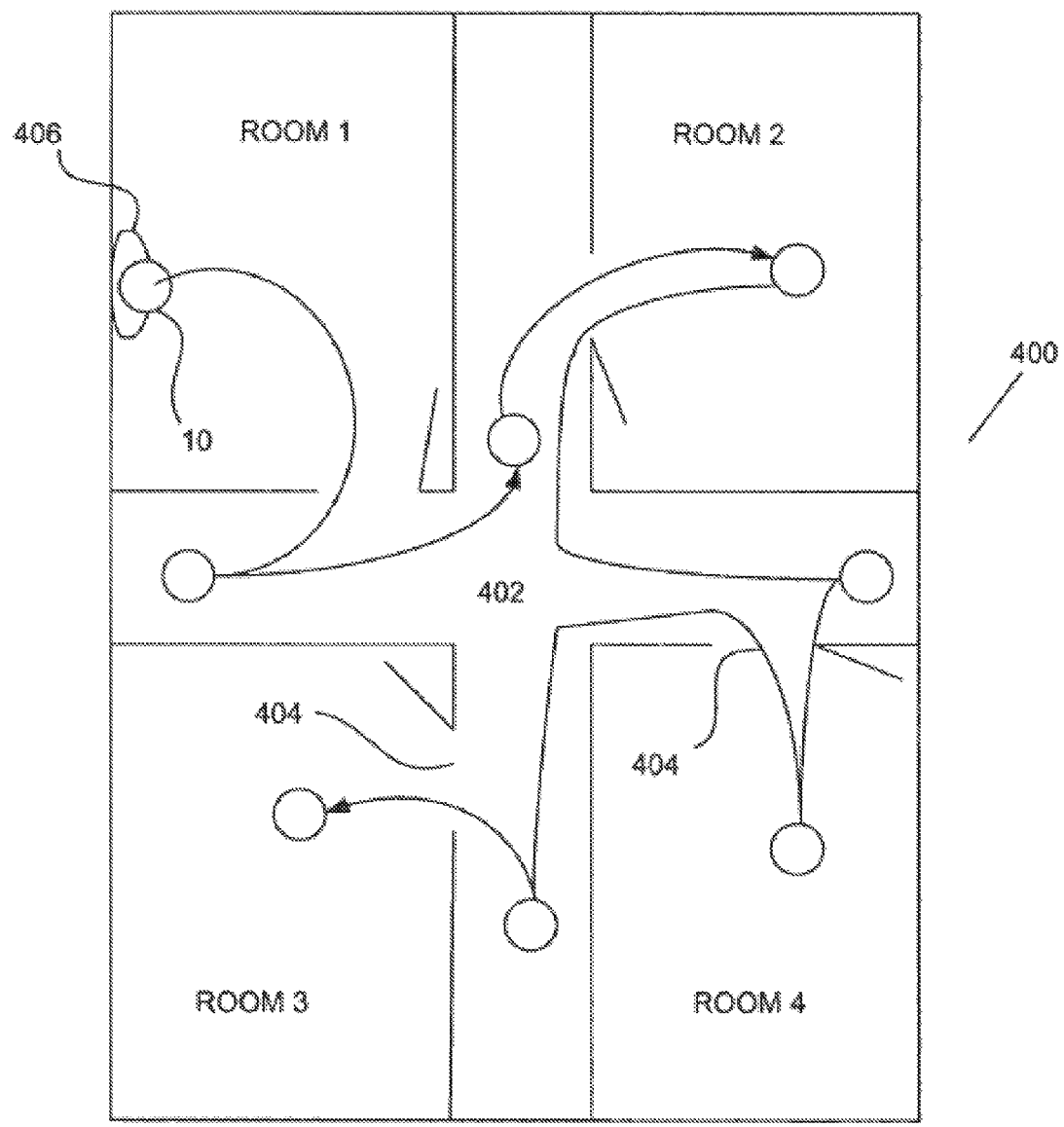
FIG. 14A depicts a plan view of a path traversed by a mobile robot during a locating behavior, in accordance with one embodiment of the present disclosure.

In the course of interacting with a human resident, the robot and resident may become separated within an environment. Should the robot require contact with the resident, due to the beginning of a compliance routine, initiating a teleconference, or otherwise interacting, the robot will be able to navigate the environment to locate the resident. A plan view of one such navigation path in an environment 400 is depicted in FIG. 14A. The environment 400 may include a number of rooms, such as rooms 1, 2, 3 and 4, as shown, as well as a corridor 402 which interconnects each of the rooms. Entry and egress to each of the rooms may be provided by doors 404, which may be open or closed. The mobile robot 10 may perform a locating behavior for seeking out the resident before beginning an interaction or other robotic behavior that requires the presence of the resident. For example, if the robot 10 is docked at a base or charging station 406 when its schedule determines that a regimen must be initiated, the robot 10 may proceed from room to room within the environment 400 while monitoring the robot's immediate environment for indications that the resident is present.

In each room, the robot 10 may employ a sensor suite that is responsive to the presence of a person (including sound detection, movement detection, pulse, breathing and/or heat detection) and/or an audible or visual query. The robot 10 also may move to a central area of the robot's known environment 400, or may move to an observation area in its present location (a central point in the room, for example), to begin its query. This first initial centralized locating function may be helpful if the robot recently had contact with the resident in the room or area in which it is still presently located but did not detect the resident leaving the room. The robot may also make a first round of known rooms, stopping in positions permitting surveying of large areas and monitor sensors for any responses. Filtering can be used to exclude false positives (the stove is too hot to be the resident, the dog is too low to be the resident, etc.).

In an alternative embodiment, the robot may utilize a paging system, with or without the use of sensors, to locate a person. This type of system may also be utilized if the robot is experiencing a sensor or other failure condition. When paging a person, the robot may use the doorways to separate rooms or chambers, in order to page the resident over only a short (in one embodiment, less than about 5 m) distance, from locations in which a direct line from robot to resident is more likely. The robot may also use this paging in subparts (smatter areas) of rooms or from passage outside of or between rooms. The robot may page from the doorways themselves in order to reach two rooms with one page.

When a person is detected, the robot may attempt to identify the person by employing an audible or visible query that asks whether the person is present, via a speaker and/or recorded speech or sounds, or synthesized speech or sounds. If the robot proceeds through every room, as depicted in FIG. 14A, without locating a sound, movement, or heat source indicative of a person, the robot may perform a second round of the circuit or other path through the rooms (starting in the present room), but on this occasion using an audible or visible query in each room. This search strategy may also be utilized if a sensor failure is preventing the robot from properly operating. Where other means indicate the presence of the person in the house (e.g., if the robot detects the presence of a resident's personal radio frequency identification (RFM) tag but no other signs are detected), or confirm the presence of the person but lack of responsiveness to queries (e.g., pulse and breathing detected but no response to queries), the robot can conduct procedures to resolve the inconsistency. These procedures may include requesting a caregiver checkup call, or the robot may place a telephone call into the environment searched to make the same queries via phone, or the robot may contact emergency services.

The mobile robot may also use a secondary system for confirming the identity of a person, such as by analyzing an infrared image or signature heat pattern corresponding to the person being sought, performing acoustic analysis to recognize the voice of the person, detecting an RFID or magnetic tag associated with the person or carried by the person, detecting a particular motion or a gesture, and/or performing image analysis on a video stream or still image frame generated by a camera to recognize facial features or memorized clothing sets typically worn by a person.

In selecting a next location to continue a search, the mobile robot may use any suitable method, including, but not limited to one or more of optical room feature recognition, sonar, RFID room tagging, infrared (IR) directional beacon detection, odometry, inertial guidance, dead reckoning, room mapping, and/or compass navigation. In one embodiment, the robot may use an available heading to a doorway or other wall gap (the heading made available by mapping, by passive detection of beacons from which the heading to a doorway can be inferred, or by active sensor detection of the doorway itself). The mobile robot may also choose an arbitrary path intended to locate a door in a reasonable time (e.g., wall following utilizing signal reflection) and then proceed until a doorway is detected as having been traversed. The robot may also identify a doorway by analyzing odometry and heading while in wall following mode. Identifying successive odometry/heading combinations may indicate that a doorway has been traversed. If the mobile robot encounters any obstacles when traveling to the next location, the mobile robot may circumnavigate the obstacle, or otherwise adjust its path of travel, in order to proceed to the coordinate location of the selected next location, or, alternatively, the mobile robot may simply halt at the obstacle and begin the query process anew. In the case of the robot adjusting its path of travel, once the robot passes an obstacle and encounters its previous heading, it may continue on until a predetermined distance is reached. In addition, the robot may simply move a threshold distance, ending in either another room, or in the same room, before beginning its query.

In addition, as illustrated in FIG. 14A, as the mobile robot encounters walls and/or doors 404 (either open or closed), it may generate a obstacle, geometric, preference, topological, grid, Voronoi, or other map of the environment 400. Instead of generating its own map, the map may be transmitted to the robot by the resident, possibly as part of a start-up, or ownership-initiation sequence. In such a case, the robot may supplement the transmitted map by identifying locations of transient elements within the environment. Furthermore, the mobile robot may have a upward-facing camera for recognizing pose and/or rooms within the environment 400 based on ceiling characteristics (e.g., ceiling edges or configurations, patterns of indicia located on or projected onto the ceiling, etc.). Such systems are disclosed in U.S. patent application Ser. No. 11/176,048, the disclosure of which is hereby incorporated by reference herein in its entirety. The mobile robot may also adjust its method of selecting the next location by selecting a next location or node that is available through a known door or node-connecting topological branch. On some occasions, potential paths could be blocked by a closed door.

When the mobile robot encounters a closed door, it may attempt to communicate with a person on the other side by applying an audible signal to the closed door. For example, the mobile robot may include a door knocker (such as a solenoid) or a speaker which can be applied to the closed door to transmit an audible signal or announcement to the closed door. Accordingly, the mobile robot can attempt to contact a person even when the person may be located in an area that is inaccessible to the robot.

Also, the mobile robot may plan a path to the selected next location based on its active or passive detections or map of the environment 400, or it may employ odometry, and/or inertial guidance when navigating. In this way, the mobile robot may identify when a door has been traversed, for example. Alternatively, the mobile robot may employ any suitable method for navigation, mapping, and room identification, such as, for example, infrared beam-detection (e.g., the navigation and beacon systems as disclosed in U.S. Provisional Patent Application Ser. No. 60/741,442, RFID room or door tagging, inductive or resonance detection of tank circuit or amorphous metal tags, optical feature detection or image analysis. The robot may also utilize Simultaneous Localization and Mapping (SLAM), using machine vision-based methods, computational resources, and sensors, to prepare vision and odometry data of an environment. Such systems are disclosed in U.S. Provisional Patent Application Ser. No. 60/822,636, the disclosure of which is hereby incorporated by reference herein in its entirety.

Figure 14B:
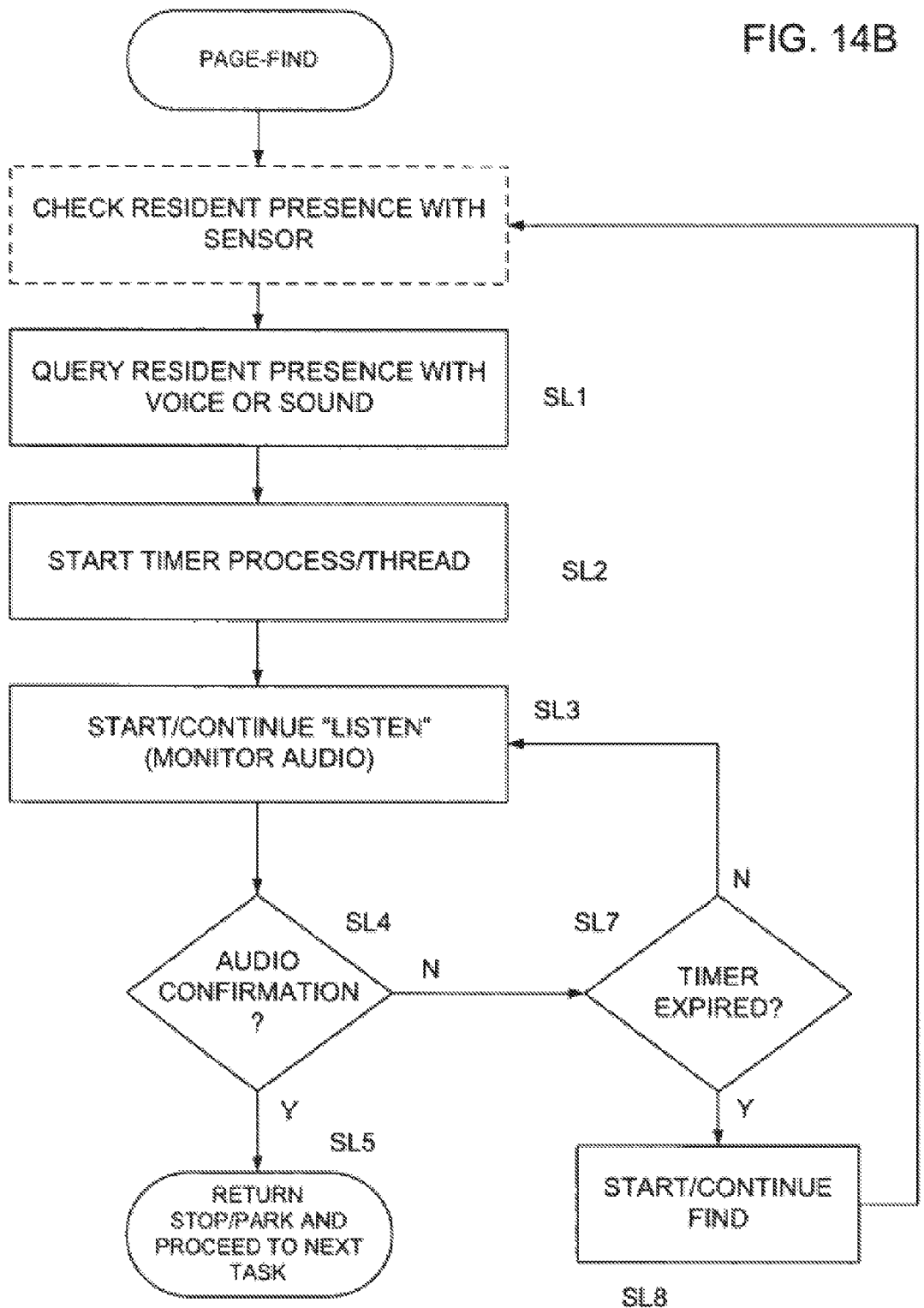
FIG. 14B depicts a locating algorithm in accordance with one embodiment of the present disclosure.

A locating routine depicted in FIG. 14B may first include checking the local area for a resident at (optional) step SL0 (e.g., by pyrolytic heat sensor; and/or sound; and/or visual recognition of movement or clothing; and/or tags or other emitters worn by the resident; and/or any one of these used to confirm or in combination with at least one other). If the resident is sensed with high confidence, the routine may proceed directly to a success routine. However, the routine may also seek to confirm its detection. Whether the locating routine checks first for a resident or proceeds directly to querying, in step SL1 confirmation or direct querying may require a simple query in a location where a person is detected or that has not yet been checked: "Are you there?," as depicted in SL1. As alternatives, the query may specify the name of the person being sought, or may be a message intended to imply a lower level of cognitive ability, e.g., a simple trill or other emotive sound, or a "Mary here?" The mobile robot may then begin a countdown of a timer at step SL2, and monitor an audio sensor SL3 (such as a microphone) for any verbal response to the query. If the mobile robot determines that a verbal response has been detected at step SL4, the mobile robot may then proceed to its next task. On the other hand, if no response is detected, or if a non-noise response does not correspond to responses in the robot's library (e.g., "Go away" from a person other than the resident), the mobile robot may check the timer at step SL7. If time has run out (as determined at step SL7), the mobile robot may then move to a next location SL8 and repeat the process. Otherwise, the mobile robot may return to step SL3 and continue to monitor the audio sensor for a response until the timer completes its cycle.

The robot's verbal annunciation need not sound like "shouting" or include blasting a claxon or other loud sound. Instead, the annunciator sound levels may be generally inoffensive to others in a room or adjacent room. As an example, normal background noise is about 35 dB, and the annunciator would sound in a normal speaking voice volume of about 55 dB to about 65 dB, or at least about 15 dB greater than detected background noise. If the resident has been identified as hard-of-hearing, the robot may increase the volume to up to about 75 dB or some other threshold level, and may add a visible signal and/or activate a resident-carried remote vibrator. The annunciator volume may be reduced to about 10 dB to about 20 dB greater than detected background noise; and/or may be pitched in frequencies that are typically still audible even to the elderly or those will various types of hearing loss within a range of about 500 Hz to about 5000 Hz).

To facilitate a more rapid response to needs of the resident, or to limit the amount of time the robot spends away from the resident (thus encouraging more bonding), the robot may be provided with a sensor suite and reactive behaviors that tend to keep the robot in the vicinity of the resident, or track the resident from room-to-room. Simply following the resident from room to room may produce annoyance on the part of the resident to the constant presence of the robot; therefore, the robot instead undertakes actions and tasks that tend to keep the robot near to the resident, but without close following. The behaviors may (i) increase the probability that the robot is near to the resident, (ii) increase the probability that the robot is in a room or near to a room where the resident has been or will be, and/or (iii) increase the probability that the time to find the resident will be shorter.

For this purpose, in one embodiment, the robot may maintain a comfort or presence score (or anxiety score if the implementation is viewed from another perspective), which may increase, increment, or fully replenish in the resident's presence and may decrement, decay, or be reduced in jumps or steps as time passes or events occur without observing the resident. Once the comfort score decays beyond a threshold value or enters a certain range or region, the robot may register the score as a discomfort, which may activate or change the priority of a resident-seeking behavior or other behavior that tends to improve the proximity of the robot to the resident. Upon direct querying, sensing the resident, or checking phenomena that tend to correlate with the presence of the resident (heat, sound, movement), the comfort score may be replenished, or be gradually incremented, depending upon the character of the detection of the resident or phenomena.

Figure 15:
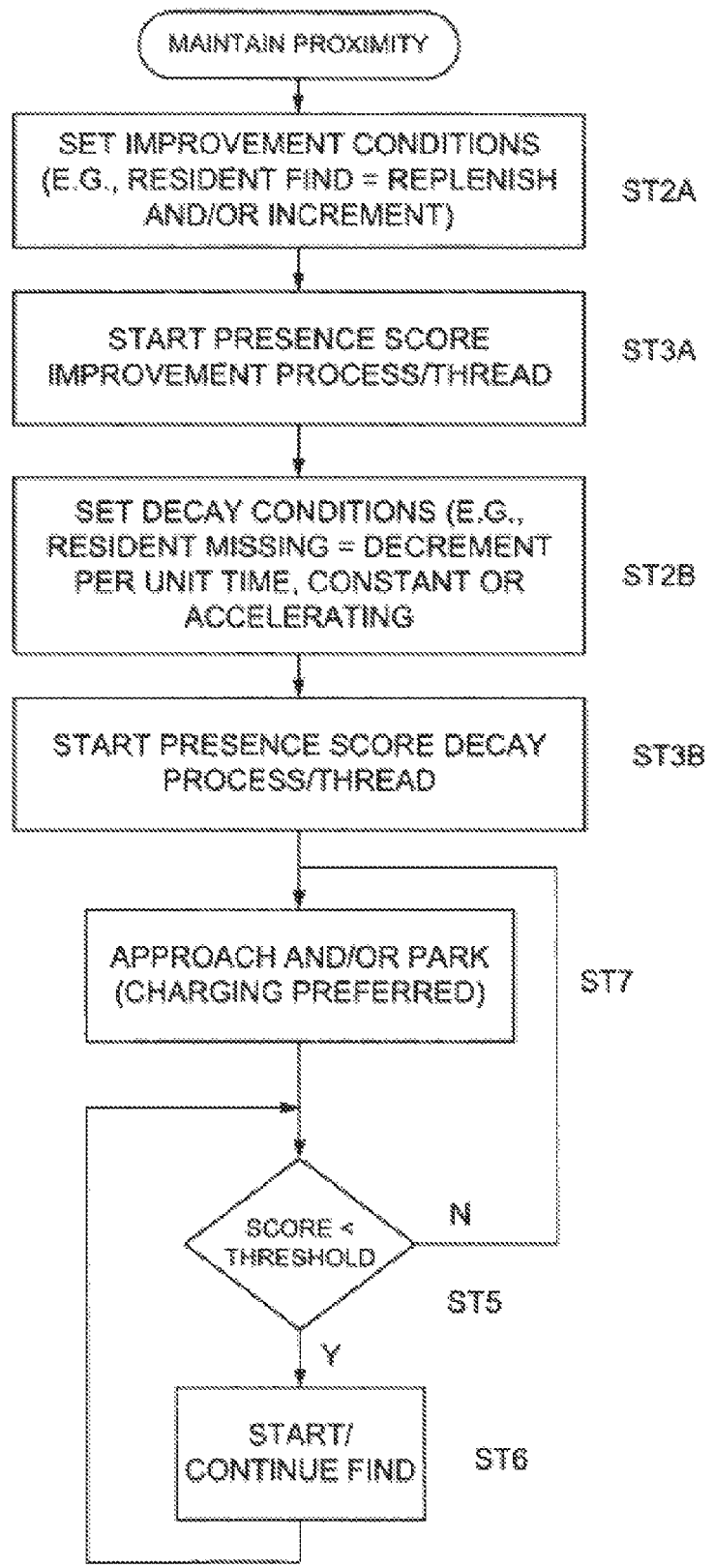
FIG. 15 depicts a proximity algorithm in accordance with one embodiment of the present disclosure.

An exemplary tracking routine that utilizes a comfort or presence score that score relates to proximity to the resident) is shown in FIG. 15. In a preferred embodiment, improving and decaying such a score are separate processes, and may occur for separate reasons, although the same score is affected. Other factors, such as battery condition or charging dock proximity, may also affect the score. Initially, at step ST2A, the improvement conditions are set, e.g., the score may be set to a maximum (fully replenished) when the resident is proximate, or may be improved or incremented by a set amount when the resident is proximate. These may be different for different times of day or for different user preferences. The presence or comfort score improvement process or thread is then started at step ST3A. At step ST2B, the decay conditions are set, e.g., the score may be set to a half (fully replenished) at the beginning of the day, or may be improved or incremented by a set amount, at a constant rate or at an accelerating rate, when the resident is not detected. These may be also different for different times of day or for different user preferences. The presence or comfort score decay process or thread is then started at step ST3B. For example, the robot may begin in a bedroom, in an idle, charging, or sleeping state, yet detecting the presence of the sleeping resident, and maintaining or reincrementing the comfort score at a maximum value. The robot may enter a parked or waiting state, or may approach the resident, monitoring its sensors ST7. If the robot is not directed to follow a person when the person leaves a room, it may stay in the room, yet the comfort or presence score will decay according to the thread controlling it. It should be noted that the robot may maintain competing scores, e.g., adding a security score that measures whether the robot is close to a charging station. So tong as the comfort score is within a threshold value, or together with other scores, the robot may not activate or change the priority of a finding behavior. This may result in the robot being parked at a charger or in the last position at which it stopped searching for the resident. Once the threshold is crossed (ST5), the robot begins to try to find the resident, leaving the room to find (ST6) and approach the resident. If there is more than one exit to the room, the robot may have recorded and recall the exit used by the resident (not shown). At some point, the robot may find the room in which the resident is present. When the resident is found, the comfort score or presence score will improve according to the ST3A thread, and step ST7 will again approach and park the robot proximate the resident.

The robot would then park itself quietly, or with a simple comment or noise, in the same room as the resident, in a position that does not block traffic paths. Corridors and very small rooms such as bathrooms may be off-limits, and the robot may instead park itself in a nearby room. At this point, the cycle begins again as soon as the comfort score reaches a maximum. If the robot does not find the resident, it may seek the security of the charging station or other comfort generating phenomena. In this manner, although the robot does not follow the resident, the distance to the resident may usually not be very far, and the robot may be often in the same room. The robot may also communicate in order to elicit a response from the resident and/or provoke interaction. Accordingly, the robot may be perceived as a more natural entity, may maintain proximity to the resident without uninvited irritating following behaviors, and enhance the likelihood of successfully interaction with the person, as well as ensuring that the resident is quickly locatable. By using the tracking behavior, the robot increases the probability that it will be near to the resident when the resident is to be found or when the robot is called by the resident. The robot need not be within detection range, only closer to the resident than it was when it started looking, although parking within a detection range may require that the robot search less often. If a charging station is nearby, the robot dock and charge. Additionally, the robot may dock and charge with a nearby charger, even if that charger lies outside of the detection range, if the robot concludes it requires additional power.

Alternatively or in addition, the robot may behave in accordance with a virtual pheromone system, in which a room is assigned the comfort score rather than one score kept by the robot. When the resident is not observed in a particular room or location, on the other hand, the comfort score of that room would decline. Entering a room of frequent use may increment the comfort score, and the robot may tend to navigate to rooms that tend to increase the comfort score. These properties may be time dependent the robot may look first in the TV room at 7 pm, first in the kitchen at noon, and first in the bedroom after bedtime; the decay rate may be correlated with times of frequent room changing (early morning activity) or stability (evening leisure activities). Thus, the robot may choose to seek out the resident in rooms with higher comfort scores before resorting to searching locations with lower comfort scores, and therefore potentially increase the likelihood and typical speed of looking for the person. Alternatively or in addition, the robot may form a comfort-related spatial occupancy map, landmark map, or topological map that updates features or cells according to the probability that the feature or cell is adjacent to or occupied by the resident in this case, each cell corresponding to a room, corridor, or a nearly room-sized area.

Alternatively or in addition, the robot may behave in accordance with a force, vector or potential field that maps a comfort scores/vectors onto a motor, drive, or navigation goal space. The comfort scores may be vectors or areas of high comfort potential, which may decay over time. The comfort potential of the resident in the potential field may be compared to with the comfort or security potential of the charger, base station, or recorded wireless signal strength field to decide the location where the robot will park itself in the room with the resident. Such fields can define that the robot should be near to, but not too near to, the resident, and also in a strong wireless signal strength area available in that room.

The mobile robot may improve its rate of successfully maintaining proximity to the resident by tracking and following the resident in certain circumstances: e.g., a fixed or variable percentage of the time the robot successfully detects that the resident has left the room, and/or during certain times of the day, and/or after certain patterns of conduct by the resident. For example, if the robot recognizes that the resident is beginning preparations to retire for the evening, the robot may follow the resident from living room to bedroom. Additionally, or in alternative, the robot may record, interpret, or accept inputs describing the resident's daily routine or schedule, and may use the schedule to predict and move to an appropriate room ahead of the resident.

The robot may initially become aware of the resident's presence by any appropriate method, such as by asking whether the resident is present and receiving an affirmative response, or by having the robot's attention directed to the resident via a command or input from the resident or a caregiver, for example. The robot may detect the presence of the resident using a physical sensor or input from a variety of sensors, such as infrared sensors, heat sensors, motion sensors, optical sensors, a microphone or other acoustic sensor, electrical property sensors (e.g., capacitance or any other suitable physical sensor. Alternatively, the resident may carry a tag such as an active or passive RE or RFID tag, tank circuit, sonic emitter, light source, any of which may carry a modulated signal, or the like, which the robot may use to identify and locate the resident. Used in conjunction with an item such as a medical alert bracelet would make such an item very useful for increasing the reaction time of the robot to various medical situations. As another example, once the robot has located the resident in order to perform a task (as described in the above-described embodiments), the robot may then continue to keep track of the location of the resident and track the resident as the resident moves about the environment.

While navigating an environment, the robot will encounter various candidate objects (objects higher than room temperature, in motion, or generating noise), which may or may not be the resident sought. In order to determine whether a candidate object has a high likelihood of being the resident, the robot may associate a particular sensor input profile with the resident, and compare any objects that come within range of the robot with the resident's sensor profile. For example, if Ann is the resident that is being cared for, then the robot may record Ann's average temperature using an IR sensor, Ann's approximate size using a camera and/or image analyzer, the clothing combinations typically worn by Ann in the same manner, pitch of Ann's voice or the sound of Ann's breathing using a microphone or acoustic sensor, etc., during the course of performing tasks with or for Ann. Based on these or other inputs, the robot may generate a sensor profile that is characteristic of Ann. Furthermore, the robot may analyze or distill the characteristic sensor profile of the resident by employing suitable statistical models or recognition models, e.g., Bayesian analysis, Hidden Markov Models, techniques dependent upon these two, or other statistical or heuristic routines for filtering and recognizing.

The robot may also track a number of grouped characteristics of an entity, maintain a persistent record of grouped characteristics labeled as a particular entity, and/or the location of that entity in space (including topological space or other abstract representative space). When the robot compares an observed object to the resident's characteristic sensor profile, it may generate a comparison score that generally correlates to the likelihood that the observed object is, in fact, the resident. If the comparison score of the observed object exceeds a threshold score, the robot may track the object in order to remain generally proximal to the resident, or may rank the comparison scores of two or more of the observed objects to determine which object is more likely to be the resident, or may track new objects instead of old objects, or may switch tracking from one object to another when the comparison yields a difference above threshold. The robot may rely on its likelihood analysis without seeking direct identity confirmation from the resident. The robot may try to maintain a particular distance or distance range from the resident, and may react only after a delay or distance threshold is crossed.

Within an environment, one or more docks or base stations (such as a recharging dock or resupply dock) may be positioned for the robot to recharge its batteries or obtain supplies. A location of one such charging station is depicted in FIG. 14A. Each dock may be plugged into a power outlet on a wall, and permit the robot to interface with the dock for recharging, where the robot has charging terminals at power outlet height and/or at dock terminal height. The dock may employ celestial navigation, the robot using an upwardly-directed camera or sensor to recognize a 1- or 2-dimensional bar code, self-similar symbol, or other resolvable symbol projected onto the ceiling or other readily visible surface. The resolvable symbol may include information resolvable to the type of dock (charging, medication or consumable resupply, etc.) in the room, the typical use of the room (living room, dining room, kitchen, bedroom), the adjoining rooms, the number and/or position of doorways, and/or information recorded by the dock. The presence of a dock and type of a dock in a room may increment or change the comfort score, security score, etc., of the robot to improve the probability that the robot maintains a viable battery charge. The robot may detect the presence of the dock through any other suitable method, such as optical scanning for a symbol on a dock, RFID tag detection when an RFID tag is positioned on the dock, a pre-loaded map of dock locations, etc.

Figure 16:
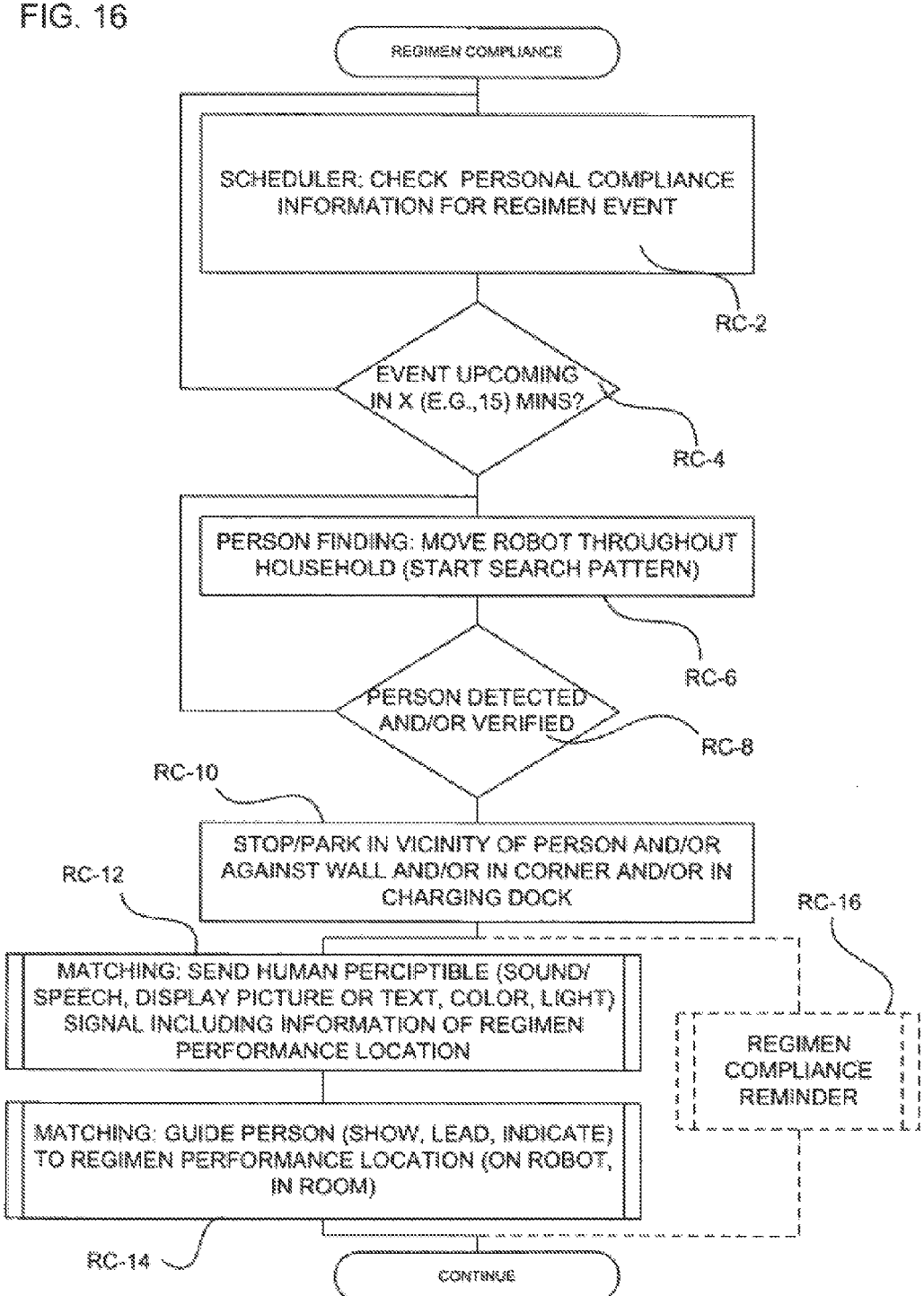
FIG. 16 depicts a regimen compliance algorithm in accordance with another embodiment of the present disclosure.

A regimen compliance assistance routine is detailed in FIG. 16. In step RC-2, the robot checks a database (locally, remotely) of personal regimen compliance information, such as medication dosage information that corresponds to the medication regimen of the resident, as well as postponement rules. The database includes, e.g., how many pills in a dose, when and how the medications are to be take, whether they can be delayed by a few minutes, an hour, before or after meals, which medications are to be taken together with others or not with others. This routine is applicable for health oriented regimens (exercise, therapy, meditation, etc.) and where compatible, the discussion herein of medical dosage information and "doses" includes activities associated with any kind of regimen.

The robot checks the information often enough to anticipate that it will need to be near the resident at a certain time in the future (e.g., frequently checking ahead to accommodate changes in schedule, or by setting ticklers ahead of the event). When an event is upcoming (anticipated or known due to a tickler/reminder) at RC-4, the robot begins to look for the person/resident. In the case of the proximity maintaining routines discussed herein, the likelihood that the resident is very near is good. However, even absent the proximity maintaining routines, the robot need only schedule enough time in advance to traverse the entire household, and in most cases will not need to. Rather than employ proximity events as previously described, the robot may learn a schedule by recording the rooms the resident is found in every day and time an event is needed, and in short order will learn the most likely room, the second most likely room, etc., for a time of day. The person finding routine employed at step RC-8 is as described herein, and may include a verification step to check the identity of the person.

When the resident has been located and their identity verified, the robot establishes a position next to the resident. The resident may be otherwise engaged, and so the robot takes up a position that is preferably unobtrusive (E.g., against a wall, in a nearby charging dock, in a corner of the room, beside the arm of the chair in which a resident sits) and awaits the scheduled event. In the case of a generalized regimen compliance event, at RC-16 the resident is reminded of the regimen activity they are expected to accommodate. For exercise, the robot may act as coach, may display exercises on screen, may link into a live exercise session, and may synchronize its own motions with those exercises to be performed by the resident (along with other appropriate movement expressions, modulated and controlled as discussed herein to match particular scripted events or non-scripted stimuli). For therapy, the robot may display therapies on screen, may guide the resident to particular equipment (or carry the same), may link into a live or recorded therapist, and may take the resident's reports of status information (e.g. following exercise or therapy, reporting heart rate, blood pressure, breathing rate, either by having the resident measure them or by using on-board interactive sensors).

It should be noted that as described herein, the robot contains full connectivity and support for power, network access, security, and mobility to health assisting appliances; one example of which is a "Health Buddy" available from Health Hero Network, Inc., Redwood City, Calif., and such as those discussed in U.S. Pat. No. 5,307,263, herein incorporated by reference in its entirety. A typical device is a 1.25 lb device with a small color LCD screen, soft buttons, and medical instrument and network interfaces. It includes may include USB ports, an RJ-45 Ethernet network port, and embedded-class memory (64 MB) and processing (ARM processor, Linux OS). The devices are typically powered by 5-24V DC via an AC adapter. The contemplated robot can provide more robust, longer lasting power (2400-9000 milliamp-hours) for appliance or instruments, as well as smart control of on-off cycles (turning on the Health Buddy only as needed); mobility and patient finding for the appliance itself as well as instruments, additional network connectivity to additional instruments, wireless devices, pagers, telecommunications; full-screen, full-support, and live tutorials and instructions; video conferencing, remote observation, statistical reporting, richer controls and interfaces. Such appliances may be connected via network interface to collect data from to blood glucose meters, peak flow meters, scales, blood pressure monitors, pulse oximeters and the like, and robot may intercept, split, transfer or otherwise link to the same instruments, and the regimen compliance reminder may hand off to or receive delegation from a Health Buddy or like device pursuant to independent or linked schedules, and subsequently route collected data, interface events, communications, and all other digitally transmissible information discussed herein via the appliance's supporting networks or the robot networks discussed herein. The Health Buddy is a Linux device having a limited subset of the connectivity and user interface elements of a robot as discussed herein, and all of the Health Buddy processes, software and interfaces, including user interfaces displayable on a screen and controllable by user interface elements such as a touch screen or soft buttons, may be directly run by the robot discussed herein. As discussed herein, regimen compliance, scheduling, interaction, reporting and all other compliance and medical reporting discussed herein, as supported by resident or patient finding, reminding, household navigation and resident location awareness, medication loading and carrying, privacy and permission administration, and human-robot interaction, expressly includes uses of appliances such as the Health Buddy supported by, carried by, and or linked to the mobile robot described herein, and the claims herein expressly consider such an accessory appliance to be fall within the literal language of a "robot," "robot system," or method of operating, navigating, or otherwise controlling a robot or robot system.

If the compliance event is associated with the taking of medications, steps RC-12 and RC-14 are specifically applicable. In the context of these claims, "matching" is the task of putting the resident in the same place at the same time as their medication, and may involve bringing the medication to the person or guiding the person to the medication. In a failure mode where mobility is not working, matching is replaced by mere reminders. In step RC-12, a human perceptible signal (recorded speech, synthesized speech, a displayed picture or displayed text, flashing or blinking lights, pointers, outlines, or highlights) is "sent" to the resident, and shows the resident the location where the medication is to be found (which may in fact be inches away carried by the robot, or may be in a room where a medication dispenser that is a networked part of the robot system is kept, or may be where medication is normally kept for that resident, as well as other variations discussed herein). Guiding, as discussed in step RC-14, is the task of showing or leading the resident to the location of the medication, and may be showing an image of the medication on the robot, a pointer or indicator drawing attention to a robot-carried dispenser, or actually moving the robot toward the bathroom or other room where a dispenser is located while expressing that the resident should accompany the robot by spoken messages, sounds, or expression motions.

Figure 17A:
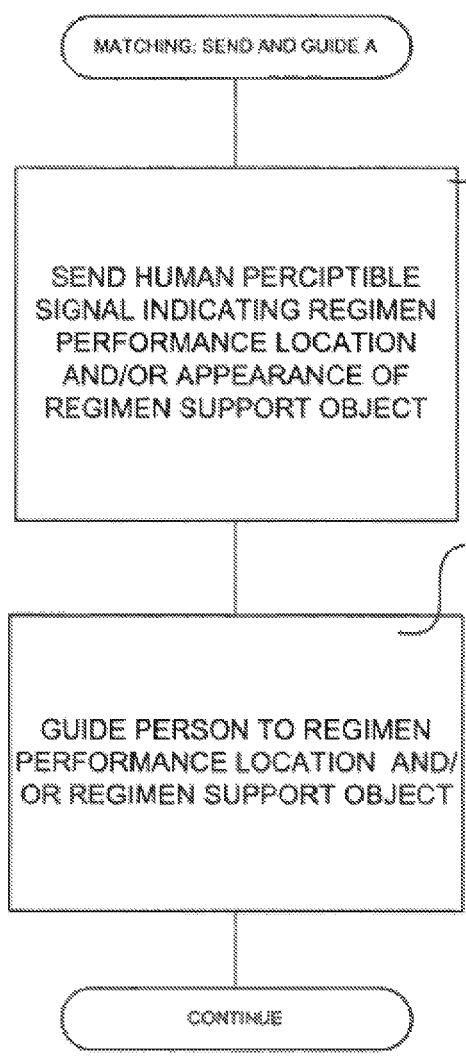
FIGS. 17A-17B depict matching algorithms in accordance with embodiments of the present disclosure.
Figure 17B:
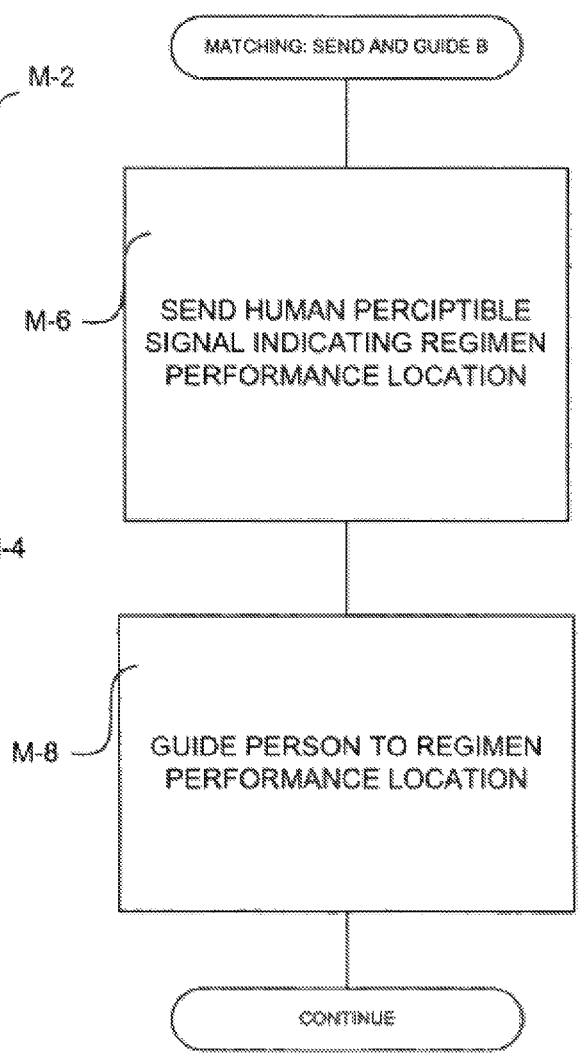

One kind of matching is shown in FIG. 17A. In this routine, a regimen support object could include a robot-carried dispenser as is shown in FIGS. 3A-3C, which may be carried by the robot or in a location stored by the robot, and could also include medical instruments (blood pressure monitor, glucose, heart rate, etc.) or therapy instruments carried by the robot or in locations stored by the robot. The robot sends a human perceptible signal at step M-2 as noted above, indicating the regimen performance location, in this case the location of the dispenser on the robot. The appearance of the regimen support object (i.e., a pictorial depiction of it) as the object is positioned on the robot is shown on the display (which may also be projected onto a nearby surface) or otherwise. The robot guides the resident at step M-4, by showing an animation or activating secondary indicia near the regimen support object, to the object. A second kind of matching is shown in FIG. 17B. In this routine, the robot sends a human perceptible signal in step M-6 as noted above, indicating the regimen performance location, in this case a room or other location where the medication is kept or other compliance activity is performed. The robot guides the resident to the location in step M-8.

Figure 18A:
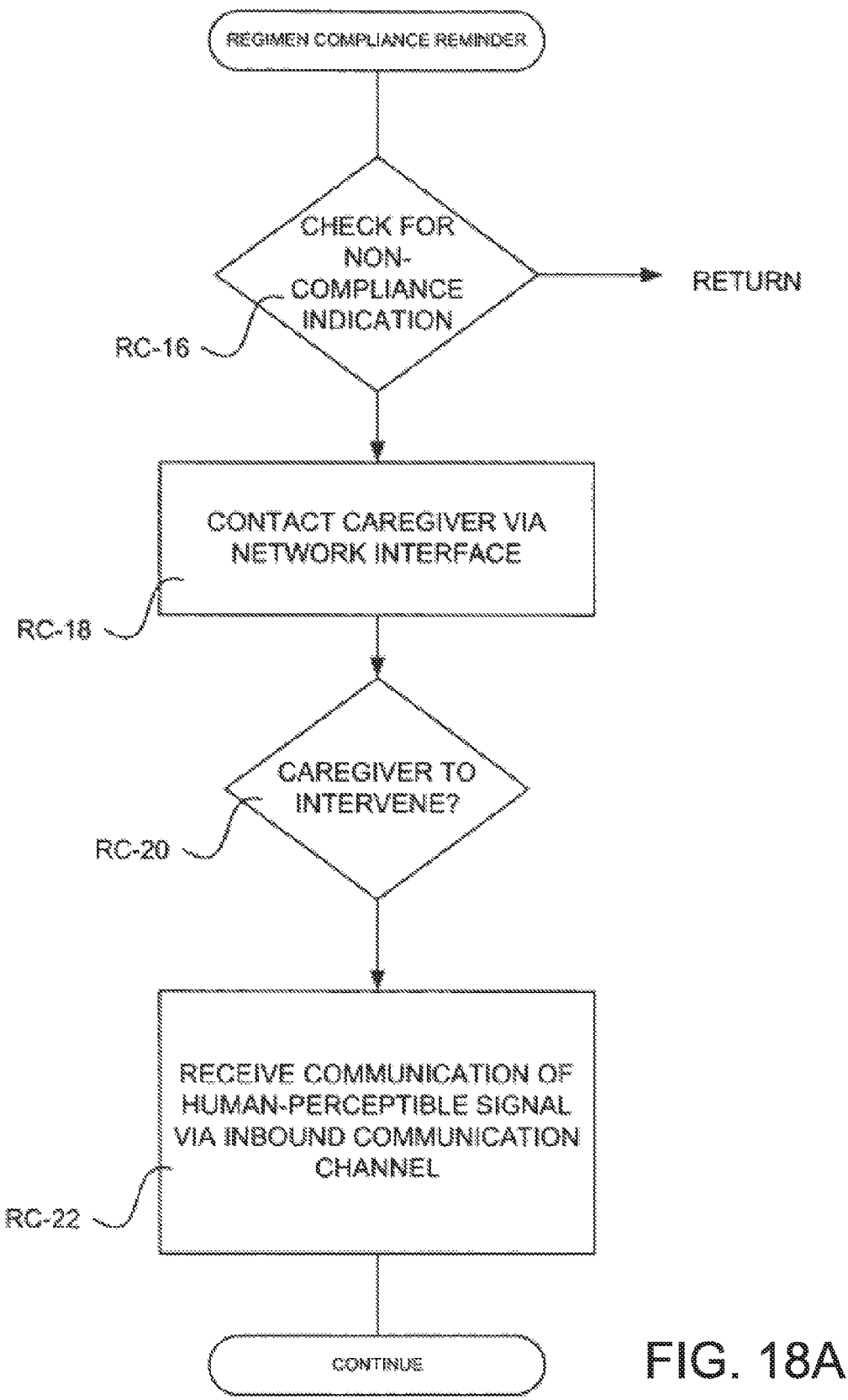
FIG. 18A depicts a regimen compliance reminder algorithm in accordance with another embodiment of the present disclosure.

FIG. 18A shows a routine for conducting a reminder routine and providing a remote caregiver with an opportunity to intervene. This routine can take place at step RC-16 of FIG. 16. At step RC-16 herein, after an appropriate period and a reminder as performed by any method discussed herein, the robot checks for a non-compliance indication, e.g., a recorded refusal and/or failure of the resident to successfully complete a schedule regimen event. The robot may record this via any of the interaction methods discussed herein. The procedure is terminated for a successful completion. At step RC-18, the robot connects to the network (using the security and authentication methods discussed herein) and to the caregiver via a preferred channel (desktop video chat, cell phone, e-mail). The caregiver is given the opportunity to intervene (in some cases, as controlled by the resident's previous granting or refusal of permission to permit regimen compliance intervention by the caregiver) at step RC-20. If the caregiver elects to intervene, the robot receives a communication of a human-perceptible signal (an e-mail, recorded message, live chat or telephone call, text to be spoken by the robot) via an inbound communication channel (e.g., a channel crossing the network(s) to which the robot and caregiver are both connected).

FIG. 18B shows a routine for loading medication into a medication dispenser that can be controlled or monitored by the robot. As previously discussed, such a dispenser can be simple or complex. A simple version would be a standard plastic compartmented device that is carried by the robot, in which case the robot does not monitor the device but only interacts with the resident. Additional features of a dispenser may include: electromechanical opening and closing of compartments and presentation of compartments; magazining of multi-day doses or entire bottles of pills; monitoring of magazines, optionally connected to payment systems and/or verification by the resident, so as to schedule mail-order or other deliveries of replacement supplies carrying of "Dixie" cups of pills or water, tillable or disposable bladders of water, or a water bottle; sensored detection of medication presence or absence; sensored detection of compartments individually or of a presence or absence of an entire dispenser caddy; any of the above connected to robot or robot base station via simple microprocessor together with serial interface, sensor bus, general purpose I/O or wired or RF network.

FIG. 18B describes a routine in which the resident the person who is to take the medication loads the dispenser him or herself. As earlier noted, the dispenser may be permanent on the robot, carried by the robot, networked but located in a bathroom or the like, and may also switch between these latter two roles. The steps are mechanistic and somewhat verifiable, but can be sped through once the resident becomes adept at interacting with the robot and dispenser. Most residents that could gain substantial benefit from a robot assistant would be responsible for their own medication planning in any case. However, in all cases in FIG. 18B, the resident may be replaced with the caregiver, with an orderly, another family member, etc. In step ML-2, the robot retrieves from local or remote memory or database the medication complement for that day, and may also retrieve from local or remote database images of medications in the complement, dosage rules (so as to determine whether to collect, load, or later supply water when a dispenser includes such capability), and the like.

In step ML-4, the resident is asked whether or not he or she is ready to load the dispenser. This is optionally handled as any other compliance event discussed herein, and can be subject to snooze delays, reporting to the caregiver, and like procedures detailed herein. A simple dialogue is shown at MSG-4 in which the robot checks whether the resident has left-over medication in the dispenser, and/or expects that he or she has all medication available. In step ML-6, the robot repeats and steps through each medication. A simple dialogue is shown at MSG-6, in which the robot explains the particular regimen for a medication, uses the name of the medication, shows an image of the medication, and requests the user to load a chamber, compartment, disposable cup, or other holder with the medication. More medications are stepped through in the same way. The routine does not show more significant interaction (e.g., such as the resident wishing to ask about side effects or other queries), but more responsive dialogues (such as are discussed herein) would permit this to occur. Once the medications have all been loaded, the robot may ask the resident to quickly step through and double-check the day's complement (ML-8), the caregiver is permitted to or designated to check the medication complement (ML-10), the robot may open a communication channel to the caregiver (step ML-10, the same as or similar to the above discussion of steps RC-18 and step RC-20), and then permit the caregiver to ask questions of the resident (or for a richly instrumented dispenser, directly check the status). The dispenser may be arranged (with a transparent or open cover) and positioned so that it is visible to a camera of the robot, and indeed the resident may hold a dispenser so configured up to one of the robot's cameras.

In addition to the above-identified functionality, the robot may be equipped with RFID or barcode sensors for assisting with shopping, etc. in an example, the robot may accompany the resident to a store or supermarket, in which the items for sale include RFID tags (or barcodes, or any other suitable identification scheme) for identification and inventory. If the resident wants to purchase an item, the robot may scan the RFID information of the indicated product, and relay the information to the store for purchasing assistance. In addition, the robot may keep track of food or supply inventories in the household by scanning RFID tags or barcodes of items in the refrigerator or pantry. When items run low, the robot may retrieve additional supplies and restock, for example. Such functionality is not limited to only food or store items, but may also be applied to any suitable items, such as clothing, automobile parts, etc.

In addition, the robot may assist in keeping the household clean, by monitoring clutter or by keeping track of cleaning schedules. A clutter level can be scored according to, e.g., (i) a number of collisions or proximity detections per unit time or per unit distance traveled (these could be separated into wall, furniture, and non-wall detections based on sensor data); and/or (ii) a number of differently colored or differently textured items per unit area detected by cameras viewing the ground plane in front of the robot; and/or (iii) a number of medium-range obstacles detected per unit time, distance, or area by ranging sensors. In this manner, the robot may apply image analysis to views of the house obtained from an on-board camera, and determine if the house has become too messy, or may determine that clutter has accrued when the robot too frequently encounters obstacles along paths that should be or are historically clear, for example.

The robot may facilitate bill paying by sharing checklists between the resident and a remote caregiver. Accordingly, when a bill payment or other household task is due, the robot may present a checklist of tasks to the resident on its display screen (and may also verbally or audibly inform the person). If tasks have not been completed, the robot may notify a caregiver, if concordant with the privacy permissions. Also, the task checklists may be programmed by either the resident or by a remote caregiver, for example. The robot's cameras also may be used to photograph and/or OCR bills and notices.

If the resident requires assistance dealing with an outside third party or service provider, such as a housing contractor, salesperson, or nurse or aide, the robot may provide on-the-spot teleconferencing between the people present at the house and the remote caregiver, for example. Furthermore, by providing remote visual inspection capabilities, the robot may facilitate housing safety inspections by permitting a remote inspector (or caregiver) to view various locations of the house. The robot may also include safety sensors such as a smoke detector, radon gas detector, carbon monoxide or CO2 sensor, or the like.

The robot may use an infrared emitter to control one or more home entertainment devices, such as televisions, VCRs, DVD players, or stereo systems. For example, the robot may function as a device coordinator, and control several pieces of equipment simultaneously or according to a sequence, such that the robot could turn on both the television and DVD player (and switch a stereo mixer to input from the DVD player, for example) when the resident wants to view a DVD. As another feature, the robot may be easier to locate than a small remote control, and the robot may also include a database of remote control codes for various products and manufacturers, relieving the resident of having to program a remote control for multiple items.

Furthermore, the robot (or other appliance having a camera and IR modulated emitter) may detect RFID, barcode, or brand trademarks on the home equipment, and discern the appropriate remote control codes therefore without requiring further input from the person. The robot (or remote control or other appliance, having a connection to a camera and IR modulated emitter) may photograph part of or the entire front face panel of any remote controlled equipment (TV, stereo, video recorder, cable box, CD/DVD/disc player, home theater, amplifier, tuner, lighting, fans, air conditioners, video games, etc.). The robot may then relay an image of the equipment to a remote computer, which may analyze the image for brand information or model information, and relay the appropriate remote control code back to the robot, for example, and therefore the robot need not necessarily include image processing capabilities locally.

Visual pattern recognition (which may employ a scale invariant feature transform "SIFT" system such as the ViPR™ system, Evolution Robotics of Pasadena, Calif., or other known scale invariant feature transform algorithms such as "SURF") may identify features or distinct regions and compute from 1-1000 descriptors of unique visual patterns, which in combination may be used to uniquely identify the brand and model (or model family) of equipment, including OEM variations. Any portion of this process can be carried out on the robot or remotely on a server; in most cases the robot would simply send the image to the server for decomposition and comparison to the database of trained equipment images. A voting or probabilistic routine can employ feature votes to cross-correlate features in trained images to similar features in the recorded image. The votes are tabulated to identify the most likely identity for the equipment or different items of equipment. The robot selects or receives the appropriate libraries of remote control IR modulated codes for use with every device photographed (e.g., all of the codes for each of the TV, DVD player, and cable box). A single photograph or several photographs may be decomposed or analyzed to identify every piece of equipment in one place, in a room or in the residence.

The robot can then employ a compatibility routine to control the devices according to the overall task specified by the resident, by coordinating compatibility of inputs and outputs (e.g., in response to a command to watch TV, the robot may activate, via the received IR codes: the TV ON, the DVD OFF, the cable box ON, and the TV to the CABLE input; in response to a command to watch a DVD, the robot may activate, via the received IR codes, the TV ON, the DVD ON, the cable box OFF, and the TV to the S-VIDEO input). In this manner, the robot would operate similarly to the family of Harmony™ Remote Controls sold by Logitech Inc., of Fremont, Calif., using a similar database of IR codes and products. The Harmony devices are programmed by the user, suffer from drift when one controlled device is no longer synchronized from the others, and employ an all-off routine to reset all devices to a default state in order to recover the input/state synchronization. In contrast, the present robot or remote control or other appliance, having a connection to a camera and IR-modulated emitter may use the camera and aforementioned visual pattern recognition to detect the on, off, or other active (e.g., wrong input selected, volume low) state of any device by status lights, status indications (a picture on the TV), status messages (on the TV screen or device display) or other pattern recognition to avoid using an all-off routine, instead resynchronizing the devices to one another based on the present state of inputs and other functions. The robot or other device may also use speech recognition to receive verbal remote control commands from the person, for example.

With regard to verbal input and/or output, the mobile robot may include a database of verbal patterns for various events and/or tasks, such that the robot may correctly interpret verbal input associated with a particular task. For example, when the robot is performing a medication-related task, the robot may load medical terminology into its immediate speech-recognition pattern memory; if the robot later performs a shopping task, the robot may switch to a clothing- or grocery-related speech pattern database.

Many examples are given herein that relate to elder care. However, the same embodiments of the disclosure are readily adaptable for care of children or in limited cases, adults who require caregiver assistance. In order to provide mental stimulation to the person, the robot may use sound, music, and/or games, either spontaneously, or in response to a request by the resident or caregiver, or in accordance with a predetermined schedule. In addition, the robot may perform any of the following interactive activities: play games using a touch screen; play word games (audio only, or via the display screen, or both); play music; play audio books; tell stories or recite audio books; play daily news stories, weather, or sports scores; look up reference information (encyclopedia, TV guides) (in response to verbal input or questions from the person, for example); look up financial information (stock prices, bank balance); receive emails and instant messages; show digital photos sent by family and friends; play videos sent by family and friends; talk on the phone; participate in a video conference; produce a daily report sent to a caregiver in email that lists activities the resident performed that day; play audio clips of the resident talking to the robot; show photos of the resident in their home; give medication reminders including dosage and timing; give physical activity reminders (e.g., go for a walk, do stretches); give daily event reminders (e.g., TV show times, appointments, birthdays); let a caregiver talk to and see the resident from their computer; let a caregiver navigate the robot around the person's house to check on things; include privacy control (the robot requires permission from the resident before turning on a camera or letting a remote caregiver do a virtual visit; include a trip detector (the robot detects when the resident is nearby, and gets out of the way or makes sounds and flashes lights); include caregiver management; and/or give updates (new games, music, videos and photos may be sent to the robot automatically via an Internet feed, or specifically by a caregiver or third party from a remote location (via e-mail or web interface)).

A number of implementations have been described. Nevertheless, it will be understood that various modifications may be made without departing from the spirit and scope of the disclosure. Accordingly, other implementations are within the scope of the following claims.

What is claimed is:

1. A mobile robot comprising:
a robot body;
a drive system having one or more wheels supporting the robot body to maneuver the robot across a floor surface;
a riser having a proximal end and a distal end, the proximal end disposed on the robot body; and
a head disposed on the distal end of the riser, the head comprising:
a display;
a teleconferencing camera disposed adjacent the display; and
a navigation camera separate from the teleconferencing camera; and
a controller in communication with the drive system, the display, the teleconferencing camera, and the navigation camera, the controller configured to command the drive system to navigate the robot to a target location using image data received from the navigation camera and initiate a video teleconferencing session at the target location.

2. The mobile robot of claim 1, wherein the riser is extendible, having a variable distance between its proximal and distal ends.

3. The mobile robot of claim 2, wherein the riser comprises pivoted, jointed, folding or telescoping parts to provide the variable distance between its proximal and distal ends.

4. The mobile robot of claim 1, further comprising at least two wheels supporting the robot body.

5. The mobile robot of claim 1, wherein the navigation camera is oriented to provide a ground plane view in front of the robot, the controller configured to command the drive system to circumnavigate obstacles detected in front of the robot using image data received from the navigation camera while navigating to the target location.

6. The mobile robot of claim 1, wherein the navigation camera is orientated to observe ceiling features above the robot.

7. The mobile robot of claim 1, wherein the display comprises a tablet computer.

8. The mobile robot of claim 7, wherein the tablet computer is in communication with the drive system.

9. The mobile robot of claim 7, wherein the tablet computer is releasably attached to the riser and comprises a wireless communications transceiver.

10. The mobile robot of claim 1, wherein the controller is configured to capture topological adjacency information of different rooms within an operating environment of the robot when the robot travels from room to room, and the controller is configured to command the drive system to navigate the robot to the target location from a present location of the robot using room-to-room navigation based on the topological adjacency information.

11. The mobile robot of claim 1, wherein the controller is configured to navigate to the target location based on a schedule indicating a time and the target location associated with the video teleconferencing session.

12. The mobile robot of claim 1, wherein the controller is in communication with a user device executing a user interface configured to display a user map including a set of room identity markers, each room identity marker graphically representing a particular room within an operating environment of the robot, and receive a user selection of one of the room identity markers causes the user device to transmit a navigation command to the controller to navigate the robot to the particular room associated with the one of the room identity markers.

13. The mobile robot of claim 12, wherein the user interface is configured to display the user map upon the display of the head.

14. The mobile robot of claim 12, wherein the user interface is configured to display the user map upon a remote display located remotely from the robot.

15. The mobile robot of claim 12, wherein the room identity markers comprise at least one of icons or text.

16. The mobile robot of claim 12, wherein the controller is configured to:
receive the navigation command from the user device to navigate the robot to the particular room associated with the selected room identity marker;
command the drive system to navigate the robot to the particular room;
determine whether the robot recognizes the particular room associated with the selected room identity marker using image data received from the navigation camera; and
initiate the video teleconferencing session when the robot recognizes the particular room associated with the one of room identity markers.

17. The mobile robot of claim 12, wherein the user interface executed on the user device is configured to display a view in front of the robot based on image data received by at least one of the teleconferencing camera or the navigation camera, the user interface permitting a user to select a feature observed in the view in front of the robot to command the robot to move autonomously to the selected feature.

18. The mobile robot of claim 12, wherein the user interface executed on the user device is configured to display one or more navigation buttons configured to receive a user input, the user input causing the user device to transmit a movement command to the controller to move the robot at a direction and heading based on a navigation button of the one or more navigation buttons receiving the user input.

19. The mobile robot of claim 1, wherein: the controller is in communication with one or more charging stations located within an operating environment of the robot, each charging station configured to recharge one or more batteries of the robot when the robot docks with a charging station.

20. The mobile robot of claim 19, wherein the controller is configured to command the drive system to maneuver the robot to dock with any one of the one or more charging stations when the robot is not in use and/or the one or more batteries need charging.

* * * * *